US008299044B2

(12) United States Patent
Takagi et al.

(10) Patent No.: US 8,299,044 B2
(45) Date of Patent: Oct. 30, 2012

(54) APOPTOSIS INDUCER FOR CANCER CELL

(75) Inventors: Motoki Takagi, Kamakura (JP); Akira Shimamoto, Hiroshima (JP); Yasuhiro Furuichi, Kamakura (JP); Ayumi Sato, Fujisawa (JP)

(73) Assignee: Genecare Research Institute Co., Ltd., Kanagawa (JP)

( * ) Notice: Subject to any disclaimer, the term of this patent is extended or adjusted under 35 U.S.C. 154(b) by 155 days.

(21) Appl. No.: 12/643,938

(22) Filed: Dec. 21, 2009

(65) Prior Publication Data

US 2010/0168209 A1 Jul. 1, 2010

Related U.S. Application Data

(63) Continuation of application No. 10/556,968, filed as application No. PCT/JP2004/007145 on May 19, 2004, now abandoned.

(30) Foreign Application Priority Data

May 19, 2003 (JP) ................................ 2003-140685

(51) Int. Cl.
*C12N 15/11* (2006.01)
*C07H 21/02* (2006.01)

(52) U.S. Cl. .................................... 514/44 A; 536/24.5

(58) Field of Classification Search ........................ None
See application file for complete search history.

(56) References Cited

U.S. PATENT DOCUMENTS

| | | | | |
|---|---|---|---|---|
| 6,448,080 | B1 | 9/2002 | Ward et al. | 435/375 |
| 7,056,704 | B2 * | 6/2006 | Tuschl et al. | 435/91.1 |
| 2003/0171310 | A1 | 9/2003 | Ward et al. | 514/44 |
| 2004/0259247 | A1 | 12/2004 | Tuschl et al. | 435/375 |
| 2009/0028861 | A1 | 1/2009 | Takagi et al. | 424/138.1 |
| 2009/0215867 | A1 | 8/2009 | Takagi et al. | 514/44 R |

FOREIGN PATENT DOCUMENTS

| | | |
|---|---|---|
| JP | 11-276173 | 10/1999 |
| JP | 2000-166600 | 6/2000 |
| WO | 02/068590 | 9/2002 |

OTHER PUBLICATIONS

Elbashir et al. (Methods 26:199-213, 2002).*

Harborth et al. (J. Cell Sci. 114:4557-4565, 2001).*

Seki et al., Genbank Accession No. D37984, submitted Aug. 17, 1994.

Vickers et al., "Effects of RNA secondary structure on cellular antisense activity," *Nucleic Acids Research 28*(6): 1340-1347, 2000.

Bischof et al., "Selective Cleavage of BLM, the Bloom Syndrome Protein, during Apoptotic Cell Death," *Journal of Biological Chemistry*, 276(15):12068-12075, Apr. 13, 2001.

Brosh et al., "Werner Syndrome Protein Interacts with Human Flap Endonuclease 1 and Stimulates its Cleavage Activity," *EMBO Journal*, 20(20):5791-5801, 2001.

Chester et al., "Stage-specific Apoptosis, Developmental Delay, and Embryonic Lethality in Mice Homozygous for a Targeted Disruption in the Murine Bloom's Syndrome Gene," *Genes & Development*, 12(21):3382-3393, Nov. 1, 1998.

Davalos et al., "Bloom Syndrome Cells Undergo p53-dependent Apoptosis and Delayed Assembly of BRCA1 and NBS1 Repair Complexes at Stalled Replication Forks," *Journal of Cell Biology*, 162(7):1197-1209, Sep. 29, 2003.

Doe et al., "Partial Suppression of the Fission Yeast rqh1-phenotype by Expression of a Bacterial Holliday Junction Resolvase," *EMBO Journal*, 19(11):2751-2762, Jun. 1, 2000.

Ellis et al., "The Bloom's Syndrome Gene Product is Homologous to RecQ Helicases," *Cell*, 83(4):655-666, Nov. 17, 1995.

Ellis et al., "Molecular Genetics of Bloom's Syndrome," *Human Molecular Genetics*, 5:1457-1463, 1996.

Franchitto et al., "The $G_2$-phase Decatenation Checkpoint is Defective in Werner Syndrome Cells" *Cancer Research*, 63(12):3289-3295, Jun. 15, 2003.

Goto, "Hierarchical Deterioration of Body Systems in Werner's Syndrome: Implications for Normal Ageing," *Mechanisms of Ageing and Development*, 98(3):239-254, Dec. 1997.

Hanada et al., "RecQ DNA Helicase is a Suppressor of Illegitimate Recombination in *Escherichia coli*," *Proc. Natl. Acad. Sci. U S A*, 94(8):3860-3865, Apr. 15, 1997.

Johnson et al., "Association of the Bloom Syndrome Protein with Topoisomerase IIIα in Somatic and Meiotic Cells," *Cancer Research*, 60(5):1162-1167, Mar. 1, 2000.

Kawabe et al., "Differential Regulation of Human RecQ Family Helicases in Cell Transformation and Cell Cycle," *Oncogene*, 19(41):4764-4772, Sep. 28, 2000.

Kitao et al., "Cloning of Two New Human Helicase Genes of the RecQ Family: Biological Significance of Multiple Species in Higher Eukaryotes," *Genomics*, 54(3):443-452, Dec. 15, 1998.

Kitao et al., "Mutations in RECQL4 Cause a Subset of Cases of Rothmund-Thomson Syndrome," *Nature Genetics*, 22(1):82-84, May 1999.

Lindor et al., "Rothmund-Thomson Syndrome in Siblings: Evidence for Acquired in Vivo Mosaicism," *Clin Genet*, 49(3):124-129, Mar. 1996.

Mohaghegh et al., "The Bloom's and Werner's Syndrome Proteins are DNA Structure-specific Helicases," *Nucleic Acids Research*, 29(13):2843-2849, Jul. 1, 2001.

Myung et al., "SGS1, the *Saccharomyces cerevisiae* Homologue of BLM and WRN, Suppresses Genome Instability and Homeologous Recombination," *Nature Genetics*, 27(1):113-116, Jan. 2001.

Nakayama, "RecQ Family Helicases: Roles as Tumor Suppressor Proteins," *Oncogene*, 21(58):9008-9021, Dec. 16, 2002.

Nakayama et al., "Isolation and Genetic Characterization of a Thymineless Death-resistant Mutant of *Escherichia coli* K12: Identification of a New Mutation (recQ1) that Blocks the RecF Recombination Pathway," *Mol Gen Genet*, 195(3):474-480, 1984.

(Continued)

*Primary Examiner* — Richard Schnizer
(74) *Attorney, Agent, or Firm* — Seed IP Law Group PLLC

(57) ABSTRACT

The present invention revealed that by suppressing the expression of the WRN gene, the BLM gene, or the RecQ1 gene, which belong to the RecQ helicase family, apoptosis is induced in various cancer cells and their proliferation is suppressed. Compounds that suppress the expression of RecQ helicase family genes or the functions of RecQ helicase proteins are thought to have the activity of inducing apoptosis.

3 Claims, 16 Drawing Sheets

OTHER PUBLICATIONS

Pichierri et al., "Werner's Syndrome Protein is Required for Correct Recovery after Replication Arrest and DNA Damage Induced in S-Phase of Cell Cycle," *Molecular Biology of the Cell*, 12(8):2412-21, Aug. 2001.

Poot et al., "Werner Syndrome Diploid Fibroblasts are Sensitive to 4-nitroquinoline-N-oxide and 8-Methoxypsoralen: Implications for the Disease Phenotype" *FASEB Journal*, 16(7):757-758, May 2002.

Sakamoto et al., "Werner Helicase Relocates into Nuclear Foci in Response to DNA Damaging Agents and Co-localizes with RPA and Rad51," *Genes to Cells*, 6(5):421-430, May 2001.

Seki et al., "Molecular Cloning of cDNA Encoding Human DNA Helicase Q1 which has Homology to *Escherichia coli* Rec Q Helicase and Localization of the Gene at Chromosome 12p12," *Nucleic Acids Research*, 22(22):4566-4573, Nov. 11, 1994.

Stein et al., "Analysis of the Role of RecQ Helicases in RNAi in Mammals," *Biochemical and Biophysical Research Communications*, 291(5):1119-1122, Mar. 15, 2002.

Sugimoto et al., "Incorrect Use of 'Immortalization' for B-Lymphoblastoid Cell Lines Transformed by Epstien-Barr Virus," *Journal of Virology*, 73(11):9690-9691, Nov. 1999.

Tahara et al., "Abnormal Telomere Dynamics of B-lymphoblastoid Cell Strains from Werner's Syndrome Patients Transformed by Epstein-Barr Virus," *Oncogene*, 15(16):1911-1920, Oct. 16, 1997.

Wang et al., "Functional Interaction of p53 and BLM DNA Helicase in Apoptosis," *Journal of Biological Chemistry*, 276(35):32948-32955, Aug. 31, 2001.

Wu et al., "Effect of Age and Apoptosis on the Mouse Homologue of the huWRN Gene," *Mechanisms of Ageing and Development*, 103(1):27-44, Jun. 1, 1998.

Wu et al., "Potential Role for the BLM Helicase in Recombinational Repair Via a Conserved Interaction with RAD51," *Journal of Biological Chemistry*, 276(22):19375-19381, Jun. 1, 2001.

Yannone et al., "Werner Syndrome Protein is Regulated and Phosphorylated by DNA-dependent Protein Kinase," *Journal of Biological Chemistry*, 276(41):38242-38248, Oct. 12, 2001.

Yu et al., "Positional Cloning of the Werner's Syndrome Gene," *Science*, 272(5259):258-262, Apr. 12, 1996.

Brosh et al., "Werner syndrome protein interacts with human flap endonuclease 1 and stimulates its cleavage activity," *The EMBO Journal 20*(20): 5791-5801, 2001.

Cui et al., "Characterization of the DNA-unwinding Activity of Human RECQ1, a Helicase Specifically Stimulated by Human Replication Protein A," *The Journal of Biological Chemistry 278*(3): 1424-1432, Jan. 17, 2003.

Hickson et al., "Role of the Bloom's syndrome helicase in maintenance of genome stability," *Biological Society Transactions* (*29*)(part 2): 201-204, 2001.

Xia et al., "siRNA-mediated gene silencing in vitro and in vivo," *Nature Biotechnology 20*: 1006-1010, Oct. 2002.

Bennett et al., "Antisense oligonucleotides as a tool for gene functionalization and target validation," *Biochimica Biophysica Acta 1489*: 19-30, 1999.

Brummelkamp et al., "A system for stable expression of short interfering RNAs in mammalian cells," *Science 296*: 550-553, 2002.

Elbashir et al., "Analysis of gene function in somatic mammalian cells using small interfering RNAs," *Methods 26*: 199-213, 2002.

Furuichi, "Premature aging and predisposition to cancers caused by mutations in RecQ family helicases," *Ann. N.Y. Acad. Sci.* 928: 121-131, 2001.

Harborth et al., "Identification of essential genes in cultured mammalian cells using small interfering RNAs," *J. Cell Sci.* 114: 4557-4565, 2001.

Holen et al., "Positional effects of short interfering RNAs targeting the human coagulation trigger Tissue factor," *Nucleic Acids Res.* 30(8): 1757-1766, 2002.

Jen et al., "Suppression of gene expression of targeted disruption of messenger RNA: Available options and current strategies," *Stem Cells 18*: 307-319, 2000.

Vickers et al., "Efficient Reduction of Target RNAs by small interfering Rna and RNase H-dependent Antisense Agents," *J. Biol. Chem.* 278(9): 7108-7118, 2003.

Wu et al., "Substrate-specific inhibition of RecQ helicase," *Nucleic Acids Res.* 29: 1765-1771, 2001.

U.S. Appl. No. 13/473,328, filed May 16, 2012, entitled "Cancer Cell-Specific Apoptosis-Inducing Agents That Target Chromosome Stabilization-Associated Genes," 182 pages.

* cited by examiner

NUCLEOTIDE SEQUENCES OF siRNAs USED IN EXPERIMENTS

RecQ1 guucagaccacuucagcuudTdT
aagcugaaguggucugaacdTdT
↓
guucagaccacuucagcuuTT (SEQ ID NO: 1)
TTcaagucuggugaagucgaa

WRN guucuugucacguccucugdTdT
cagaggacgugacaagaacdTdT
↓
guucuugucacguccucugTT (SEQ ID NO: 2)
TTcaagaacagugcaggagac

BLM cgucacucagccagaacacdTdT
guguucuggcugagugacgdTdT
↓
cgucacucagccagaacacTT (SEQ ID NO: 3)
TTgcagugagucggucuugug

RTS gcuucgagagcuacgugcadTdT
ugcacguagcucucgaagcdTdT
↓
gcuucgagagcuacgugcaTT (SEQ ID NO: 4)
TTcgaagcucucgaugcacgu RecQ5 gguaacaaggacgucuuugdTdT
caaagacguccuuguuaccdTdT
↓
gguaacaaggacgucuuugTT (SEQ ID NO: 5)
TTccauuguuccugcagaaac siRNA SEQUENCES THAT STRONGLY SUPPRESSED GENE EXPRESSION, OTHER THAN THOSE LISTED ABOVE RecQ1 gccuaugaagcaaggagaudTdT (SEQ ID NO: 31/
aucuccuugcuucauaggcdTdT "dTdT" IS REPRESENTED BY "TT" IN THE SEQUENCE LISTING)

guucacugcuguagucagudTdT (SEQ ID NO: 32/
acugacuacagcagugaacdTdT "dTdT" IS REPRESENTED BY "TT" IN THE SEQUENCE LISTING)

gauccugaagcaggcagagdTdT (SEQ ID NO: 33/
cucugccugcuucaggaucdTdT "dTdT" IS REPRESENTED BY "TT" IN THE SEQUENCE LISTING)

gccagaugugagguuuguudTdT (SEQ ID NO: 34/
aacaaaccucacaucuggcdTdT "dTdT" IS REPRESENTED BY "TT" IN THE SEQUENCE LISTING)

FIG. 1

WRN

| | |
|---|---|
| ggagaucaguggaaacuucdTdT<br>gaaguuuccacugaucuccdTdT | (SEQ ID NO: 35/<br>"dTdT" IS REPRESENTED BY "TT" IN THE SEQUENCE LISTING) |
| gaccaagugcuacagcuuadTdT<br>uaagcuguagcacuuggucdTdT | (SEQ ID NO: 36/<br>"dTdT" IS REPRESENTED BY "TT" IN THE SEQUENCE LISTING) |

RTS

| | |
|---|---|
| gugaggaagacacagaugcdTdT<br>gcaucugugucuuccucacdTdT | (SEQ ID NO: 37/<br>"dTdT" IS REPRESENTED BY "TT" IN THE SEQUENCE LISTING) |
| ggaccagauaugugacuucdTdT<br>gaagucacauaucugguccdTdT | (SEQ ID NO: 38/<br>"dTdT" IS REPRESENTED BY "TT" IN THE SEQUENCE LISTING) |

RecQ5

| | |
|---|---|
| gccaaugucagguuugucgdTdT<br>cgacaaaccugacauuggcdTdT | (SEQ ID NO: 39/<br>"dTdT" IS REPRESENTED BY "TT" IN THE SEQUENCE LISTING) |
| ggaaggagcugcuugcugadTdT<br>ucagcaagcagcuccuuccdTdT | (SEQ ID NO: 40/<br>"dTdT" IS REPRESENTED BY "TT" IN THE SEQUENCE LISTING) |

FIG. 2

RecQ1-1 : guucagaccacuucagcuuTT (THIS SEQUENCE WAS USED IN ALL EXPERIMENTS) (SEQ ID NO: 1)
RecQ1-2 : gccuaugaagcaaggagauTT (SEQ ID NO: 31)
RecQ1-3 : guucacugcuguagucaguTT (SEQ ID NO: 32)
RecQ1-4 : gauccugaagcaggcagagTT (SEQ ID NO: 33)
RecQ1-5 : gccagaugugagguuuguuTT (SEQ ID NO: 34)
RecQ1-6 : gcuugaaacuauuaacguaTT (SEQ ID NO: 43)
RecQ1-7 : gaccacaguucauagaaaaTT (SEQ ID NO: 44)
RecQ1-8 : ggcucaacauuuugaugaaTT (SEQ ID NO: 45)
RecQ1-9 : ggaacugaaugaaaaacucTT (SEQ ID NO: 46)
RecQ1-10 : gguucaugcugaaaugguaTT (SEQ ID NO: 47)
RecQ1-11 : gcuugaaacuauuaacguaTT (SEQ ID NO: 48)
RecQ1-12 : gcaaggagauuuacucgaaTT (SEQ ID NO: 49)
RecQ1-13 : gagcuuauguuaccaguuaTT (SEQ ID NO: 50)
RecQ1-14 : ccauggucugguaaaguuaTT (SEQ ID NO: 51)
RecQ1-15 : agaacuuacggaaaggcaaTT (SEQ ID NO: 52)

WRN1 : guucuugucacguccucugTT (THIS SEQUENCE WAS USED IN ALL EXPERIMENTS) (SEQ ID NO: 2)
WRN2 : ggagaucaguggaaacuucTT (SEQ ID NO: 35)
WRN3 : ccuucaagcuaaugaagaaTT (SEQ ID NO: 53)
WRN4 : agucuaacuuggagaaguuTT (SEQ ID NO: 54)
WRN5 : ggaugaaugugcagaauaaTT (SEQ ID NO: 55)
WRN6 : ggacaaaacgaaaaggggaTT (SEQ ID NO: 56)
WRN7 : aggcgaaaaacagggaauaTT (SEQ ID NO: 57)
WRN8 : ggguuucuaucuuacuaaaTT (SEQ ID NO: 58)
WRN9 : gauuaguaguuacaugguaTT (SEQ ID NO: 59)
WRN10 : gccuguuauuucggcacaaTT (SEQ ID NO: 60)
WRN11 : cucuguuggaagucaucaaTT (SEQ ID NO: 61)
WRN12 : gaaguuucucgguauaacaTT (SEQ ID NO: 62)

BLM1 : cgucacucagccagaacacTT (SEQ ID NO: 3)
BLM2 : gaguaagcacugcucagaaTT (THIS SEQUENCE WAS USED IN ALL EXPERIMENTS) (SEQ ID NO: 63)
BLM3 : gaugcucaggaaagugacuTT (SEQ ID NO: 64)
BLM4 : gagucaauucagaauuauaTT (SEQ ID NO: 65)
BLM5 : caaggaaugagaaauauaaTT (SEQ ID NO: 66)
BLM6 : gaaucucaauguacauagaTT (SEQ ID NO: 67)
BLM7 : cgcuagacagauaaguuuaTT (SEQ ID NO: 68)
BLM8 : gguggcauuugauugccuaTT (SEQ ID NO: 69)

FIG. 3

| siRNA SEQUENCE | GENE EXPRESSION AMOUNT |
|---|---|
| NS | 100% |
| RecQ1-2 (SEQ ID NO: 31) | 3% |
| RecQ1-3 (SEQ ID NO: 32) | 7% |
| RecQ1-4 (SEQ ID NO: 33) | 8% |
| RecQ1-5 (SEQ ID NO: 34) | 7% |
| RecQ1-6 (SEQ ID NO: 43) | 3% |
| RecQ1-7 (SEQ ID NO: 44) | 4% |
| RecQ1-8 (SEQ ID NO: 45) | 4% |
| RecQ1-9 (SEQ ID NO: 46) | 2% |
| RecQ1-10 (SEQ ID NO: 47) | 6% |
| RecQ1-11 (SEQ ID NO: 48) | 2% |
| RecQ1-12 (SEQ ID NO: 49) | 2% |
| RecQ1-13 (SEQ ID NO: 50) | 8% |
| RecQ1-14 (SEQ ID NO: 51) | 5% |
| RecQ1-15 (SEQ ID NO: 52) | 7% |
| WRN2 (SEQ ID NO: 35) | 11% |
| WRN3 (SEQ ID NO: 53) | 10% |
| WRN4 (SEQ ID NO: 54) | 8% |
| WRN5 (SEQ ID NO: 55) | 18% |
| WRN6 (SEQ ID NO: 56) | 7% |
| WRN7 (SEQ ID NO: 57) | 11% |
| WRN8 (SEQ ID NO: 58) | 14% |
| WRN9 (SEQ ID NO: 59) | 28% |
| WRN10 ( 60) | 30% |
| WRN11 (SEQ ID NO: 61) | 30% |
| WRN12 (SEQ ID NO: 62) | 8% |
| BLM2 (SEQ ID NO: 63) | 15% |
| BLM3 (SEQ ID NO: 64) | 12% |
| BLM4 (SEQ ID NO: 65) | 10% |
| BLM5 (SEQ ID NO: 66) | 19% |
| BLM6 (SEQ ID NO: 67) | 24% |
| BLM7 (SEQ ID NO: 68) | 20% |
| BLM8 (SEQ ID NO: 69) | 24% |

FIG. 6

| siRNA SEQUENCE | VIABILITY |
|---|---|
| NS | 100% |
| RecQ1-2 (SEQ ID NO: 31) | 39% |
| RecQ1-3 (SEQ ID NO: 32) | 49% |
| RecQ1-4 (SEQ ID NO: 33) | 52% |
| RecQ1-5 (SEQ ID NO: 34) | 63% |
| RecQ1-9 (SEQ ID NO: 46) | 20% |
| RecQ1-11 (SEQ ID NO: 48) | 75% |
| RecQ1-12 (SEQ ID NO: 49) | 57% |
| RecQ1-13 (SEQ ID NO: 50) | 37% |
| RecQ1-15 (SEQ ID NO: 52) | 42% |
| WRN2 (SEQ ID NO: 35) | 11% |
| WRN4 (SEQ ID NO: 54) | 5% |
| WRN5 (SEQ ID NO: 55) | 9% |
| WRN6 (SEQ ID NO: 56) | 10% |
| WRN9 (SEQ ID NO: 59) | 67% |
| WRN10 (SEQ ID NO: 60) | 40% |
| BLM2 (SEQ ID NO: 63) | 7% |
| BLM3 (SEQ ID NO: 64) | 15% |

FIG. 9

SEQUENCE LISTING

```
<160> NUMBER OF SEQ ID NOS: 74

<210> SEQ ID NO 1
<211> LENGTH: 21
<212> TYPE: DNA
<213> ORGANISM: Artificial Sequence
<220> FEATURE:
<223> OTHER INFORMATION: an artificially synthesized DNA/RNA hybrid
      sequence

<400> SEQUENCE: 1

guucagacca cuucagcuut t                                              21


<210> SEQ ID NO 2
<211> LENGTH: 21
<212> TYPE: DNA
<213> ORGANISM: Artificial Sequence
<220> FEATURE:
<223> OTHER INFORMATION: an artificially synthesized DNA/RNA hybrid
      sequence

<400> SEQUENCE: 2

guucuuguca cguccucugt t                                              21


<210> SEQ ID NO 3
<211> LENGTH: 21
<212> TYPE: DNA
<213> ORGANISM: Artificial Sequence
<220> FEATURE:
<223> OTHER INFORMATION: an artificially synthesized DNA/RNA hybrid
      sequence

<400> SEQUENCE: 3

cgucacucag ccagaacact t                                              21


<210> SEQ ID NO 4
<211> LENGTH: 21
<212> TYPE: DNA
<213> ORGANISM: Artificial Sequence
<220> FEATURE:
<223> OTHER INFORMATION: an artificially synthesized DNA/RNA hybrid
      sequence

<400> SEQUENCE: 4

gcuucgagag cuacgugcat t                                              21


<210> SEQ ID NO 5
<211> LENGTH: 21
<212> TYPE: DNA
<213> ORGANISM: Artificial Sequence
<220> FEATURE:
<223> OTHER INFORMATION: an artificially synthesized DNA/RNA hybrid
      sequence
```

<400> SEQUENCE: 5
gguaacaagg acgucuuugt t 21

<210> SEQ ID NO 6
<211> LENGTH: 2866
<212> TYPE: DNA
<213> ORGANISM: Homo sapiens

<400> SEQUENCE: 6
gagtagcgga aagatctgct cgaggcctgg gtgctttggt gtcggagatc cgagagtcgg 60
agatcggaga gtcggacaca ggacagtcgg acaccggaca gtcaaacacc ggagagttag 120
actgggcttc tcggtgggga gaggctctgg gataactact gttacagctt tgaagggtca 180
agggtgtgcg ctttttgttt catccttccc tttcctgctg cagggcgagg ccggtctgta 240
gcggatcact tcctttcgcc cacacattgg cggaggagaa accggaaagt taatcactgc 300
cctgctctga gaactcgggc ctttaggggc acgttcgcct gctgaccggt cttctgatct 360
ccccattctt ttccatgcag gaggattggc caccaaagcc tgtttattag cagctgccat 420
ttgttgaaag aaatttggat tattttagaa acaaatttgg aaagaaaaag aatggcgtcc 480
gtttcagctc taactgagga actggattct ataaccagtg agctacatgc agtagaaatt 540
caaattcaag aacttacgga aaggcaacaa gagcttattc agaaaaaaaa agtcctgaca 600
aagaaaataa agcagtgttt agaggattct gatgccgggg caagcaatga atatgattct 660
tcacctgccg cttggaataa agaagatttt ccatggtctg gtaaagttaa agatattctg 720
caaaatgtct ttaaactgga aaagttcaga ccacttcagc ttgaaactat taacgtaaca 780
atggctggaa aggaggtatt tcttgttatg cctacaggag gtggaaagag cttatgttac 840
cagttaccag cattatgttc agatggtttt acactcgtca tttgcccatt gatctctctt 900
atggaagacc aattaatggt ttaaaaacaa ttaggaattt cagcaaccat gttaaatgct 960
tctagttcta aggagcatgt taaatgggtt catgctgaaa tggtaaataa aaactccgag 1020
ttaaagctga tttatgtgac tccagagaaa attgcaaaaa gcaaaatgtt tatgtcaaga 1080
ctagagaaag cctatgaagc aaggagattt actcgaattg ctgtggatga agttcactgc 1140
tgtagtcagt ggggacatga tttcagacct gattataagg cacttggtat cttaaagcgg 1200
cagttcccta acgcatcact aattgggctg actgcaactg caacaaatca cgttttgacg 1260
gatgctcaga aaattttgtg cattgaaaag tgttttactt ttacagcttc ttttaatagg 1320
ccaaatctat attatgaggt tcggcagaag ccctcaaaca ctgaagattt tattgaggat 1380
attgtaaagc tcattaatgg gagatacaaa gggcaatcag gaatcatata ttgtttttct 1440
cagaaagact ctgaacaagt tacggttagt ttgcagaatc tgggaattca tgcaggtgct 1500
taccatgcca atttggagcc agaagataag accacagttc atagaaaatg gtcagccaat 1560
gaaattcagg tagtagtggc aactgttgca tttggtatgg gaattgataa gccagatgtg 1620
aggtttgtta tccatcattc aatgagtaaa tccatggaaa attattacca agagagtgga 1680
cgtgcaggtc gagatgacat gaaagcagac tgtattttgt actacggctt tggagatata 1740
ttcagaataa gttcaatggt ggtgatggaa aatgtgggac agcagaagct ttatgagatg 1800
gtatcatact gtcaaaacat aagcaaatgt cgtcgtgtgt tgatggctca acattttgat 1860
gaagtatgga actcagaagc atgtaacaaa atgtgcgata actgctgtaa agacagtgca 1920
tttgaaagaa agaacataac agagtactgc agagatctaa tcaagatcct gaagcaggca 1980
gaggaactga atgaaaaact cactccattg aaactgattg attcttggat gggaaagggt 2040

-continued gcagcaaaac tgagagtagc aggtgttgtg gctcccacac ttcctcgtga agatctggag 2100
aagattattg cacactttct aatacagcag tatcttaaag aagactacag ttttacagct 2160
tatgctacca tttcgtattt gaaaatagga cctaaagcta accttctgaa caatgaggca 2220
catgctatta ctatgcaagt gacaaagtcc acgcagaact ctttcagggc tgaatcgtct 2280
caaacttgtc attctgaaca aggtgataaa aagatggagg aaaaaaattc aggcaacttc 2340
cagaagaagg ctgcaaacat gcttcagcag tctggttcta agaatacagg agctaagaaa 2400
agaaaaatcg atgatgcctg atatgaatgt tactaaattt tctaattaaa gatggtttat 2460
gcatgtatat gccattattt ttgtagttag acaatagttt ttaaaagaat ttcatagata 2520
ttttatatgt atggatctat attttcagag cttatctctg aagatctaaa cttttgagaa 2580
tgtttgaaaa ttagagatca tgaattatat aattttccag tataaaacaa gggaaaaatt 2640
tttatgtaaa accctttaaa tgtaaaatat ttgagaataa gttcatacaa tcgtcttaag 2700 tttttatgc ctttatatac ttagctatat tttttctttt gacataacta tctttttgaa 2760
agcaatatta tactgacaga ggctcactga gtgatacttt aagttaaata tgtagatcaa 2820
gggatgtcca atcttttggc ttccctgagc cagcgaattg tgcaca 2866

<210> SEQ ID NO 7
<211> LENGTH: 2286
<212> TYPE: DNA
<213> ORGANISM: Homo sapiens

<400> SEQUENCE: 7
gagtagcgga aagatctgct cgaggcctgg gtgctttggt gtcggagatc cgagagtcgg 60
agatcggaga gtcggacaca ggacagtcgg acaccggaca gtcaaacacc ggagagttag 120
actgggcttc tcggtgggga gaggctctgg gataactact gttacagctt tgaagggtca 180
agggaggatt ggccaccaaa gcctgtttat tagcagctgc catttgttga aagaaatttg 240
gattatttta gaaacaaatt tggaaagaaa aagaatggcg tccgtttcag ctctaactga 300
ggaactggat tctataacca gtgagctaca tgcagtagaa attcaaattc aagaacttac 360
ggaaaggcaa caagagctta ttcagaaaaa aaaagtcctg acaaagaaaa taaagcagtg 420
tttagaggat tctgatgccg gggcaagcaa tgaatatgat tcttcacctg ccgcttggaa 480
taaagaagat tttccatggt ctggtaaagt taaagatatt ctgcaaaatg tctttaaact 540
ggaaaagttc agaccacttc agcttgaaac tattaacgta acaatggctg gaaaggaggt 600
atttcttgtt atgcctacag gaggtggaaa gagcttatgt taccagttac cagcattatg 660
ttcagatggt tttacactcg tcatttgccc attgatctct cttatggaag accaattaat 720
ggttttaaaa caattaggaa tttcagcaac catgttaaat gcttctagtt ctaaggagca 780
tgttaaatgg gttcatgctg aaatggtaaa taaaaactcc gagttaaagc tgatttatgt 840
gactccagag aaaattgcaa aaagcaaaat gtttatgtca agactagaga aagcctatga 900
agcaaggaga tttactcgaa ttgctgtgga tgaagttcac tgctgtagtc agtggggaca 960
tgatttcaga cctgattata aggcacttgg tatcttaaag cggcagttcc ctaacgcatc 1020
actaattggg ctgactgcaa ctgcaacaaa tcacgttttg acggatgctc agaaaatttt 1080
gtgcattgaa aagtgtttta cttttacagc ttcttttaat aggccaaatc tatattatga 1140
ggttcggcag aagccctcaa acactgaaga ttttattgag gatattgtaa agctcattaa 1200
tgggagatac aaagggcaat caggaatcat atattgtttt tctcagaaag actctgaaca 1260
agttacggtt agtttgcaga atctgggaat tcatgcaggt gcttaccatg ccaatttgga 1320

-continued gccagaagat aagaccacag ttcatagaaa atggtcagcc aatgaaattc aggtagtagt 1380
ggcaactgtt gcatttggta tgggaattga taagccagat gtgaggtttg ttatccatca 1440
ttcaatgagt aaatccatgg aaaattatta ccaagagagt ggacgtgcag gtcgagatga 1500
catgaaagca gactgtattt tgtactacgg ctttggagat atattcagaa taagttcaat 1560
ggtggtgatg gaaaatgtgg gacagcagaa gctttatgag atggtatcat actgtcaaaa 1620
cataagcaaa tgtcgtcgtg tgttgatggc tcaacatttt gatgaagtat ggaactcaga 1680
agcatgtaac aaaatgtgcg ataactgctg taaagacagt gcatttgaaa gaaagaacat 1740
aacagagtac tgcagagatc taatcaagat cctgaagcag gcagaggaac tgaatgaaaa 1800
actcactcca ttgaaactga ttgattcttg gatgggaaag ggtgcagcaa aactgagagt 1860
agcaggtgtt gtggctccca cacttcctcg tgaagatctg gagaagatta ttgcacactt 1920
tctaatacag cagtatctta aagaagacta cagttttaca gcttatgcta ccatttcgta 1980
tttgaaaata ggacctaaag ctaaccttct gaacaatgag gcacatgcta ttactatgca 2040
agtgacaaag tccacgcaga actctttcag ggctgaatcg tctcaaactt gtcattctga 2100
acaaggtgat aaaaagatgg aggaaaaaaa ttcaggcaac ttccagaaga aggctgcaaa 2160
catgcttcag cagtctggtt ctaagaatac aggagctaag aaaagaaaaa tcgatgatgc 2220
ctgatatgaa tgttactaaa ttttctaatt aaagatggtt tatgcaaaaa aaaaaaaaaa 2280
aaaaaa 2286

<210> SEQ ID NO 8
<211> LENGTH: 2251
<212> TYPE: DNA
<213> ORGANISM: Homo sapiens

<400> SEQUENCE: 8
ggcacgaggg agatccgaga gtcggagatc ggagagtcgg acacaggaca gtcggacacc 60
ggacagtcaa acaccggaga gttagactgg gcttctcggt ggggagaggc tctgggataa 120
ctactgttac agctttgaag ggtcaaggga ggattggcca ccaaagcctg tttattagca 180
gctgccattt gttgaaagaa atttggatta ttttagaaac aaatttggaa agaaaaagaa 240
tggcgtccgt ttcagctcta actgaggaac tggattctat aaccagtgag ctacatgcag 300
tagaaattca aattcaagaa cttacggaaa ggcaacaaga gcttattcag aaaaaaaaag 360
tcctgacaaa gaaaataaag cagtgtttag aggattctga tgccggggca agcaatgaat 420
atgattcttc acctgccgct tggaataaag aagattttcc atggtctggt aaagttaaag 480
atattctgca aaatgtcttt aaactggaaa agttcagacc acttcagctt gaaactatta 540
acgtaacaat ggctggaaag gaggtatttc ttgttatgcc tacaggaggt ggaaagagct 600
tatgttacca gttaccagca ttatgttcag atggttttac actcgtcatt tgcccattga 660
tctctcttat ggaagaccaa ttaatggttt taaaacaatt aggaatttca gcaaccatgt 720
taaatgcttc tagttctaag gagcatgtta aatgggttca tgctgaaatg gtaaataaaa 780
actccgagtt aaagctgatt tatgtgactc cagagaaaat tgcaaaaagc aaaatgttta 840
tgtcaagact agagaaagcc tatgaagcaa ggagatttac tcgaattgct gtggatgaag 900
ttcactgctg tagtcagtgg ggacatgatt tcagacctga ttataaggca cttggtatct 960
taaagcggca gttccctaac gcatcactaa ttgggctgac tgcaactgca acaaatcacg 1020
ttttgacgga tgctcagaaa attttgtgca ttgaaaagtg ttttactttt acagcttctt 1080
ttaataggcc aaatctatat tatgaggttc ggcagaagcc ctcaaacact gaagatttta 1140

-continued

```
ttgaggatat tgtaaagctc attaatggga gatacaaagg gcaatcagga atcatatatt   1200

gtttttctca gaaagactct gaacaagtta cggttagttt gcagaatctg ggaattcatg   1260

caggtgctta ccatgccaat ttggagccag aagataagac cacagttcat agaaaatggt   1320

cagccaatga aattcaggta gtagtggcaa ctgttgcatt tggtatggga attgataagc   1380

cagatgtgag gtttgttatc catcattcaa tgagtaaatc catggaaaat tattaccaag   1440

agagtggacg tgcaggtcga gatgacatga aagcagactg tattttgtac tacggctttg   1500

gagatatatt cagaataagt tcaatggtgg tgatggaaaa tgtgggacag cagaagcttt   1560

atgagatggt atcatactgt caaaacataa gcaaatgtcg tcgtgtgttg atggctcaac   1620

attttgatga agtatggaac tcagaagcat gtaacaaaat gtgcgataac tgctgtaaag   1680

acagtgcatt tgaaagaaag aacataacag agtactgcag agatctaatc aagatcctga   1740

agcaggcaga ggaactgaat gaaaaactca ctccattgaa actgattgat tcttggatgg   1800

gaaagggtgc agcaaaactg agagtagcag gtgttgtggc tcccacactt cctcgtgaag   1860

atctggagaa gattattgca cactttctaa tacagcagta tcttaaagaa gactacagtt   1920

ttacagctta tgctaccatt tcgtatttga aaataggacc taaagctaac cttctgaaca   1980

atgaggcaca tgctattact atgcaagtga caaagtccac gcagaactct ttcagggctg   2040

aatcgtctca aacttgtcat tctgaacaag gtgataaaaa gatggagaaa aaaaattcag   2100

gcaacttcca gaagaaggct gcaaacatgc ttcagcagtc tggttctaag aatacaggag   2160

ctaagaaaag aaaaatcgat gatgcctgat atgaatgtta ctaaattttc taattaaaga   2220

tggtttatgc aaaaaaaaaa aaaaaaaaaa a                                  2251
```

<210> SEQ ID NO 9
<211> LENGTH: 2449
<212> TYPE: DNA
<213> ORGANISM: Homo sapiens

<400> SEQUENCE: 9

```
tcggcgtccg tttcagctct aactgaggaa ctggattcta taaccagtga gctacatgca     60

gtagaaattc aaattcaaga acttacggaa aggcaacaag agcttattca gaaaaaaaaa    120

gtcctgacaa agaaaataaa gcagtgttta gaggattctg atgccggggc aagcaatgaa    180

tatgattctt cacctgccgc ttggaataaa gaagattttc catggtctgg taaagttaaa    240

gatattctgc aaaatgtctt taaactggaa aagttcagac cacttcagct tgaaactatt    300

aacgtaacaa tggctggaaa ggaggtattt cttgttatgc ctacaggagg tggaaagagc    360

ttatgttacc agttaccagc attatgttca gatggtttta cactcgtcat ttgcccattg    420

atctctctta tggaagacca attaatggtt ttaaaacaat taggaatttc agcaaccatg    480

ttaaatgctt ctagttctaa ggagcatgtt aaatgggttc atgctgaaat ggtaaataaa    540

aactccgagt taaagctgat ttatgtgact ccagagaaaa ttgcaaaaag caaaatgttt    600

atgtcaagac tagagaaagc ctatgaagca aggagattta ctcgaattgc tgtggatgaa    660

gttcactgct gtagtcagtg gggacatgat ttcagacctg attataaggc acttggtatc    720

ttaaagcggc agttccctaa cgcatcacta attgggctga ctgcaactgc aacaaatcac    780

gttttgacgg atgctcagaa aattttgtgc attgaaaagt gttttacttt tacagcttct    840

tttaataggc caaatctata ttatgaggtt cggcagaagc cctcaaacac tgaagatttt    900

attgaggata ttgtaaagct cattaatggg agatacaaag ggcaatcagg aatcatatat    960

tgtttttctc agaaagactc tgaacaagtt acggttagtt tgcagaatct gggaattcat   1020
```

```
gcaggtgctt accatgccaa tttggagcca gaagataaga ccacagttca tagaaaatgg   1080
tcagccaatg aaattcaggt agtagtggca actgttgcat ttggtatggg aattgataag   1140
ccagatgtga ggtttgttat ccatcattca atgagtaaat ccatggaaaa ttattaccaa   1200
gagagtggac gtgcaggtcg agatgacatg aaagcagact gtattttgta ctacggcttt   1260
ggagatatat tcagaataag ttcaatggtg gtgatggaaa atgtgggaca gcagaagctt   1320
tatgagatgg tatcatactg tcaaaacata agcaaatgtc gtcgtgtgtt gatggctcaa   1380
cattttgatg aagtatggaa ctcagaagca tgtaacaaaa tgtgcgataa ctgctgtaaa   1440
gacagtgcat ttgaaagaaa gaacataaca gagtactgca gagatctaat caagatcctg   1500
aagcaggcag aggaactgaa tgaaaaactc actccattga aactgattga ttcttggatg   1560
ggaaagggtg cagcaaaact gagagtagca ggtgttgtgg ctcccacact tcctcgtgaa   1620
gatctggaga agattattgc acactttcta atacagcagt atcttaaaga agactacagt   1680
tttacagctt atgctaccat ttcgtatttg aaaataggac ctaaagctaa tcttctgaac   1740
aatgaggcac atgctattac tatgcaagtg acaaagtcca cgcagaactc tttcagggct   1800
gaatcgtctc aaacttgtca ttctgaacaa ggtgataaaa agatggagga aaaaaattca   1860
ggcaacttcc agaagaaggc tgcaaacatg cttcagcaat ctggttctaa gaatacagga   1920
gctaagaaaa gaaaaatcga tgatgcctga tatgactgtt actaaatttt ctaattaaag   1980
atggtttatg catgtatatg ccattatttt tgtagttaga caatagtttt taaaagaatt   2040
tcatagatat tttatatgta tggatctata ttttcagagc ttatctctga agatctaaac   2100
ttttggagaa tgtttggaaa attagagatc atgaattata taattttcca gtataaaaca   2160
agggaaaaat ttttatgtaa aaccctttaa atgtaaaata tttgagaata agttcataca   2220
atcgtcttaa gtttttttatg cctttatata cttagctata tttttctttt tgacataacc   2280
atctttttga aagcaatatt atactgacag aggttcactg agtgatactt taagttaaat   2340
atgtagatca gggatgtcca atcttttggc ttccctgagc cacattggaa gaagaattgt   2400
cttgggccgc acataaaata tgctaacact gacgatagct gatgagctt              2449
```

<210> SEQ ID NO 10
<211> LENGTH: 2925
<212> TYPE: DNA
<213> ORGANISM: Homo sapiens

<400> SEQUENCE: 10

```
cttttttttt tttttttttt tttttataag attattagta taaaatttta gataggtagg     60
agtagcgaaa agatctgctc gaggcctggg tgctttggtg tcggagatcc gagagtcgga    120
gatcggagag tcggacacag gacagtcgga caccggacag tcaaacaccg gagagttaga    180
ctgggcttct cggtggggac aggctctggg ataactactg ttacagcttt gaagggtcaa    240
gggtgtgcgc tttttctttc atccttccct ttcctgctgc aggcgaggcc ggtctgatgc    300
ggatcacttc ctttcgccca cacattggcg gaggagaaac cggaaagtta atcactgccc    360
tgctctgaga actcgggcct ttaggggcac gttcgcctgc tgaccggtct tctgatctcc    420
ccattctttt ccatgcagga ggattggcca ccaaagcctg tttattagca gctgccattt    480
gttaaagaaa tttggattat tttagaaaca atttggaaag aaaaagaatg gcgtccgttt    540
cagctctaac tgaggaactg gattctataa ccagtgagct acatgcagta gaaattcaaa    600
ttcaagaact tacggaaagg caacaagagc ttattcagaa aaaaaaagtc ctgacaaaga    660
aaataaagca gtgtttagag gattctgatg ccggggcaag caatgaatat gattcttcac    720
```

-continued

```
ctgccgcttg gaataaagaa gattttccat ggtctggtaa agttaaagat attctgcaaa    780
atgtctttaa actggaaaag ttcagaccac ttcagcttga aactattaac gtaacaatgg    840
ctggaaagga ggtatttctt gttatgccta caggaggtgg aaagagctta tgttaccagt    900
taccagcatt atgttcagat ggttttacac tcgtcatttg cccattgatc tctcttatgg    960
aagaccaatt aatggtttta aaacaattag gaatttcagc aaccatgtta aatgcttcta   1020
gttctaagga gcatgttaaa tgggttcatg atgaaatggt aaataaaaac tccgagttaa   1080
agctgattta tgtgactcca gagaaaattg caaaaagcaa aatgtttatg tcaagactag   1140
agaaagccta tgaagcaagg agatttactc gaattgctgt ggatgaagtt cactgctgta   1200
gtcagtgggg acatgatttc agacctgatt ataaggcact tggtatctta aagcggcagt   1260
tccctaacgc atcactaatt gggctgactg caactgcaac aaatcacgtt ttgacggatg   1320
ctcagaaaat tttgtgcatt gaaaagtgtt ttacttttac agcttctttt aataggccaa   1380
atctatatta tgaggttcgg cagaagccct caaacactga agattttatt gaggatattg   1440
taaagctcat taatgggaga tacaaagggc aatcaggaat catatattgt tttctcaga    1500
aagactctga acaagttacg gttagtttgc agaatctggg aattcatgca ggtgcttacc   1560
atgccaattt ggagccagaa gataagacca cagttcatag aaaatggtca gccaatgaaa   1620
ttcaggtagt agtggcaact gttgcatttg gtatgggaat tgataagcca gatgtgaggt   1680
ttgttatcca tcattcaatg agtaaatcca tggaaaatta ttaccaagag agtggacgtg   1740
caggtcgaga tgacatgaaa gcagactgta ttttgtacta cggctttgga gatatattca   1800
gaataagttc aatggtggtg atggaaaatg tgggacagca gaagctttat gagatggtat   1860
catactgtca aaacataagc aaatctcgtc gtgtgttgat ggctcaacat tttgatgaag   1920
tatggaactc agaagcatgt aacaaaatgt gcgataactg ctgtaaagac agtgcatttg   1980
aaagaacgaa cataacagag tactgcagag atctaatcaa gatcctgaag caggcagagg   2040
aactgaatga aaaactcact ccattgaaac tgattgattc ttggatggga aagggtgcag   2100
caaaactgag agtagcaggt gttgtggctc ccacacttcc tcgtgaagat ctggagaaga   2160
ttattgcaca ctttctaata cagcagtatc ttaaagaaga ctacagtttt acagcttatg   2220
ctgccatttc gtatttgaaa ataggaccta aagctaatct tctgaacaat gaggcacatg   2280
ctattactat gcaagtgaca aagtccacgc agaactcttt cagggctgaa tcgtctcaaa   2340
cttgtcattc tgaacaaggt gataaaaaga atggaggaaa aaaaattcag gcaacttcca   2400
gaagaaggct gcaaacatgc ttcagcaatc tggttctaag aatacaggag ctaagaaaag   2460
aaaaatcgat gatgcctgat atgaatgtta ctaaattttc taattaaaga tggtttatgc   2520
atgtatatgc cattattttt gtagttagac aatagttttt aaaagaattt catagatatt   2580
ttatatgtat ggatctatat tttcagagct tatctctgaa gatctaaact tttgagaatg   2640
tttgaaaatt agagatcatg aattatataa ttttccagtg taaaacaagg gaaaaatttt   2700
tatgtaaaac cctttaaatg taaaatattt gagaataagt tcatacaatc gtcttaagtt   2760
ttttatgcct ttatatactt agctatattt tttcttttga cataactatc tttttgaaag   2820
caatattata ctgacagagg cttcactgag tgatacttta agttaaatat gtagatcaag   2880
ggatgtccaa tcttttggct tccctgagcc agcgaattgt gcaca                   2925
```

<210> SEQ ID NO 11
<211> LENGTH: 5765
<212> TYPE: DNA
<213> ORGANISM: Homo sapiens

<400> SEQUENCE: 11

```
cagccgcccc tcctgcggcc gctgcggggg ccgccgcctg acttcggaca ccggccccgc      60
acccgccagg aggggaggga aggggaggcg gggagagcga cggcgggggg cgggcggtgg     120
accccgcctc ccccggcaca gcctgctgag gggaagaggg ggtctccgct cttcctcagt     180
gcactctctg actgaagccc ggcgcgtggg gtgcagcggg agtgcgaggg gactggacag     240
gtgggaagat gggaatgagg accgggcggc gggaatgttc tcacttctcc ggattccacc     300
gggatgcagg actctagctg cccagccgca cctgcgaaga gactacactt cccgaggtgc     360
tcagcggcag cgagggcctc cacgcatgcg caccgcggcg cgctgggcgg ggctggatgg     420
gctgtggtgg gagggttgca gcgccgcgag aaaggcgagc cgggccgggg gcggggaaag     480
gggtggggca ggaacggggg cggggacggc gctggagggg cgggtcgggt aggtctcccg     540
gagctgatgt gtactgtgtg cgccggggag gcgccggctt gtactcggca gcgcgggaat     600
aaagtttgct gatttggtgt ctagcctgga tgcctgggtt gcaggccctg cttgtggtgg     660
cgctccacag tcatccggct gaagaagacc tgttggactg gatcttctcg ggttttcttt     720
cagatattgt tttgtattta cccatgaaga cattgttttt tggactctgc aaataggaca     780
tttcaaagat gagtgaaaaa aaattggaaa caactgcaca gcagcggaaa tgtcctgaat     840
ggatgaatgt gcagaataaa agatgtgctg tagaagaaag aaaggcatgt gttcggaaga     900
gtgtttttga agatgacctc cccttcttag aattcactgg atccattgtg tatagttacg     960
atgctagtga ttgctctttc ctgtcagaag atattagcat gagtctatca gatggggatg    1020
tggtgggatt tgacatggag tggccaccat tatacaatag agggaaactt ggcaaagttg    1080
cactaattca gttgtgtgtt tctgagagca aatgttactt gttccacgtt tcttccatgt    1140
cagtttttcc ccagggatta aaaatgttgc ttgaaaataa agcagttaaa aaggcaggtg    1200
taggaattga aggagatcag tggaaacttc tacgtgactt tgatatcaaa ttgaagaatt    1260
ttgtggagtt gacagatgtt gccaataaaa agctgaaatg tacagagacc tggagcctta    1320
acagtctggt taaacacctc ttaggtaaac agctcctgaa agacaagtct atccgctgta    1380
gcaattggag taaatttcct ctcactgagg accagaaact gtatgcagcc actgatgctt    1440
atgctggttt tattatttac cgaaatttag agattttgga tgatactgtg caaaggtttg    1500
ctataaataa agaggaagaa atcctactta gcgacatgaa caaacagttg acttcaatct    1560
ctgaggaagt gatggatctg gctaagcatc ttcctcatgc tttcagtaaa ttggaaaacc    1620
cacggagggt ttctatctta ctaaaggata tttcagaaaa tctatattca ctgaggagga    1680
tgataattgg gtctactaac attgagactg aactgaggcc cagcaataat ttaaacttat    1740
tatcctttga agattcaact actgggggag tacaacagaa acaaattaga gaacatgaag    1800
ttttaattca cgttgaagat gaaacatggg acccaacact tgatcattta gctaaacatg    1860
atggagaaga tgtacttgga aataaagtgg aacgaaaaga agatggattt gaagatggag    1920
tagaagacaa caaattgaaa gagaatatgg aaagagcttg tttgatgtcg ttagatatta    1980
cagaacatga actccaaatt ttggaacagc agtctcagga agaatatctt agtgatattg    2040
cttataaatc tactgagcat ttatctccca atgataatga aaacgatacg tcctatgtaa    2100
ttgagagtga tgaagattta gaaatggaga tgcttaagca tttatctccc aatgataatg    2160
aaaacgatac gtcctatgta attgagagtg atgaagattt agaaatggag atgcttaagt    2220
ctttagaaaa cctcaatagt ggcacggtag aaccaactca ttctaaatgc ttaaaaatgg    2280
aaagaaatct gggtcttcct actaaagaag aagaagaaga tgatgaaaat gaagctaatg    2340
```

-continued

```
aaggggaaga agatgatgat aaggactttt tgtggccagc acccaatgaa gagcaagtta   2400
cttgcctcaa gatgtacttt ggccattcca gttttaaacc agttcagtgg aaagtgattc   2460
attcagtatt agaagaaaga agagataatg ttgctgtcat ggcaactgga tatggaaaga   2520
gtttgtgctt ccagtatcca cctgtttatg taggcaagat tggccttgtt atctctcccc   2580
ttatttctct gatggaagac caagtgctac agcttaaaat gtccaacatc ccagcttgct   2640
tccttggatc agcacagtca gaaaatgttc taacagatat taaattaggt aaataccgga   2700
ttgtatacgt aactccagaa tactgttcag gtaacatggg cctgctccag caacttgagg   2760
ctgatattgg tatcacgctc attgctgtgg atgaggctca ctgtatttct gagtgggggc   2820
atgattttag ggattcattc aggaagttgg gctccctaaa gacagcactg ccaatggttc   2880
caatcgttgc acttactgct actgcaagtt cttcaatccg ggaagacatt gtacgttgct   2940
taaatctgag aaatcctcag atcacctgta ctggttttga tcgaccaaac ctgtatttag   3000
aagttaggcg aaaaacaggg aatatccttc aggatctgca gccatttctt gtcaaaacaa   3060
gttcccactg ggaatttgaa ggtccaacaa tcatctactg tccttctaga aaaatgacac   3120
aacaagttac aggtgaactt aggaaactta atctatcctg tggaacatac catgcgggca   3180
tgagttttag cacaaggaaa gacattcatc ataggtttgt aagagatgaa attcagtgtg   3240
tcatagctac catagctttt ggaatgggca ttaataaagc tgacattcgc caagtcattc   3300
attacggtgc tcctaaggac atggaatcat attatcagga gattggtaga gctggtcgtg   3360
atggacttca aagttcttgt cacgtcctct gggctcctgc agacattaac ttaaataggc   3420
accttcttac tgagatacgt aatgagaagt ttcgattata caaattaaag atgatggcaa   3480
agatggaaaa atatcttcat tctagcagat gtaggagaca aatcatcttg tctcattttg   3540
aggacaaaca agtacaaaaa gcctccttgg gaattatggg aactgaaaaa tgctgtgata   3600
attgcaggtc cagattggat cattgctatt ccatggatga ctcagaggat acatcctggg   3660
actttggtcc acaagcattt aagcttttgt ctgctgtgga catcttaggc gaaaaatttg   3720
gaattgggct tccaatttta tttctccgag gatctaattc tcagcgtctt gccgatcaat   3780
atcgcaggca cagtttattt ggcactggca aggatcaaac agagagttgg tggaaggctt   3840
tttcccgtca gctgatcact gagggattct tggtagaagt ttctcggtat aacaaattta   3900
tgaagatttg cgcccttacg aaaaagggta gaaattggct tcataaagct aatacagaat   3960
ctcagagcct catccttcaa gctaatgaag aattgtgtcc aaagaagttt cttctgccta   4020
gttcgaaaac tgtatcttcg ggcaccaaag agcattgtta taatcaagta ccagttgaat   4080
taagtacaga gaagaagtct aacttggaga agttatattc ttataaacca tgtgataaga   4140
tttcttctgg gagtaacatt tctaaaaaaa gtatcatggt acagtcacca gaaaaagctt   4200
acagttcctc acagcctgtt atttcggcac aagagcagga gactcagatt gtgttatatg   4260
gcaaattggt agaagctagg cagaaacatg ccaataaaat ggatgttccc ccagctattc   4320
tggcaacaaa caagatactg gtggatatgg ccaaaatgag accaactacg gttgaaaacg   4380
taaaaaggat tgatggtgtt tctgaaggca aagctgccat gttggcccct ctgttggaag   4440
tcatcaaaca tttctgccaa acaaatagtg ttcagacaga cctcttttca agtacaaaac   4500
ctcaagaaga acagaagacg agtctggtag caaaaaataa aatatgcaca ctttcacagt   4560
ctatggccat cacatactct ttattccaag aaaagaagat gcctttgaag agcatagctg   4620
agagcaggat tctgcctctc atgacaattg gcatgcactt atcccaagcg gtgaaagctg   4680
gctgccccct tgatttggag cgagcaggcc tgactccaga ggttcagaag attattgctg   4740
```

-continued atgttatccg aaaccctccc gtcaactcag atatgagtaa aattagccta atcagaatgt 4800
tagttcctga aaacattgac acgtacctta tccacatggc aattgagatc cttaaacatg 4860
gtcctgacag cggacttcaa ccttcatgtg atgtcaacaa aaggagatgt tttcccggtt 4920
ctgaagagat ctgttcaagt tctaagagaa gcaaggaaga agtaggcatc aatactgaga 4980
cttcatctgc agagagaaag agacgattac ctgtgtggtt tgccaaagga agtgatacca 5040
gcaagaaatt aatggacaaa acgaaaaggg gaggtctttt tagttaagct ggcaattacc 5100
agaacaatta tgtttcttgc tgtattataa gaggatagct atattttatt tctgaagagt 5160
aaggagtagt attttggctt aaaaatcatt ctaattacaa agttcactgt ttattgaaga 5220
actggcatct taaatcagcc ttccgcaatt catgtagttt ctgggtcttc tgggagccta 5280
cgtgagtaca tcacctaaca gaatattaaa ttagacttcc tgtaagattg ctttaagaaa 5340
ctgttactgt cctgttttct aatctcttta ttaaaacagt gtatttggaa aatgttatgt 5400
gctctgattt gatatagata acagattagt agttacatgg taattatgtg atataaaata 5460
ttcatatatt atcaaaattc tgttttgtaa atgtaagaaa gcatagttat tttacaaatt 5520
gtttttactg tcttttgaag aagttcttaa atacgttgtt aaatggtatt agttgaccag 5580
ggcagtgaaa atgaaaccgc attttgggtg ccattaaata gggaaaaaac atgtaaaaaa 5640
tgtaaaatgg agaccaattg cactaggcaa gtgtatattt tgtattttat atacaatttc 5700
tattattttt caagtaataa aacaatgttt ttcatactga atattaaaaa aaaaaaaaaa 5760
aaaaa 5765

<210> SEQ ID NO 12
<211> LENGTH: 5208
<212> TYPE: DNA
<213> ORGANISM: Homo sapiens

<400> SEQUENCE: 12
tgtgcgccgg ggaggcgccg gcttgtactc ggcagcgcgg gaataaagtt tgctgatttg 60
gtgtctagcc tggatgcctg ggttgcaggc ctgcttgtgg tggcgctcca cagtcatccg 120
gctgaaggag acctgttgga ctggatcttc tcgggttttc tttcagatat tgttttgtat 180
ttacccatga agacattgtt ttttggactt tgcaaatagg acatttcaaa gatgagtgaa 240
aaaaaattgg aaacaactgc acagcagcgg aaatgtcctg aatggatgaa tgtgcagaat 300
aaaagatgtg ctgtagaaga aagaaaggca tgtgttcgga agagtgtttt tgaagatgac 360
ctccccttct tagaattcac tggatccatt gtgtatagtt acgatgctag tgattgctct 420
ttcctgtcag aagatattag catgagtcta tcagatgggg atgtggtggg atttgacatg 480
gagtggccac cattatacaa tagagggaaa cttggcaaag ttgcactaat tcagttgtgt 540
gtttctgaga gcaaatgtta cttgttccac gtttcttcca tgtcagtttt tccccaggga 600
ttaaaaatgt tgcttgaaaa taaagcagtt aaaaaggcag gtgtaggaat tgaaggagat 660
cagtggaaac ttctacgtga ctttgatatc aaattgaaga attttgtgga gttgacagat 720
gttgccaata aaaagctgaa atgtacagag acctggagcc ttaacagtct ggttaaacac 780
ctcttaggta aacagctcct gaaagacaag tctatccgct gtagcaattg gagtaaattt 840
cctctcactg aggaccagaa actgtatgca gccactgatg cttatgctgg ttttattatt 900
taccgaaatt tagagatttt ggatgatact gtgcaaaggt ttgctataaa taaagaggaa 960
gaaatcctac ttagcgacat gaacaaacag ttgacttcaa tctctgagga agtgatggat 1020
ctggctaagc atcttcctca tgctttcagt aaattggaaa acccacggag ggtttctatc 1080

-continued

```
ttactaaagg atatttcaga aaatctatat tcactgagga ggatgataat tgggtctact   1140
aacattgaga ctgaactgag gcccagcaat aatttaaact tattatcctt tgaagattca   1200
actactgggg gagtacaaca gaaacaaatt agagaacatg aagttttaat tcacgttgaa   1260
gatgaaacat gggacccaac acttgatcat ttagctaaac atgatggaga agatgtactt   1320
ggaaataaag tggaacgaaa agaagatgga tttgaagatg gagtagaaga caacaaattg   1380
aaagagaata tggaaagagc ttgtttgatg tcgttagata ttacagaaca tgaactccaa   1440
attttggaac agcagtctca ggaagaatat cttagtgata ttgcttataa atctactgag   1500
catttatctc ccaatgataa tgaaaacgat acgtcctatg taattgagag tgatgaagat   1560
ttagaaatgg agatgcttaa gcatttatct cccaatgata atgaaaacga tacgtcctat   1620
gtaattgaga gtgatgaaga tttagaaatg gagatgctta agtctttaga aaacctcaat   1680
agtggcacgg tagaaccaac tcattctaaa tgcttaaaaa tggaaagaaa tctgggtctt   1740
cctactaaag aagaagaaga agatgatgaa aatgaagcta atgaagggga agaagatgat   1800
gataaggact ttttgtggcc agcacccaat gaagagcaag ttacttgcct caagatgtac   1860
tttggccatt ccagttttaa accagttcag tggaaagtga ttcattcagt attagaagaa   1920
agaagagata atgttgctgt catggcaact ggatatggaa agagtttgtg cttccagtat   1980
ccacctgttt atgtaggcaa gattggcctt gttatctctc cccttatttc tctgatggaa   2040
gaccaagtgc tacagcttaa aatgtccaac atcccagctt gcttccttgg atcagcacag   2100
tcagaaaatg ttctaacaga tattaaatta ggtaaatacc ggattgtata cgtaactcca   2160
gaatactgtt caggtaacat gggcctgctc cagcaacttg aggctgatat tggtatcacg   2220
ctcattgctg tggatgaggc tcactgtatt tctgagtggg ggcatgattt tagggattca   2280
ttcaggaagt tgggctccct aaagacagca ctgccaatgg ttccaatcgt tgcacttact   2340
gctactgcaa gttcttcaat ccgggaagac attgtacgtt gcttaaatct gagaaatcct   2400
cagatcacct gtactggttt tgatcgacca aacctgtatt tagaagttag gcgaaaaaca   2460
gggaatatcc ttcaggatct gcagccattt cttgtcaaaa caagttccca ctgggaattt   2520
gaaggtccaa caatcatcta ctgtccttct agaaaaatga cacaacaagt tacaggtgaa   2580
cttaggaaac ttaatctatc ctgtggaaca taccatgcgg gcatgagttt tagcacaagg   2640
aaagacattc atcataggtt tgtaagagat gaaattcagt gtgtcatagc taccatagct   2700
tttggaatgg gcattaataa agctgacatt cgccaagtca ttcattacgg tgctcctaag   2760
gacatggaat catattatca ggagattggt agagctggtc gtgatggact tcaaagttct   2820
tgtcacgtcc tctgggctcc tgcagacatt aacttaaata ggcaccttct tactgagata   2880
cgtaatgaga agtttcgatt atacaaatta aagatgatgg caaagatgga aaaatatctt   2940
cattctagca gatgtaggag acaaatcatc ttgtctcatt ttgaggacaa acaagtacaa   3000
aaagcctcct tgggaattat gggaactgaa aaatgctgtg ataattgcag gtccagattg   3060
gatcattgct attccatgga tgactcagag gatacatcct gggactttgg tccacaagca   3120
tttaagcttt tgtctgctgt ggacatctta ggcgaaaaat ttggaattgg gcttccaatt   3180
ttatttctcc gaggatctaa ttctcagcgt cttgccgatc aatatcgcag gcacagttta   3240
tttggcactg gcaaggatca aacagagagt tggtggaagg ctttttcccg tcagctgatc   3300
actgagggat tcttggtaga agtttctcgg tataacaaat ttatgaagat ttgcgccctt   3360
acgaaaaagg gtagaaattg gcttcataaa gctaatacag aatctcagag cctcatcctt   3420
caagctaatg aagaattgtg tccaaagaag tttcttctgc ctagttcgaa aactgtatct   3480
```

```
tcgggcacca aagagcattg ttataatcaa gtaccagttg aattaagtac agagaagaag   3540

tctaacttgg agaagttata ttcttataaa ccatgtgata agatttcttc tgggagtaac   3600

atttctaaaa aaagtatcat ggtacagtca ccagaaaaag cttacagttc ctcacagcct   3660

gttatttcgg cacaagagca ggagactcag attgtgttat atggcaaatt ggtagaagct   3720

aggcagaaac atgccaataa aatggatgtt cccccagcta ttctggcaac aaacaagata   3780

ctggtggata tggccaaaat gagaccaact acggttgaaa acgtaaaaag gattgatggt   3840

gtttctgaag gcaaagctgc catgttggcc cctctgttgg aagtcatcaa acatttctgc   3900

caaacaaata gtgttcagac agacctcttt tcaagtacaa aacctcaaga agaacagaag   3960

acgagtctgg tagcaaaaaa taaaatatgc acactttcac agtctatggc catcacatac   4020

tctttattcc aagaaaagaa gatgcctttg aagagcatag ctgagagcag gattctgcct   4080

ctcatgacaa ttggcatgca cttatcccaa gcggtgaaag ctggctgccc ccttgatttg   4140

gagcgagcag gcctgactcc agaggttcag aagattattg ctgatgttat ccgaaaccct   4200

cccgtcaact cagatatgag taaaattagc ctaatcagaa tgttagttcc tgaaaacatt   4260

gacacgtacc ttatccacat ggcaattgag atccttaaac atggtcctga cagcggactt   4320

caaccttcat gtgatgtcaa caaaaggaga tgttttcccg gttctgaaga gatctgttca   4380

agttctaaga gaagcaagga agaagtaggc atcaatactg agacttcatc tgcagagaga   4440

aagagacgat tacctgtgtg gtttgccaaa ggaagtgata ccagcaagaa attaatggac   4500

aaaacgaaaa ggggaggtct ttttagttaa gctggcaatt accagaacaa ttatgtttct   4560

tgctgtatta taagaggata gctatatttt atttctgaag agtaaggagt agtattttgg   4620

cttaaaaatc attctaatta caaagttcac tgtttattga agaactggca tcttaaatca   4680

gccttccgca attcatgtag tttctgggtc ttctgggagc ctacgtgagt acatcaccta   4740

acagaatatt aaattagact tcctgtaaga ttgctttaag aaactgttac tgtcctgttt   4800

tctaatctct ttattaaaac agtgtatttg gaaaatgtta tgtgctctga tttgatatag   4860

ataacagatt agtagttaca tggtaattat gtgatataaa atattcatat attatcaaaa   4920

ttctgttttg taaatgtaag aaagcatagt tattttacaa attgttttta ctgtcttttg   4980

aagaagttct taaatacgtt gttaaatggt attagttgac cagggcagtg aaaatgaaac   5040

cgcattttgg gtgccattaa atagggaaaa aacatgtaaa aaatgtaaaa tggagaccaa   5100

ttgcactagg caagtgtata ttttgtattt tatatacaat ttctattatt tttcaagtaa   5160

taaaacaatg tttttcatac tgaatattaa aaaaaaaaaa aaaaaaaa                5208
```

<210> SEQ ID NO 13
<211> LENGTH: 5189
<212> TYPE: DNA
<213> ORGANISM: Homo sapiens

<400> SEQUENCE: 13

```
tgtgcgccgg ggaggcgccg gcttgtactc ggcagcgcgg gaataaagtt tgctgatttg     60

gtgtctagcc tggatgcctg ggttgcagcc ctgcttgtgg tggcgctcca cagtcatccg    120

gctgaagaag acctgttgga ctggatcttc tcgggttttc tttcagatat tgttttgtat    180

ttacccatga agacattgtt ttttggactc tgcaaatagg acatttcaaa gatgagtgaa    240

aaaaaattgg aaacaactgc acagcagcgg aaatgtcctg aatggatgaa tgtgcagaat    300

aaaagatgtg ctgtagaaga aagaaaggca tgtgttcgga agagtgtttt tgaagatgac    360

ctcccccttct tagaattcac tggatccatt gtgtatagtt acgatgctag tgattgctct    420
```

-continued

```
ttcctgtcag aagatattag catgagtcta tcagatgggg atgtggtggg atttgacatg    480
gagtggccac cattatacaa tagagggaaa cttggcaaag ttgcactaat tcagttgtgt    540
gtttctgaga gcaaatgtta cttgttccac gtttcttcca tgtcagtttt tccccaggga    600
ttaaaaatgt tgcttgaaaa taaagcagtt aaaaaggcag gtgtaggaat tgaaggagat    660
cagtggaaac ttctacgtga ctttgatatc aaattgaaga attttgtgga gttgacagat    720
gttgccaata aaaagctgaa atgtacagag acctggagcc ttaacagtct ggttaaacac    780
ctcttaggta aacagctcct gaaagacaag tctatccgct gtagcaattg gagtaaattt    840
cctctcactg aggaccagaa actgtatgca gccactgatg cttatgctgg ttttattatt    900
taccgaaatt tagagatttt ggatgatact gtgcaaaggt ttgctataaa taaagaggaa    960
gaaatcctac ttagcgacat gaacaaacag ttgacttcaa tctctgagga agtgatggat   1020
ctggctaagc atcttcctca tgctttcagt aaattggaaa acccacggag ggtttctatc   1080
ttactaaagg atatttcaga aaatctatat tcactgagga ggatgataat tgggtctact   1140
aacattgaga ctgaactgag gcccagcaat aatttaaact tattatcctt tgaagattca   1200
actactgggg gagtacaaca gaaacaaatt agagaacatg aagttttaat tcacgttgaa   1260
gatgaaacat gggacccaac acttgatcat ttagctaaac atgatggaga agatgtactt   1320
ggaaataaag tggaacgaaa agaagatgga tttgaagatg gagtagaaga caacaaattg   1380
aaagagaata tggaaagagc ttgtttgatg tcgttagata ttacagaaca tgaactccaa   1440
attttggaac agcagtctca ggaagaatat cttagtgata ttgcttataa atctactgag   1500
catttatctc ccaatgataa tgaaaacgat acgtcctatg taattgagag tgatgaagat   1560
ttagaaatgg agatgcttaa gcatttatct cccaatgata atgaaaacga tacgtcctat   1620
gtaattgaga gtgatgaaga tttagaaatg gagatgctta agtctttaga aaacctcaat   1680
agtggcacgg tagaaccaac tcattctaaa tgcttaaaaa tggaaagaaa tctgggtctt   1740
cctactaaag aagaagaaga agatgatgaa aatgaagcta atgaagggga agaagatgat   1800
gataaggact ttttgtggcc agcacccaat gaagagcaag ttacttgcct caagatgtac   1860
tttggccatt ccagttttaa accagttcag tggaaagtga ttcattcagt attagaagaa   1920
agaagagata atgttgctgt catggcaact ggatatggaa agagtttgtg cttccagtat   1980
ccacctgttt atgtaggcaa gattggcctt gttatctctc cccttatttc tctgatggaa   2040
gaccaagtgc tacagcttaa aatgtccaac atcccagctt gcttccttgg atcagcacag   2100
tcagaaaatg ttctaacaga tattaaatta ggtaaatacc ggattgtata cgtaactcca   2160
gaatactgtt caggtaacat gggcctgctc cagcaacttg aggctgatat tggtatcacg   2220
ctcattgctg tggatgaggc tcactgtatt tctgagtggg ggcatgattt tagggattca   2280
ttcaggaagt tgggctccct aaagacagca ctgccaatgg ttccaatcgt tgcacttact   2340
gctactgcaa gttcttcaat ccgggaagac attgtacgtt gcttaaatct gagaaatcct   2400
cagatcacct gtactggttt tgatcgacca aacctgtatt tagaagttag gcgaaaaaca   2460
gggaatatcc ttcaggatct gcagccattt cttgtcaaaa caagttccca ctgggaattt   2520
gaaggtccaa caatcatcta ctgtccttct agaaaaatga cacaacaagt tacaggtgaa   2580
cttaggaaac ttaatctatc ctgtggaaca taccatgcgg gcatgagttt tagcacaagg   2640
aaagacattc atcataggtt tgtaagagat gaaattcagt gtgtcatagc taccatagct   2700
tttggaatgg gcattaataa agctgacatt cgccaagtca ttcattacgg tgctcctaag   2760
gacatggaat catattatca ggagattggt agagctggtc gtgatggact tcaaagttct   2820
```

-continued tgtcacgtcc tctgggctcc tgcagacatt aacttaaata ggcaccttct tactgagata 2880
cgtaatgaga agtttcgatt atacaaatta aagatgatgg caaagatgga aaaatatctt 2940
cattctagca gatgtaggag acaaatcatc ttgtctcatt ttgaggacaa acaagtacaa 3000
aaagcctcct tgggaattat gggaactgaa aaatgctgtg ataattgcag gtccagattg 3060
gatcattgct attccatgga tgactcagag gatacatcct gggactttgg tccacaagca 3120
tttaagcttt tgtctgctgt ggacatctta ggcgaaaaat ttggaattgg gcttccaatt 3180
ttatttctcc gaggatctaa ttctcagcgt cttgccgatc aatatcgcag gcacagttta 3240
tttggcactg gcaaggatca aacagagagt tggtggaagg ctttttcccg tcagctgatc 3300
actgagggat tcttggtaga agtttctcgg tataacaaat ttatgaagat ttgcgccctt 3360
acgaaaaagg gtagaaattg gcttcataaa gctaatacag aatctcagag cctcatcctt 3420
caagctaatg aagaattgtg tccaaagaag tttcttctgc ctagttcgaa aactgtatct 3480
tcgggcacca aagagcattg ttataatcaa gtaccagttg aattaagtac agagaagaag 3540
tctaacttgg agaagttata ttcttataaa ccatgtgata agatttcttc tgggagtaac 3600
atttctaaaa aaagtatcat ggtacagtca ccagaaaaag cttacagttc ctcacagcct 3660
gttatttcgg cacaagagca ggagactcag attgtgttat atggcaaatt ggtagaagct 3720
aggcagaaac atgccaataa aatggatgtt cccccagcta ttctggcaac aaacaagata 3780
ctggtggata tggccaaaat gagaccaact acggttgaaa acgtaaaaag gattgatggt 3840
gtttctgaag gcaaagctgc catgttggcc cctctgttgg aagtcatcaa acatttctgc 3900
caaacaaata gtgttcagac agacctcttt tcaagtacaa aacctcaaga agaacagaag 3960
acgagtctgg tagcaaaaaa taaaatatgc acactttcac agtctatggc catcacatac 4020
tctttattcc aagaaaagaa gatgcctttg aagagcatag ctgagagcag gattctgcct 4080
ctcatgacaa ttggcatgca cttatcccaa gcggtgaaag ctggctgccc ccttgatttg 4140
gagcgagcag gcctgactcc agaggttcag aagattattg ctgatgttat ccgaaaccct 4200
cccgtcaact cagatatgag taaaattagc ctaatcagaa tgttagttcc tgaaaacatt 4260
gacacgtacc ttatccacat ggcaattgag atccttaaac atggtcctga cagcggactt 4320
caaccttcat gtgatgtcaa caaaaggaga tgtttcccg gttctgaaga gatctgttca 4380
agttctaaga gaagcaagga agaagtaggc atcaatactg agacttcatc tgcagagaga 4440
aagagacgat tacctgtgtg gtttgccaaa ggaagtgata ccagcaagaa attaatggac 4500
aaaacgaaaa ggggaggtct ttttagttaa gctggcaatt accagaacaa ttatgtttct 4560
tgctgtatta taagaggata gctatatttt atttctgaag agtaaggagt agtattttgg 4620
cttaaaaatc attctaatta caaagttcac tgtttattga agaactggca tcttaaatca 4680
gccttccgca attcatgtag tttctgggtc ttctgggagc ctacgtgagt acatcaccta 4740
acagaatatt aaattagact tcctgtaaga ttgctttaag aaactgttac tgtcctgttt 4800
tctaatctct ttattaaaac agtgtatttg gaaaatgtta tgtgctctga tttgatatag 4860
ataacagatt agtagttaca tggtaattat gtgatataaa atattcatat attatcaaaa 4920
ttctgttttg taaatgtaag aaagcatagt tattttacaa attgttttta ctgtcttttg 4980
aagaagttct taaatacgtt gttaaatggt attagttgac cagggcagtg aaaatgaaac 5040
cgcattttgg gtgccattaa atagggaaaa aacatgtaaa aaatgtaaaa tggagaccaa 5100
ttgcactagg caagtgtata ttttgtattt tatatacaat ttctattatt tttcaagtaa 5160
taaaacaatg tttttcatac tgaatatta 5189

-continued

<210> SEQ ID NO 14
<211> LENGTH: 3611
<212> TYPE: DNA
<213> ORGANISM: Homo sapiens

<400> SEQUENCE: 14

```
ggtagtatgg cttgcacatc tgccagcttt cgacaaaatt gtaggccctg ttaataatag     60

tccttttgtg tttggtgaaa aagatacgac actgtcagtg gttttgcttt taagatttct    120

tttaaacttt cagtctttag aaaacctcaa tagtggcacg gtagaaccaa ctcattctaa    180

atgcttaaaa atggaaagaa atctgggtct tcctactaaa gaagaagaag aagatgatga    240

aaatgaagct aatgaagggg aagaagatga tgataaggac tttttgtggc cagcacccaa    300

tgaagagcaa gttacttgcc tcaagatgta ctttggccat tccagtttta aaccgatatg    360

gaaagagttt gtgcttccag tatccacctg tttatgtagg caagattggc cttgttatct    420

ctccccttat ttctctgatg gaagaccaag tgctacagct taaaatgtcc aacatcccag    480

cttgcttcct tggatcagca cagtcagaaa atgttctaac agatattaaa ttaggtaaat    540

accggattgt atacgtaact ccagaatact gttcaggtaa catgggcctg ctccagcaac    600

ttgaggctga tattggtatc acgctcattg ctgtggatga ggctcactgt atttctgagt    660

gggggcatga ttttagggat tcattcagga agttgggctc cctaaagaca gcactgccaa    720

tggttccaat cgttgcactt actgctactg caagttcttc aatccgggaa gacattgtac    780

gttgcttaaa tctgagaaat cctcagatca cctgtactgg ttttgatcga ccaaacctgt    840

atttagaagt taggcgaaaa acagggaata tccttcagga tctgcagcca tttcttgtca    900

aaacaagttc ccactgggaa tttgaaggtc caacaatcat ctactgtcct tctagaaaaa    960

tgacacaaca agttacaggt gaacttagga aacttaatct atcctgtgga acataccatg   1020

cgggcatgag ttttagcaca aggaaagaca ttcatcatag gtttgtaaga gatgaaattc   1080

agtgtgtcat agctaccata gcttttggaa tgggcattaa taaagctgac attcgccaag   1140

tcattcatta cggtgctcct aaggacatgg aatcatatta tcaggagatt ggtagagctg   1200

gtcgtgatgg acttcaaagt tcttgtcacg tcctctgggc tcctgcagac attaacttaa   1260

ataggcacct tcttactgag atacgtaatg agaagtttcg attatacaaa ttaaagatga   1320

tggcaaagat ggaaaaatat cttcattcta gcagatgtag gagacaaatc atcttgtctc   1380

attttgagga caaacaagta caaaaagcct ccttgggaat tatgggaact gaaaaatgct   1440

gtgataattg caggtccaga ttggatcatt gctattccat ggatgactca gaggatacat   1500

cctgggactt tggtccacaa gcatttaagc ttttgtctgc tgtggacatc ttaggcgaaa   1560

aatttggaat tgggcttcca attttatttc tccgaggatc taattctcag cgtcttgccg   1620

atcaatatcg caggcacagt ttatttggca ctggcaagga tcaaacagag agttggtgga   1680

aggctttttc ccgtcagctg atcactgagg gattcttggt agaagtttct cggtataaca   1740

aatttatgaa gatttgcgcc cttacgaaaa agggtagaaa ttggcttcat aaagctaata   1800

cagaatctca gagcctcatc cttcaagcta atgaagaatt gtgtccaaag aagtttcttc   1860

tgcctagttc gaaaactgta tcttcgggca ccaaagagca ttgttataat caagtaccag   1920

ttgaattaag tacagagaag aagtctaact tggagaagtt atattcttat aaaccatgtg   1980

ataagatttc ttctgggagt aacatttcta aaaaaagtat catggtacag tcaccagaaa   2040

aagcttacag ttcctcacag cctgttattt cggcacaaga gcaggagact cagattgtgt   2100

tatatggcaa attggtagaa gctaggcaga aacatgccaa taaaatggat gttcccccag   2160
```

```
ctattctggc aacaaacaag atactggtgg atatggccaa aatgagacca actacggttg   2220

aaaacgtaaa aaggattgat ggtgtttctg aaggcaaagc tgccatgttg gcccctctgt   2280

tggaagtcat caaacatttc tgccaaacaa atagtgttca gacagacctc ttttcaagta   2340

caaaacctca agaagaacag aagacgagtc tggtagcaaa aaataaaata tgcacacttt   2400

cacagtctat ggccatcaca tactctttat tccaagaaaa gaagatgcct ttgaagagca   2460

tagctgagag caggattctg cctctcatga caattggcat gcacttatcc caagcggtga   2520

aagctggctg ccccccttgat ttggagcgag caggccggac tccagaggtt cagaagatta   2580

ttgctgatgt tatccgaaac cctcccgtca actcagatat gagtaaaatt agcctaatca   2640

gaatgttagt tcctgaaaac attgacacgt accttatcca catggcaatt gagatcctta   2700

aacatggtcc tgacagcgga cttcaacctt catgtgatgt caacaaaagg agatgttttc   2760

ccggttctga agagatctgt tcaagttcta agagaagcaa ggaagaagta ggcatcaata   2820

ctgagacttc atccgcagag agaaagagac gattacctgt gtggtttgcc aaaggaagtg   2880

ataccagcaa gaaattaatg gacaaaacga aaaggggagg tctttttagt taagctggca   2940

attaccagaa caattatgtt tcttgctgta ttataagagg atagctatat tttatttctg   3000

aagagtaagg agtagtattt tggcttaaaa atcattctaa ttacaaagtt cactgtttat   3060

tgaagaactg gcatcttaaa tcagccttcc gcaattcatg tagtttctgg gtcttctggg   3120

agcctacgtg agtacatcac ctaacagaat attaaattag acttcctgta agattgcttt   3180

aagaaactgt tactgtcctg ttttctaatc tctttattaa aacagtgtat ttggaaaatg   3240

ttatgtgctc tgatttgata tagataacag attagtagtt acatggtaat tatgtgatat   3300

aaaatattca tatattatca aaattctgtt ttgtaaatgt aagaaagcat agttatttta   3360

caaattgttt ttactgtctt ttgaagaagt tcttaaatac gttgttaaat ggtattagtt   3420

gaccagggca gtgaaaatga aaccgcattt tgggtgccat taaataggga aaaaacatgt   3480

aaaaaatgta aaatggagac caattgcact aggcaagtgt atattttgta ttttatatac   3540

aatttctatt atttttcaag taataaaaca atgtttttca tactgaatat tataaaaaaa   3600

aaaaaaaaaa a                                                        3611
```

<210> SEQ ID NO 15
<211> LENGTH: 4437
<212> TYPE: DNA
<213> ORGANISM: Homo sapiens

<400> SEQUENCE: 15

```
gcgcggcggc cgtggttgcg gcgcgggaag tttggatcct ggttccgtcc gctaggagtc     60

tgcgtgcgag gattatggct gctgttcctc aaaataatct acaggagcaa ctagaacgtc    120

actcagccag aacacttaat aataaattaa gtctttcaaa accaaaattt tcaggtttca    180

cttttaaaaa gaaaacatct tcagataaca atgtatctgt aactaatgtg tcagtagcaa    240

aaacacctgt attaagaaat aaagatgtta atgttaccga agacttttcc ttcagtgaac    300

ctctacccaa caccacaaat cagcaaaggg tcaaggactt ctttaaaaat gctccagcag    360

gacaggaaac acagagaggt ggatcaaaat cattattgcc agatttcttg cagactccga    420

aggaagttgt atgcactacc caaaacacac caactgtaaa gaaatcccgg gatactgctc    480

tcaagaaatt agaatttagt tcttcaccag attctttaag taccatcaat gattgggatg    540

atatggatga ctttgatact tctgagactt caaaatcatt tgttacacca ccccaaagtc    600

actttgtaag agtaagcact gctcagaaat caaaaaaggg taagagaaac ttttttaaag    660
```

-continued

```
cacagcttta tacaacaaac acagtaaaga ctgatttgcc tccaccctcc tctgaaagcg    720
agcaaataga tttgactgag gaacagaagg atgactcaga atggttaagc agcgatgtga    780
tttgcatcga tgatggcccc attgctgaag tgcatataaa tgaagatgct caggaaagtg    840
actctctgaa aactcatttg gaagatgaaa gagataatag cgaaaagaag aagaatttgg    900
aagaagctga attacattca actgagaaag ttccatgtat tgaatttgat gatgatgatt    960
atgatacgga ttttgttcca ccttctccag aagaaattat ttctgcttct tcttcctctt   1020
caaaatgcct tagtacgtta aaggaccttg acacatctga cagaaaagag gatgttctta   1080
gcacatcaaa agatcttttg tcaaaacctg agaaaatgag tatgcaggag ctgaatccag   1140
aaaccagcac agactgtgac gctagacaga taagtttaca gcagcagctt attcatgtga   1200
tggagcacat ctgtaaatta attgatacta ttcctgatga taaactgaaa cttttggatt   1260
gtgggaacga actgcttcag cagcggaaca taagaaggaa acttctaacg gaagtagatt   1320
ttaataaaag tgatgccagt cttcttggct cattgtggag atacaggcct gattcacttg   1380
atggccctat ggagggtgat tcctgcccta cagggaattc tatgaaggag ttaaattttt   1440
cacaccttcc ctcaaattct gtttctcctg ggactgttt actgactacc accctaggaa    1500
agacaggatt ctctgccacc aggaagaatc tttttgaaag gcctttattc aatacccatt   1560
tacagaagtc ctttgtaagt agcaactggg ctgaaacacc aagactagga aaaaaaaatg   1620
aaagctctta tttcccagga aatgttctca caagcactgc tgtgaaagat cagaataaac   1680
atactgcttc aataaatgac ttagaaagag aaacccaacc ttcctatgat attgataatt   1740
ttgacataga tgactttgat gatgatgatg actgggaaga cataatgcat aatttagcag   1800
ccagcaaatc ttccacagct gcctatcaac ccatcaagga aggtcggcca attaaatcag   1860
tatcagaaag actttcctca gccaagacag actgtcttcc agtgtcatct actgctcaaa   1920
atataaactt ctcagagtca attcagaatt atactgacaa gtcagcacaa aatttagcat   1980
ccagaaatct gaaacatgag cgtttccaaa gtcttagttt tcctcataca aaggaaatga   2040
tgaagatttt tcataaaaaa tttggcctgc ataattttag aactaatcag ctagaggcga   2100
tcaatgctgc actgcttggt gaagactgtt ttatcctgat gccgactgga ggtggtaaga   2160
gtttgtgtta ccagctccct gcctgtgttt ctcctggggt cactgttgtc atttctccct   2220
tgagatcact tatcgtagat caagtccaaa agctgacttc cttggatatt ccagctacat   2280
atctgacagg tgataagact gactcagaag ctacaaatat ttacctccag ttatcaaaaa   2340
aagacccaat cataaaactt ctatatgtca ctccagaaaa gatctgtgca agtaacagac   2400
tcatttctac tctggagaat ctctatgaga ggaagctctt ggcacgtttt gttattgatg   2460
aagcacattg tgtcagtcag tggggacatg attttcgtca agattacaaa agaatgaata   2520
tgcttcgcca gaagtttcct tctgttccgg tgatggctct tacggccaca gctaatccca   2580
gggtacagaa ggacatcctg actcagctga agattctcag acctcaggtg tttagcatga   2640
gctttaacag acataatctg aaatactatg tattaccgaa aaagcctaaa aaggtggcat   2700
ttgattgcct agaatggatc agaaagcacc acccatatga ttcagggata atttactgcc   2760
tctccaggcg agaatgtgac accatggctg acacgttaca gagagatggg ctcgctgctc   2820
ttgcttacca tgctggcctc agtgattctg ccagagatga agtgcagcag aagtggatta   2880
atcaggatgg ctgtcaggtt atctgtgcta caattgcatt tggaatgggg attgacaaac   2940
cggacgtgcg atttgtgatt catgcatctc tccctaaatc tgtggagggt tactaccaag   3000
aatctggcag agctggaaga gatggggaaa tatctcactg cctgcttttc tatacctatc   3060
```

atgatgtgac cagactgaaa agacttataa tgatggaaaa agatggaaac catcatacaa 3120
gagaaactca cttcaataat ttgtatagca tggtacatta ctgtgaaaat ataacggaat 3180
gcaggagaat acagcttttg gcctactttg gtgaaaatgg atttaatcct gatttttgta 3240
agaaacaccc agatgtttct tgtgataatt gctgtaaaac aaaggattat aaaacaagag 3300
atgtgactga cgatgtgaaa agtattgtaa gatttgttca agaacatagt tcatcacaag 3360
gaatgagaaa tataaaacat gtaggtcctt ctggaagatt tactatgaat atgctggtcg 3420
acattttctt ggggagtaag agtgcaaaaa tccagtcagg tatatttgga aaaggatctg 3480
cttattcacg acacaatgcc gaaagacttt ttaaaaagct gatacttgac aagattttgg 3540
atgaagactt atatatcaat gccaatgacc aggcgatcgc ttatgtgatg ctcggaaata 3600
aagcccaaac tgtactaaat ggcaatttaa aggtagactt tatggaaaca gaaaattcca 3660
gcagtgtgaa aaaacaaaaa gcgttagtag caaaagtgtc tcagagggaa gagatggtta 3720
aaaaatgtct tggagaactt acagaagtct gcaaatctct ggggaaagtt tttggtgtcc 3780
attacttcaa tatttttaat accgtcactc tcaagaagct tgcagaatct ttatcttctg 3840
atcctgaggt tttgcttcaa attgatggtg ttactgaaga caaactggaa aaatatggtg 3900
cggaagtgat ttcagtatta cagaaatact ctgaatggac atcgccagct gaagacagtt 3960
ccccagggat aagcctgtcc agcagcagag gccccggaag aagtgccgct gaggagcttg 4020
acgaggaaat acccgtatct tcccactact ttgcaagtaa aaccagaaat gaaaggaaga 4080
ggaaaaagat gccagcctcc caaaggtcta agaggagaaa aactgcttcc agtggttcca 4140
aggcaaaggg ggggtctgcc acatgtagaa agatatcttc caaaacgaaa tcctccagca 4200
tcattggatc cagttcagcc tcacatactt ctcaagcgac atcaggagcc aatagcaaat 4260
tggggattat ggctccaccg aagcctataa atagaccgtt tcttaagcct tcatatgcat 4320
tctcataaca accgaatctc aatgtacata gaccctcttt cttgtttgtc agcatctgac 4380
catctgtgac tataaagctg ttattcttgt tataccaaaa aaaaaaaaaa aaaaaaa 4437

<210> SEQ ID NO 16
<211> LENGTH: 4437
<212> TYPE: DNA
<213> ORGANISM: Homo sapiens

<400> SEQUENCE: 16
gcgcggcggc cgtggttgcg gcgcgggaag tttggatcct ggttccgtcc gctaggagtc 60
tgcgtgcgag gattatggct gctgttcctc aaaataatct acaggagcaa ctagaacgtc 120
actcagccag aacacttaat aataaattaa gtctttcaaa accaaaattt tcaggtttca 180
cttttaaaaa gaaaacatct tcagataaca atgtatctgt aactaatgtg tcagtagcaa 240
aaacacctgt attaagaaat aaagatgtta atgttaccga agacttttcc ttcagtgaac 300
ctctacccaa caccacaaat cagcaaaggg tcaaggactt ctttaaaaat gctccagcag 360
gacaggaaac acagagaggt ggatcaaaat cattattgcc agatttcttg cagactccga 420
aggaagttgt atgcactacc caaaacacac caactgtaaa gaaatcccgg gatactgctc 480
tcaagaaatt agaatttagt tcttcaccag attctttaag taccatcaat gattgggatg 540
atatggatga ctttgatact tctgagactt caaaatcatt tgttacacca ccccaaagtc 600
actttgtaag agtaagcact gctcagaaat caaaaaaggg taagagaaac ttttttaaag 660
cacagcttta tacaacaaac acagtaaaga ctgatttgcc tccaccctcc tctgaaagcg 720
agcaaataga tttgactgag gaacagaagg atgactcaga atggttaagc agcgatgtga 780

-continued

```
tttgcatcga tgatggcccc attgctgaag tgcatataaa tgaagatgct caggaaagtg    840
actctctgaa aactcatttg gaagatgaaa gagataatag cgaaaagaag aagaatttgg    900
aagaagctga attacattca actgagaaag ttccatgtat tgaatttgat gatgatgatt    960
atgatacgga ttttgttcca ccttctccag aagaaattat ttctgcttct tcttcctctt   1020
caaaatgcct tagtacgtta aaggaccttg acacatctga cagaaaagag gatgttctta   1080
gcacatcaaa agatcttttg tcaaaacctg agaaaatgag tatgcaggag ctgaatccag   1140
aaaccagcac agactgtgac gctagacaga taagtttaca gcagcagctt attcatgtga   1200
tggagcacat ctgtaaatta attgatacta ttcctgatga taaactgaaa cttttggatt   1260
gtgggaacga actgcttcag cagcggaaca taagaaggaa acttctaacg gaagtagatt   1320
ttaataaaag tgatgccagt cttcttggct cattgtggag atacaggcct gattcacttg   1380
atggccctat ggagggtgat tcctgcccta cagggaattc tatgaaggag ttaaattttt   1440
cacaccttcc ctcaaattct gtttctcctg ggactgtttt actgactacc accctaggaa   1500
agacaggatt ctctgccacc aggaagaatc tttttgaaag gcctttattc aatacccatt   1560
tacagaagtc ctttgtaagt agcaactggg ctgaaacacc aagactagga aaaaaaaatg   1620
aaagctctta tttcccagga aatgttctca caagcactgc tgtgaaagat cagaataaac   1680
atactgcttc aataaatgac ttagaaagag aaacccaacc ttcctatgat attgataatt   1740
ttgacataga tgactttgat gatgatgatg actgggaaga cataatgcat aatttagcag   1800
ccagcaaatc ttccacagct gcctatcaac ccatcaagga aggtcggcca attaaatcag   1860
tatcagaaag actttcctca gccaagacag actgtcttcc agtgtcatct actgctcaaa   1920
atataaactt ctcagagtca attcagaatt atactgacaa gtcagcacaa aatttagcat   1980
ccagaaatct gaaacatgag cgtttccaaa gtcttagttt tcctcataca aaggaaatga   2040
tgaagatttt tcataaaaaa tttggcctgc ataattttag aactaatcag ctagaggcga   2100
tcaatgctgc actgcttggt gaagactgtt ttatcctgat gccgactgga ggtggtaaga   2160
gtttgtgtta ccagctccct gcctgtgttt ctcctggggt cactgttgtc atttctccct   2220
tgagatcact tatcgtagat caagtccaaa agctgacttc cttggatatt ccagctacat   2280
atctgacagg tgataagact gactcagaag ctacaaatat ttacctccag ttatcaaaaa   2340
aagacccaat cataaaactt ctatatgtca ctccagaaaa gatctgtgca agtaacagac   2400
tcatttctac tctggagaat ctctatgaga ggaagctctt ggcacgtttt gttattgatg   2460
aagcacattg tgtcagtcag tggggacatg attttcgtca agattacaaa agaatgaata   2520
tgcttcgcca gaagtttcct tctgttccgg tgatggctct tacggccaca gctaatccca   2580
gggtacagaa ggacatcctg actcagctga agattctcag acctcaggtg tttagcatga   2640
gctttaacag acataatctg aaatactatg tattaccgaa aaagcctaaa aaggtggcat   2700
ttgattgcct agaatggatc agaaagcacc acccatatga ttcagggata atttactgcc   2760
tctccaggcg agaatgtgac accatggctg acacgttaca gagagatggg ctcgctgctc   2820
ttgcttacca tgctggcctc agtgattctg ccagagatga agtgcagcag aagtggatta   2880
atcaggatgg ctgtcaggtt atctgtgcta caattgcatt tggaatgggg attgacaaac   2940
cggacgtgcg atttgtgatt catgcatctc tccctaaatc tgtggagggt tactaccaag   3000
aatctggcag agctggaaga gatggggaaa tatctcactg cctgcttttc tatacctatc   3060
atgatgtgac cagactgaaa agacttataa tgatggaaaa agatggaaac catcatacaa   3120
gagaaactca cttcaataat ttgtatagca tggtacatta ctgtgaaaat ataacggaat   3180
```

-continued

```
gcaggagaat acagcttttg gcctactttg gtgaaaatgg atttaatcct gatttttgta   3240
agaaacaccc agatgtttct tgtgataatt gctgtaaaac aaaggattat aaaacaagag   3300
atgtgactga cgatgtgaaa agtattgtaa gatttgttca agaacatagt tcatcacaag   3360
gaatgagaaa tataaaacat gtaggtcctt ctggaagatt tactatgaat atgctggtcg   3420
acatttcttt ggggagtaag agtgcaaaaa tccagtcagg tatatttgga aaaggatctg   3480
cttattcacg acacaatgcc gaaagacttt ttaaaaagct gatacttgac aagattttgg   3540
atgaagactt atatatcaat gccaatgacc aggcgatcgc ttatgtgatg ctcggaaata   3600
aagcccaaac tgtactaaat ggcaatttaa aggtagactt tatggaaaca gaaaattcca   3660
gcagtgtgaa aaaacaaaaa gcgttagtag caaaagtgtc tcagagggaa gagatggtta   3720
aaaaatgtct tggagaactt acagaagtct gcaaatctct ggggaaagtt tttggtgtcc   3780
attacttcaa tatttttaat accgtcactc tcaagaagct tgcagaatct ttatcttctg   3840
atcctgaggt tttgcttcaa attgatggtg ttactgaaga caaactggaa aaatatggtg   3900
cggaagtgat ttcagtatta cagaaatact ctgaatggac atcgccagct gaagacagtt   3960
ccccagggat aagcctgtcc agcagcagag gccccggaag aagtgccgct gaggagcttg   4020
acgaggaaat acccgtatct tcccactact ttgcaagtaa aaccagaaat gaaaggaaga   4080
ggaaaaagat gccagcctcc caaaggtcta agaggagaaa aactgcttcc agtggttcca   4140
aggcaaaggg ggggtctgcc acatgtagaa agatatcttc caaaacgaaa tcctccagca   4200
tcattggatc cagttcagcc tcacatactt ctcaagcgac atcaggagcc aatagcaaat   4260
tggggattat ggctccaccg aagcctataa atagaccgtt tcttaagcct tcatatgcat   4320
tctcataaca accgaatctc aatgtacata gaccctcttt cttgtttgtc agcatctgac   4380
catctgtgac tataaagctg ttattcttgt tataccaaaa aaaaaaaaaa aaaaaaa      4437
```

<210> SEQ ID NO 17
<211> LENGTH: 4493
<212> TYPE: DNA
<213> ORGANISM: Homo sapiens

<400> SEQUENCE: 17

```
agcggggatc ctggttccgt ccgctaggag tctgcgtgcg aggattatgg ctgctgttcc     60
tcaaaataat ctacaggagc aactagaacg tcactcagcc agaacactta ataataaatt    120
aagtctttca aaaccaaaat tttcaggttt cacttttaaa aagaaaacat cttcagataa    180
caatgtatct gtaactaatg tgtcagtagc aaaaacacct gtattaagaa ataaagatgt    240
taatgttacc gaagactttt ccttcagtga acctctaccc aacaccacaa atcagcaaag    300
ggtcaaggac ttctttaaaa atgctccagc aggacaggaa acacagagag gtggatcaaa    360
atcattattg ccagatttct tgcagactcc gaaggaagtt gtatgcacta cccaaaacac    420
accaactgta aagaaatccc gggatactgc tctcaagaaa ttagaattta gttcttcacc    480
agattcttta agtaccatca atgattggga tgatatggat gactttgata cttctgagac    540
ttcaaaatca tttgttacac caccccaaag tcactttgta agagtaagca ctgctcagaa    600
atcaaaaaag ggtaagagaa actttttaa agcacagctt tatacaacaa acacagtaaa    660
gactgatttg cctccaccct cctctgaaag cgagcaaata gatttgactg aggaacagaa    720
ggatgactca gaatggttaa gcagcgatgt gatttgcatc gatgatggcc ccattgctga    780
agtgcatata aatgaagatg ctcaggaaag tgactctctg aaaactcatt tggaagatga    840
aagagataat agcgaaaaga agaagaattt ggaagaagct gaattacatt caactgagaa    900
```

-continued

```
agttccatgt attgaatttg atgatgatga ttatgatacg gattttgttc caccttctcc    960
agaagaaatt atttctgctt cttcttcctc ttcaaaatgc cttagtacgt taaaggacct   1020
tgacacctct gacagaaaag aggatgttct tagcacatca aaagatcttt tgtcaaaacc   1080
tgagaaaatg agtatgcagg agctgaatcc agaaaccagc acagactgtg acgctagaca   1140
gataagttta cagcagcagc ttattcacgt gatggagcac atctgtaaat taattgatac   1200
tattcctgat gataaactga aacttttgga ttgtgggaac gaactgcttc agcagcggaa   1260
cataagaagg aaacttctaa cggaagtaga ttttaataaa agtgatgcca gtcttcttgg   1320
ctcattgtgg agatacaggc ctgattcact tgatggccct atggagggtg attcctgccc   1380
tacagggaat tctatgaagg agttaaattt ttcacacctt ccctcaaatt ctgtttctcc   1440
tggggactgt ttactgacta ccaccctagg aaagacagga ttctctgcca ccaggaagaa   1500
tctttttgaa aggcctttat tcaataccca tttacagaag tcctttgtaa gtagcaactg   1560
ggctgaaaca ccaagactag gaaaaaaaaa aatgaaagct cttatttccc aggaaatgtt   1620
ctcacaagca ctgctgtgaa agatcagaat aaacatactg cttcaataaa tgacttagaa   1680
agagaaaccc aaccttccta tgatattgat aattttgaca tagatgactt tgatgatgat   1740
gatgactggg aagacataat gcataattta gcagccagca aatcttccac agctgcctat   1800
caacccatca aggaaggtcg gccaattaaa tcagtatcag aaagactttc ctcagccaag   1860
acagactgtc ttccagtgtc atctactgct caaaatataa acttctcaga gtcaattcag   1920
aattatactg acaagtcagc acaaaattta gcatccagaa atctgaaaca tgagcgtttc   1980
caaagtctta gttttcctca tacaaaggaa atgatgaaga tttttcataa aaaatttggc   2040
ctgcataatt ttagaactaa tcagctagag gcgatcaatg ctgcactgct tggtgaagac   2100
tgttttatcc tgatgccgac tggaggtggt aagagtttgt gttaccagct ccctgcctgt   2160
gtttctcctg ggtcactgt tgtcatttct cccttgagat cacttatcgt agatcaagtc   2220
caaaagctga cttccttgga tattccagct acatatctga caggtgataa gactgactca   2280
gaagctacaa atatttacct ccagttatca aaaaaagacc caatcataaa acttctatat   2340
gtcactccag aaaagatctg tgcaagtaac agactcattt ctactctgga gaatctctat   2400
gagaggaagc tcttggcacg ttttgttatt gatgaagcac attgtgtcag tcagtgggga   2460
catgattttc gtcaagatta caaaagaatg aatatgcttc gccagaagtt tccttctgtt   2520
ccggtgatgg ctcttacggc cacagctaat cccagggtac agaaggacat cctgactcag   2580
ctgaagattc tcagacctca ggtgtttagc atgagcttta acagacataa tctgaaatac   2640
tatgtattac cgaaaaagcc taaaaaggtg gcatttgatt gcctagaatg gatcagaaag   2700
caccacccat atgattcagg gataatttac tgcctctcca ggcgagaatg tgacaccatg   2760
gctgacacgt tacagagaga tgggctcgct gctcttgctt accatgctgg cctcagtgat   2820
tctgccagag atgaagtgca gcagaagtgg attaatcagg atggctgtca ggttatctgt   2880
gctacaattg catttggaat ggggattgac aaaccggacg tgcgatttgt gattcatgca   2940
tctctcccta aatctgtgga gggttactac caagaatctg gcagagctgg aagagatggg   3000
gaaatatctc actgcctgct tttctatacc tatcatgatg tgaccagact gaaaagactt   3060
ataatgatgg aaaaagatgg aaaccatcat acaagagaaa ctcacttcaa taatttgtat   3120
agcatggtac attactgtga aaatataacg gaatgcagga gaatacagct tttggcctac   3180
tttggtgaaa atggatttaa tcctgatttt tgtaagaaac acccagatgt ttcttgtgat   3240
aattgctgta aaacaaagga ttataaaaca agagatgtga ctgacgatgt gaaaagtatt   3300
```

gtaagatttg ttcaagaaca tagttcatca caaggaatga gaaatataaa acatgtaggt 3360
ccttctggaa gatttactat gaatatgctg gtcgacattt tcttggggag taagagtgca 3420
aaaatccagt caggtatatt tggaaaagga tctgcttatt cacgacacaa tgccgaaaga 3480
ctttttaaaa agctgatact tgacaagatt ttggatgaag acttatatat caatgccaat 3540
gaccaggcga tcgcttatgt gatgctcgga aataaagccc aaactgtact aaatggcaat 3600
ttaaaggtag actttatgga aacagaaaat tccagcagtg tgaaaaaaca aaaagcgtta 3660
gtagcaaaag tgtctcagag ggaagagatg gttaaaaaat gtcttggaga acttacagaa 3720
gtctgcaaat ctctggggaa agtttttggt gtccattact tcaatatttt taataccgtc 3780
actctcaaga agcttgcaga atctttatct tctgatcctg aggttttgct tcaaattgat 3840
ggtgttactg aagacaaact ggaaaaatat ggtgcggaag tgatttcagt attacagaaa 3900
tactctgaat ggacatcgcc agctgaagac agttccccag ggataagcct gtccagcagc 3960
agaggccccg gaagaagtgc cgctgaggag ctcgacgagg aaatacccat atcttcccac 4020
tactttgcaa gtaaaaccag aaatgaaagg aagaggaaaa agatgccagc ctcccaaagg 4080
tctaagagga gaaaaactgc ttccagtggt tccaaggcaa aggggggggtc tgccacatgt 4140 agaaagatat cttccaaaac gaaatcctcc agcatcattg gatccagttc agcctcacat 4200
acttctcaag cgacatcagg agccaatagc aaattgggga ttatggctcc accgaagcct 4260
ataaatagac cgtttcttaa gccttcatat gcattctcat aacaaccgaa tctcaatgta 4320
catagaccct ctttcttgtt tgtcagcatc tgaccatctg tgactataaa gctgttattc 4380
ttgttatacc atttgaagtt tttactcgtc tctattaata tttaaataaa tgctgggggg 4440
tgatagttct tctttttaaa ataaacattt tcttttgaaa aaaaaaaaaa aaa 4493

<210> SEQ ID NO 18
<211> LENGTH: 3627
<212> TYPE: DNA
<213> ORGANISM: Homo sapiens

<400> SEQUENCE: 18
atggagcggc tgcgggacgt gcgggagcgg ctgcaggcgt gggagcgcgc gttccgacgg 60
cagcgcgggc ggcgaccgag ccaggacgac gtggaggcgg cgccggagga gacccgcgcg 120
ctctaccggg agtaccgcac tctgaagcgt accacgggcc aggccggcgg cgggctccgc 180
agctccgagt cgctccccgc ggcggccgaa gaggcgccag agccccgctg ctgggggccc 240
catctgaatc gggctgcgac caagagtcca cagcctacgc cagggcggag ccgccagggc 300
tcggtgccgg actacgggca gcggctcaag gccaatctga aggcaccct gcaggccgga 360 ccagccctgg gccgcagacc gtggcctcta ggaagagcct catctaaggc atccacccca 420
aagcccccag gtacagggcc tgtcccctcc tttgcagaaa aagtcagtga tgagcctcca 480
cagctccctg agccccagcc aaggccaggc cggctccagc atctgcaggc atccctgagc 540
cagcggctgg gctccctaga tcctggctgg ttacagcgat gtcacagtga ggtcccagat 600
tttctggggg cccccaaagc ctgcaggcct gatctaggct cagaggaatc acaacttctg 660
atccctggtg agtcggctgt ccttggtcct ggtgctggct cccagggccc agaggcttca 720
gccttccaag aagtcagcat ccgtgtgggg agcccccagc ccagcagcag tggaggcgag 780
aagcggagat ggaacgagga gccctgggag agccccgcac aggtccagca ggagagcagc 840
caagctggac ccccatcgga gggggctggg gctgtagcag ttgaggaaga ccctccaggg 900
gaacctgtac aggcacagcc acctcagccc tgcagcagcc catcgaaccc caggtaccac 960

-continued

```
ggactcagcc cctccagtca agctagggct gggaaggctg agggcacagc ccccctgcac   1020
atcttccctc ggctggcccg ccatgacagg ggcaattacg tacggctcaa catgaagcag   1080
aaacactacg tgcggggccg ggcactccgt agcaggctcc tccgcaagca ggcatggaag   1140
cagaagtggc ggaagaaagg ggagtgtttt gggggtggtg gtgccacagt cacaaccaag   1200
gagtcttgtt tcctgaacga gcagttcgat cactgggcag cccagtgtcc ccggccagca   1260
agtgaggaag acacagatgc tgttgggcct gagccactgg ttccttcacc acaacctgta   1320
cctgaggtgc ccagcctgga ccccaccgtg ctgccactct actccctggg gccctcaggg   1380
cagttggcag agacgccggc tgaggtgttc caggccctgg agcagctggg gcaccaagcc   1440
tttcgccctg ggcaggagcg tgcagtcatg cggatcctgt ctggcatctc cacgctgctg   1500
gtgctgccta caggtgccgg caagtccctg tgctaccagc tcccagcgct gctctacagc   1560
cggcgcagcc cctgcctcac gttggtcgtc tctcccctgc tgtcactcat ggatgaccag   1620
gtgtctggcc tgccaccgtg tctcaaggcg gcctgcatac actcgggcat gaccaggaag   1680
caacgggaat ctgtcctgca gaagattcgg gcagcccagg tacacgtgct gatgctgaca   1740
cctgaggcac tggtgggggc gggaggcctc cctccagccg cacagctgcc tccagttgct   1800
tttgcctgca ttgatgaggc ccactgcctc tcccagtggt cccacaactt ccggccctgc   1860
tacctgcgcg tctgcaaggt gcttcgggag cgcatgggcg tgcactgctt cctgggcctc   1920
acagccacag ccacacgccg cactgccagt gacgtggcac agcacctggc tgtggctgaa   1980
gagcctgacc tccacgggcc agccccagtt cccaccaacc tgcacctttc cgtgtccatg   2040
gacagggaca cagaccaggc actgttgacg ctgctgcaag gcaaacgttt tcaaaacctc   2100
gattccatta tcatttactg caaccggcgc gaggacacag agcggatcgc tgcgctcctc   2160
cgaacctgcc tgcacgcagc ctgggtccca gggtctggag gtcgtgcccc caaaaccaca   2220
gccgaggcct accacgcggg catgtgcagc cgggaacggc ggcgggtaca gcgagccttc   2280
atgcagggcc agttgcgggt ggtggtggcc acggtggcct ttgggatggg gctggaccgg   2340
ccagatgtgc gggctgtgct gcatctgggg ctgcccccaa gcttcgagag ctacgtgcag   2400
gccgtgggcc gggccgggcg tgacgggcag cctgcccact gccacctctt cctgcagccc   2460
cagggcgaag acctgcgaga gctgcgcaga catgtgcacg ccgacagcac ggacttcctg   2520
gctgtgaaga ggctggtaca gcgcgtgttc ccagcctgca cctgcacctg caccaggccg   2580
ccctcggagc aggaaggggc cgtgggtggg gagaggcctg tgcccaagta ccccccctcaa   2640
gaggctgagc agcttagcca ccaagcagcc ccaggaccca gaagggtctg catgggccat   2700
gagcgggcac tcccaataca gcttaccgta caggctttgg acatgccgga ggaggccatc   2760
gagactttgc tgtgctacct ggagctgcac ccacaccact ggctggagct gctggcgacc   2820
acctataccc attgccgtct gaactgccct gggggccctg cccagctcca ggccctggcc   2880
cacaggtgtc cccctttggc tgtgtgcttg gcccagcagc tgcctgagga cccagggcaa   2940
ggcagcagct ccgtggagtt tgacatggtc aagctggtgg actccatggg ctgggagctg   3000
gcctctgtgc ggcgggctct ctgccagctg cagtgggacc acgagcccag gacaggtgtg   3060
cggcgtggga caggggtgct tgtggagttc agtgagctgg ccttccacct tcgcagcccg   3120
ggggacctga ccgctgagga gaaggaccag atatgtgact tcctctatgg ccgtgtgcag   3180
gcccgggagc gccaggccct ggcccgtctg cgcagaacct tccaggcctt tcacagcgta   3240
gccttcccca gctgcgggcc ctgcctggag cagcaggatg aggagcgcag caccaggctc   3300
aaggacctgc tcggccgcta ctttgaggaa gaggaagggc aggagccggg aggcatggag   3360
```

-continued

```
gacgcacagg gccccgagcc agggcaggcc agactccagg attgggagga ccaggtccgc   3420

tgcgacatcc gccagttcct gtccctgagg ccagaggaga agttctccag cagggctgtg   3480

gcccgcatct tccacggcat cggaagcccc tgctacccgg cccaggtgta cgggcaggac   3540

cgacgcttct ggagaaaata cctgcacctg agcttccatg ccctggtggg cctggccacg   3600

gaagagctcc tgcaggtggc ccgctga                                       3627
```

<210> SEQ ID NO 19
<211> LENGTH: 3627
<212> TYPE: DNA
<213> ORGANISM: Homo sapiens

<400> SEQUENCE: 19

```
atggagcggc tgcgggacgt gcgggagcgg ctgcaggcgt gggagcgcgc gttccgacgg     60

cagcgcgggc ggcgaccgag ccaggacgac gtggaggcgg cgccggagga gacccgcgcg    120

ctctaccggg agtaccgcac tctgaagcgt accacgggcc aggccggcgg cgggctccgc    180

agctccgagt cgctccccgc ggcggccgaa gaggcgccag agccccgctg ctgggggccc    240

catctgaatc gggctgcgac caagagtcca cagcctacgc cagggcggag ccgccagggc    300

tcggtgccgg actacgggca gcggctcaag gccaatctga aaggcaccct gcaggccgga    360

ccagccctgg gccgcagacc gtggcctcta ggaagagcct catctaaggc atccacccca    420

aagcccccag gtacagggcc tgtcccctcc tttgcagaaa aagtcagtga tgagcctcca    480

cagctccctg agccccagcc aaggccaggc cggctccagc atctgcaggc atccctgagc    540

cagcggctgg gctccctaga tcctggctgg ttacagcgat gtcacagtga ggtcccagat    600

tttctggggg cccccaaagc ctgcaggcct gatctaggct cagaggaatc acaacttctg    660

atccctggtg agtcggctgt ccttggtcct ggtgctggct cccagggccc agaggcttca    720

gccttccaag aagtcagcat ccgtgtgggg agcccccagc ccagcagcag tggaggcgag    780

aagcggagat ggaacgagga gccctgggag agccccgcac aggtccagca ggagagcagc    840

caagctggac ccccatcgga gggggctggg gctgtagcag ttgaggaaga ccctccaggg    900

gaacctgtac aggcacagcc acctcagccc tgcagcagcc catcgaaccc caggtaccac    960

ggactcagcc cctccagtca agctagggct gggaaggctg agggcacagc ccccctgcac   1020

atcttccctc ggctggcccg ccatgacagg ggcaattacg tacggctcaa catgaagcag   1080

aaacactacg tgcggggccg ggcactccgt agcaggctcc tccgcaagca ggcatggaag   1140

cagaagtggc ggaagaaagg ggagtgtttt gggggtggtg gtgccacagt cacaaccaag   1200

gagtcttgtt tcctgaacga gcagttcgat cactgggcag cccagtgtcc ccggccagca   1260

agtgaggaag acacagatgc tgttgggcct gagccactgg ttccttcacc acaacctgta   1320

cctgaggtgc ccagcctgga ccccaccgtg ctgccactct actccctggg gccctcaggg   1380

cagttggcag agacgccggc tgaggtgttc caggccctgg agcagctggg gcaccaagcc   1440

tttcgccctg ggcaggagcg tgcagtcatg cggatcctgt ctggcatctc cacgctgctg   1500

gtgctgccta caggtgccgg caagtccctg tgctaccagc tcccagcgct gctctacagc   1560

cggcgcagcc cctgcctcac gttggtcgtc tctcccctgc tgtcactcat ggatgaccag   1620

gtgtctggcc tgccaccgtg tctcaaggcg gcctgcatac actcgggcat gaccaggaag   1680

caacgggaat ctgtcctgca gaagattcgg gcagcccagg tacacgtgct gatgctgaca   1740

cctgaggcac tggtgggggc gggaggcctc cctccagccg cacagctgcc tccagttgct   1800

tttgcctgca ttgatgaggc ccactgcctc tcccagtggt cccacaactt ccggccctgc   1860
```

tacctgcgcg tctgcaaggt gcttcgggag cgcatgggcg tgcactgctt cctgggcctc 1920
acagccacag ccacacgccg cactgccagt gacgtggcac agcacctggc tgtggctgaa 1980
gagcctgacc tccacgggcc agccccagtt cccaccaacc tgcacctttc cgtgtccatg 2040
gacagggaca cagaccaggc actgttgacg ctgctgcaag gcaaacgttt tcaaaacctc 2100
gattccatta tcatttactg caaccggcgc gaggacacag agcggatcgc tgcgctcctc 2160
cgaacctgcc tgcacgcagc ctgggtccca gggtctggag gtcgtgcccc caaaaccaca 2220
gccgaggcct accacgcggg catgtgcagc cgggaacggc ggcgggtaca gcgagccttc 2280
atgcagggcc agttgcgggt ggtggtggcc acggtggcct ttgggatggg gctggaccgg 2340
ccagatgtgc gggctgtgct gcatctgggg ctgcccccaa gcttcgagag ctacgtgcag 2400
gccgtgggcc gggccgggcg tgacgggcag cctgcccact gccacctctt cctgcagccc 2460
cagggcgaag acctgcgaga gctgcgcaga catgtgcacg ccgacagcac ggacttcctg 2520
gctgtgaaga ggctggtaca gcgcgtgttc ccagcctgca cctgcacctg caccaggccg 2580
ccctcggagc aggaaggggc cgtgggtggg gagaggcctg tgcccaagta ccccccctcaa 2640 gaggctgagc agcttagcca ccaagcagcc ccaggaccca gaagggtctg catgggccat 2700
gagcgggcac tcccaataca gcttaccgta caggctttgg acatgccgga ggaggccatc 2760
gagactttgc tgtgctacct ggagctgcac ccacaccact ggctggagct gctggcgacc 2820
acctataccc attgccgtct gaactgccct gggggccctg cccagctcca ggccctggcc 2880
cacaggtgtc ccccttttggc tgtgtgcttg gcccagcagc tgcctgagga cccagggcaa 2940
ggcagcagct ccgtggagtt tgacatggtc aagctggtgg actccatggg ctgggagctg 3000
gcctctgtgc ggcgggctct ctgccagctg cagtgggacc acgagcccag gacaggtgtg 3060
cggcgtggga caggggtgct tgtggagttc agtgagctgg ccttccacct tcgcagcccg 3120
ggggacctga ccgctgagga gaaggaccag atatgtgact tcctctatgg ccgtgtgcag 3180
gcccgggagc gccaggccct ggcccgtctg cgcagaacct tccaggcctt tcacagcgta 3240
gccttcccca gctgcgggcc ctgcctggag cagcaggatg aggagcgcag caccaggctc 3300
aaggacctgc tcggccgcta ctttgaggaa gaggaagggc aggagccggg aggcatggag 3360
gacgcacagg gccccgagcc agggcaggcc agactccagg attgggagga ccaggtccgc 3420
tgcgacatcc gccagttcct gtccctgagg ccagaggaga agttctccag cagggctgtg 3480
gcccgcatct tccacggcat cggaagcccc tgctacccgg cccaggtgta cgggcaggac 3540
cgacgcttct ggagaaaata cctgcacctg agcttccatg ccctggtggg cctggccacg 3600
gaagagctcc tgcaggtggc ccgctga 3627

<210> SEQ ID NO 20
<211> LENGTH: 3921
<212> TYPE: DNA
<213> ORGANISM: Homo sapiens

<400> SEQUENCE: 20
cccacgcgtc cgcggctgcg cgggagattc gctggacgat cgcaagcgcg gaggccgggc 60
gggcgcgcgc gccatggagc ggctgcggga cgtgcgggag cggctgcagg cgtgggagcg 120
cgcgttccga cggcagcgcg ggcggcgacc gagccaggtg cgggctgccc aggggccgag 180
gggctgaggg cgcggcccgc ggctgacgcg ttccctttac aggacgacgt ggaggcggcg 240
ccggaggaga cccgcgcgct ctaccgggag taccgcactc tgaagcgtac cacgggccag 300
gccggcggcg ggctccgcag ctccgagtcg ctccccgcgg cggccgaaga ggcgccagag 360

-continued

```
ccccgctgct gggggcccca tctgaatcgg gctgcgacca agagtccaca gcctacgcca    420
gggcggagcc gccagggctc ggtgccggac tacgggcagc ggctcaaggc caatctgaaa    480
ggcaccctgc aggccggacc agccctgggc cgcagaccgt ggcctctagg aagagcctca    540
tctaaggcat ccaccccaaa gcccccaggt acagggcctg tcccctcctt tgcagaaaaa    600
gtcagtgatg agcctccaca gctccctgag ccccagccaa ggccaggccg gctccagcat    660
ctgcaggcat ccctgagcca gcggctgggc tccctagatc ctggctggtt acagcgatgt    720
cacagtgagg tcccagattt tctgggggcc cccaaagcct gcaggcctga tctaggctca    780
gaggaatcac aacttctgat ccctggtgag tcggctgtcc ttggtcctgg tgctggctcc    840
cagggcccag aggcttcagc cttccaagaa gtcagtatcc gtgtggggag cccccagccc    900
agcagcagtg gaggcgagaa gcggagatgg aacgaggagc cctgggagag ccccgcacag    960
gtccagcagg agagcagcca agctggaccc ccatcggagg gggctggggc tgtagcagtt   1020
gaggaagacc ctccagggga acctgtacag gcacagccac ctcagccctg cagcagccca   1080
tcgaacccca ggtaccacgg actcagcccc tccagtcaag ctagggctgg gaaggctgag   1140
ggcacagccc ccctgcacat cttccctcgg ctggcccgcc atgacagggg caattacgta   1200
cggctcaaca tgaagcagaa acactacgtg cggggccggg cactccgtag caggctcctc   1260
cgcaagcagg catggaagca gaagtggcgg aagaaagggg agtgttttgg gggtggtggt   1320
gccacagtca caaccaagga gtcttgtttc ctgaacgagc agttcgatca ctgggcagcc   1380
cagtgtcccc ggccagcaag tgaggaagac acagatgctg ttgggcctga gccactggtt   1440
ccttcaccac aacctgtacc tgaggtgccc agcctggacc ccaccgtgct gccactctac   1500
tccctggggc cctcagggca gttggcagag acgccggctg aggtgttcca ggccctggag   1560
cagctggggc accaagcctt tcgccctggg caggagcgtg cagtcatgcg gatcctgtct   1620
ggcatctcca cgctgctggt gctgcctaca ggtgccggca agtccctgtg ctaccagctc   1680
ccagcgctgc tctacagccg gcgcagcccc tgcctcacgt tggtcgtctc tcccctgctg   1740
tcactcatgg atgaccaggt gtctggcctg ccaccgtgtc tcaaggcggc ctgcatacac   1800
tcgggcatga ccaggaagca acgggaatct gtcctgcaga agattcgggc agcccaggta   1860
cacgtgctga tgctgacacc tgaggcactg gtgggggcgg gaggcctccc tccagccgca   1920
cagctgcctc cagttgcttt tgcctgcatt gatgaggccc actgcctctc ccagtggtcc   1980
cacaacttcc ggccctgcta cctgcgcgtc tgcaaggtgc ttcgggagcg catgggcgtg   2040
cactgcttcc tgggcctcac agccacagcc acacgcccac tgccagtgac gtggcacagc   2100
acctggctgt ggctgaagag cctgacctcc acgggccagc cccagttccc accaacctgc   2160
acctttccgt gtccatggac agggacacag accaggcact gttgacgctg ctgcaaggca   2220
aacgttttca aaacctcgat tccattatca tttactgcaa ccggcgcgag gacacagagc   2280
ggatcgctgc gctcctccga acctgcctgc acgcagcctg ggtcccaggg tctggaggtc   2340
gtgcccccaa aaccacagcc gaggcctacc acgcgggcat gtgcagccgg gaacggcggc   2400
gggtacagcg agccttcatg cagggccagt tgcgggtggt ggtggccacg gtggcctttg   2460
ggatggggct ggaccggcca gatgtgcggg ctgtgctgca tctggggctg cccccaagct   2520
tcgagagcta cgtgcaggcc gtgggccggg ccgggcgtga cgggcagcct gcccactgcc   2580
acctcttcct gcagccccag ggcgaagacc tgcgagagct gcgcagacat gtgcacgccg   2640
acagcacgga cttcctggct gtgaagaggc tggtacagcg cgtgttccca gcctgcacct   2700
gcacctgcac caggccgccc tcggagcagg aaggggccgt gggtggggag aggcctgtgc   2760
```

-continued

```
ccaagtaccc ccctcaagag gctgagcagc ttagccacca agcagcccca ggacccagaa   2820

gggtctgcat gggccatgag cgggcactcc caatacagct taccgtacag gctttggaca   2880

tgccggagga ggccatcgag actttgctgt gctacctgga gctgcaccca caccactggc   2940

tggagctgct ggcgaccacc tatacccatt gccgtctgaa ctgccctggg ggccctgccc   3000

agctccaggc cctggcccac aggtgtcccc ctttggctgt gtgcttggcc cagcagctgc   3060

ctgaggaccc agggcaaggc agcagctccg tggagtttga catggtcaag ctggtggact   3120

ccatgggctg ggagctggcc tctgtgcggc aggctctctg ccagctgcag tgggaccacg   3180

agcccaggac aggtgtgcgg cgtgggacag gggtgcttgt ggagttcagt gagctggcct   3240

tccaccttcg cagcccgggg gacctgaccg ctgaggagaa ggaccagata tgtgacttcc   3300

tctatggccg tgtgcaggcc cgggagcgcc aggccctggc ccgtctgcgc agaaccttcc   3360

aggcctttca cagcgtagcc ttccccagct gcgggccctg cctggagcag caggatgagg   3420

agcgcagcac caggctcaag gacctgctcg gccgctactt tgaggaagag gaagggcagg   3480

agccgggagg catggaggac gcacagggcc ccgagccagg gcaggccaga ctccaggatt   3540

gggaggacca ggtccgctgc gacatccgcc agttcctgtc cctgaggcca gaggagaagt   3600

tctccagcag ggctgtggcc cgcatcttcc acggcatcgg aagcccctgc tacccggccc   3660

aggtgtacgg gcaggaccga cgcttctgga gaaaatacct gcacctgagc ttccatgccc   3720

tggtgggcct ggccacggaa gagctcctgc aggtggcccg ctgactgcac tgcattgggg   3780

gatgtcgggt agagctgggg ttgtcagagg ctagggcagt gactgaggac ctgggcaaaa   3840

cctgccacag ggtgtgggaa cgaggaggct ccaaaatgca gaataaaaaa tgctcacttt   3900

gtttttaaaa aaaaaaaaaa a                                             3921
```

<210> SEQ ID NO 21
<211> LENGTH: 2398
<212> TYPE: DNA
<213> ORGANISM: Homo sapiens

<400> SEQUENCE: 21

```
ggcacgaggc tgaggtgttc caggccctgg agcagctggg gcaccaagcc tttcgccctg     60

ggcaggagcg tgcagtcatg cggatcctgt ctggcatctc cacgctgctg gtgctgccta    120

caggtgccgg caagtccctg tgctaccagc tcccagcgct gctctacagc cggcgcagcc    180

cctgcctcac gttggtcgtc tctcccctgc tgtcactcat ggatgaccag gtgtctggcc    240

tgccaccgtg tctcaaggcg gcctgcatac actcgggcat gaccaggaag caacgggaat    300

ctgtcctgca gaagattcgg gcagcccagg tacacgtgct gatgctgaca cctgaggcac    360

tggtgggggc gggaggcctc cctccagccg cacagctgcc tccagttgct tttgcctgca    420

ttgatgaggc ccactgcctc tcccagtggt cccacaactt ccggccctgc tacctgcgcg    480

tctgcaaggt gcttcgggag cgcatgggcg tgcactgctt cctgggcctc acagccacag    540

ccacacgccg cactgccagt gacgtggcac agcacctggc tgtggctgaa gagcctgacc    600

tccacgggcc agccccagtt cccaccaacc tgcacctttc cgtgtccatg gacagggaca    660

cagaccaggc actgttgacg ctgctgcaag gcaaacgttt tcaaaacctc gattccatta    720

tcatttactg caaccggcgc gaggacacag agcggatcgc tgcgctcctc cgaacctgcc    780

tgcacgcagc ctgggtccca gggtctggag gtcgtgcccc caaaaccaca gccgaggcct    840

accacgcggg catgtgcagc cgggaacggc ggcgggtaca gcgagccttc atgcagggcc    900

agttgcgggt ggtggtggcc acggtggcct ttgggatggg gctggaccgg ccagatgtgc    960
```

-continued

```
gggctgtgct gcatctgggg ctgcccccaa gcttcgagag ctacgtgcag gccgtgggcc   1020
gggccgggcg tgacgggcag cctgcccact gccacctctt cctgcagccc cagggcgaag   1080
acctgcgaga gctgcgcaga catgtgcacg ccgacagcac ggacttcctg gctgtgaaga   1140
ggctggtaca gcgcgtgttc ccagcctgca cctgcacctg caccaggccg ccctcggagc   1200
aggaaggggc cgtgggtggg gagaggcctg tgcccaagta ccccccctcaa gaggctgagc   1260
agcttagcca ccaagcagcc ccaggaccca gaagggtctg catgggccat gagcgggcac   1320
tcccaataca gcttaccgta caggctttgg acatgccgga ggaggccatc gagactttgc   1380
tgtgctacct ggagctgcac ccacaccact ggctggagct gctggcgacc acctataccc   1440
attgccgtct gaactgccct gggggccctg cccagctcca ggccctggcc cacaggtgtc   1500
cccctttggc tgtgtgcttg gcccagcagc tgcctgagga cccagggcaa ggcagcagct   1560
ccgtggagtt tgacatggtc aagctggtgg actccatggg ctgggagctg gcctctgtgc   1620
ggcgggctct ctgccagctg cagtgggacc acgagcccag gacaggtgtg cggcgtggga   1680
caggggtgct tgtggagttc agtgagctgg ccttccacct tcgcagcccg gggggacctga   1740
ccgctgagga gaaggaccag atatgtgact tcctctatgg ccgtgtgcag gcccgggagc   1800
gccaggccct ggcccgtctg cgcagaacct tccaggcctt tcacagcgta gccttcccca   1860
gctgcgggcc ctgcctggag cagcaggatg aggagcgcag caccaggctc aaggacctgc   1920
tcggccgcta ctttgaggaa gaggaagggc aggagccggg aggcatggag gacgcacagg   1980
gccccgagcc agggcaggcc agactccagg attgggagga ccaggtccgc tgcgacatcc   2040
gccagttcct gtccctgagg ccagaggaga agttctccag cagggctgtg gcccgcatct   2100
tccacggcat cggaagcccc tgctacccgg cccaggtgta cgggcaggac cgacgcttct   2160
ggagaaaata cctgcacctg agcttccatg ccctggtggg cctggccacg gaagagctcc   2220
tgcaggtggc ccgctgactg cactgcattg gggggatgtcg ggtagagctg gggttgtcag   2280
aggctagggc agtgactgag gacctgggca aaacctgcca cagggtgtgg gaacgaggag   2340
gctccaaaat gcagaataaa aaatgctcac tttgtttttta aaaaaaaaaa aaaaaaaa     2398
```

<210> SEQ ID NO 22
<211> LENGTH: 2146
<212> TYPE: DNA
<213> ORGANISM: Homo sapiens

<400> SEQUENCE: 22

```
ggcacgaggc tcgggcatga ccaggaagca acgggaatct gtcctgcaga agattcgggc     60
agcccaggta cacgtgctga tgctgacacc tgaggcactg gtgggggcgg gaggcctccc    120
tccagccgca cagctgcctc cagttgcttt tgcctgcatt gatgaggccc actgcctctc    180
ccagtggtcc cacaacttcc ggccctgcta cctgcgcgtc tgcaaggtgc ttcgggagcg    240
catgggcgtg cactgcttcc tgggcctcac agccacagcc acacgccgca ctgccagtga    300
cgtggcacag cacctggctg tggctgaaga gcctgacctc cacgggccag ccccagttcc    360
caccaacctg cacctttccg tgtccatgga cagggacaca gaccaggcac tgttgacgct    420
gctgcaaggc aaacgttttc aaaacctcga ttccattatc atttactgca accggcgcga    480
ggacacagag cggatcgctg cgctcctccg aacctgcctg cacgcagcct gggtcccagg    540
gtctggaggt cgtgccccca aaaccacagc cgaggcctac cacgcgggca tgtgcagccg    600
ggaacggcgg cgggtacagc gagccttcat gcagggccag ttgcgggtgg tggtggccac    660
ggtggccttt gggatggggc tggaccggcc agatgtgcgg gctgtgctgc atctggggct    720
```

gcccccaagc ttcgagagct acgtgcaggc cgtgggccgg gccgggcgtg acgggcagcc 780
tgcccactgc cacctcttcc tgcagcccca gggcgaagac ctgcgagagc tgcgcagaca 840
tgtgcacgcc gacagcacgg acttcctggc tgtgaagagg ctggtacagc gcgtgttccc 900
agcctgcacc tgcacctgca ccaggccgcc ctcggagcag gaaggggccg tgggtgggga 960
gaggcctgtg cccaagtacc cccctcaaga ggctgagcag cttagccacc aagcagcccc 1020
aggacccaga agggtctgca tgggccatga gcgggcactc ccaatacagc ttaccgtaca 1080
ggctttggac atgccggagg aggccatcga gactttgctg tgctacctgg agctgcaccc 1140
acaccactgg ctggagctgc tggcgaccac ctatacccat tgccgtctga actgccctgg 1200
gggccctgcc cagctccagg ccctggccca caggtgtccc cctttggctg tgtgcttggc 1260
ccagcagctg cctgaggacc cagggcaagg cagcagctcc gtggagtttg acatggtcaa 1320
gctggtggac tccatgggct gggagctggc ctctgtgcgg cgggctctct gccagctgca 1380
gtgggaccac gagcccagga caggtgtgcg gcgtgggaca ggggtgcttg tggagttcag 1440
tgagctggcc ttccaccttc gcagcccggg ggacctgacc gctgaggaga aggaccagat 1500
atgtgacttc ctctatggcc gtgtgcaggc ccgggagcgc caggccctgg cccgtctgcg 1560
cagaaccttc caggcctttc acagcgtagc cttccccagc tgcgggccct gcctggagca 1620
gcaggatgag gagcgcagca ccaggctcaa ggacctgctc ggccgctact ttgaggaaga 1680
ggaagggcag gagccgggag gcatggagga cgcacagggc cccgagccag ggcaggccag 1740
actccaggat tgggaggacc aggtccgctg cgacatccgc cagttcctgt ccctgaggcc 1800
agaggagaag ttctccagca gggctgtggc ccgcatcttc cacggcatcg gaagcccctg 1860
ctacccggcc caggtgtacg ggcaggaccg acgcttctgg agaaaatacc tgcacctgag 1920
cttccatgcc ctggtgggcc tggccacgga agagctcctg caggtggccc gctgactgca 1980
ctgcattggg ggatgtcggg tagagctggg gttgtcagag gctagggcag tgactgagga 2040
cctgggcaaa acctgccaca gggtgtggga acgaggaggc tccaaaatgc agaataaaaa 2100
atgctcactt tgtttttatg ggaaaaaaaa aaaaaaaaaa aaaaaa 2146

<210> SEQ ID NO 23
<211> LENGTH: 3715
<212> TYPE: DNA
<213> ORGANISM: Homo sapiens

<400> SEQUENCE: 23
acggatataa gattgcgtgg gttctgccta aagctgaatt cccagcgctt tggcttctct 60
gagttggggt tgtgtatagg ggtcttcgaa cagttccgga accagccagc agcctttaat 120
tcttgggcgg accacggccg gttctgtgtt cttggctaag atgagcagcc accataccac 180
ctttcctttt gaccctgagc ggcgagtccg gagtacgctg aagaaggtct ttgggtttga 240
ctcttttaag acgcctttac aggagagtgc gaccatggct gtagtaaaag gtaacaagga 300
cgtctttgtg tgcatgccca caggggcagg aaaatcccta tgctatcagc tccctgctct 360
gttggccaaa ggcatcacca ttgtagtctc tcctctcatt gctttgattc aggaccaagt 420
ggaccacttg ctaaccctaa aggtacgagt aagttccctg aactcgaagc tctctgcaca 480
ggaaaggaag gagctgcttg ctgacctgga gcgagaaaag ccccagacca agattctgta 540
catcacccca gagatggcag cttcatcctc cttccagccc accctgaact ccctggtgtc 600
ccgccacctg ctgtcttact tggtggtgga tgaagctcat tgtgtttccc aatgggggca 660
tgactttcgt cctgactact tgcgtctggg tgccctgcgc tcccgcctgg gacatgcccc 720

-continued

```
ttgtgtggct ctgaccgcca cagccacccc acaggtccaa gaggacgtgt ttgctgccct    780

gcacctgaag aaaccagttg ccatcttcaa gactccctgc ttccgggcca acctcttcta    840

tgatgtgcaa ttcaaggaac tgatttctga tccctatggg aacctgaagg acttctgcct    900

taaggctctt ggacaggagg ctgataaagg gttatctggc tgcggcattg tgtactgcag    960

gactagagag gcttgtgaac agctggccat agagctcagc tgcaggggtg tgaacgccaa   1020

ggcttaccat gcagggctga aggcctctga aagaacgctg gtgcagaacg actggatgga   1080

ggagaaggtc cctgtaattg ttgcaaccat tagttttggg atgggagtgg ataaagccaa   1140

tgtcaggttt gtcgcccatt ggaatattgc caagtctatg gctgggtact accaggagtc   1200

tggccgggct ggcagggatg ggaagccttc ctggtgccgt ctctattact ccaggaatga   1260

ccgggaccaa gtcagcttcc tgatcaggaa ggaagtagca aaactccagg aaaagagagg   1320

aaacaaagca tctgataaag ccactatcat ggcctttgat gccctggtga ccttctgtga   1380

agaactgggg taagtgactt attttatatg tggagcaaag tgtcagtgag atcatttact   1440

tccccggcac gccctagtta agcagctgac ataagacagc ccgtaggcta ccaagggaca   1500

cctgcctgca aaggccattg tgtcgggcag tgtggaagtc aggaccttgc tcttctctat   1560

tggaggcccc gggatctctc gcagtgtggg gatttgctca gtattctgag tggtgtcctt   1620

ccctccactc caccctcttc tgggatggct ggccccacaa gccactcagt tccaagggat   1680

gtgaccagct ctgagccatc ggctttgtgg tcatcatgtt ccacccgagc tgggacttct   1740

ggcatcactt gagttatcct cacccttatc caggacccaa caacagaagc ctgtggcccc   1800

aacttacctc ggggagtcat gtgctttgaa ctcaacgcat ctgttttacc tgcatctgca   1860

ggcgatgggg caggggccac gggaagagtc tgagggctgc ttggtgtagt caggttgtgt   1920

ccaggcatgc ggagctgtga gtgcctgcag gagagacacc caggaggagt ttttacattt   1980

tggtctaaaa agctcttgga ttcatctcat ctcatggaat gatcctgtcg gatgacgctg   2040

acgtgattgc ttcagactta gaggtgaata aattgaggtc cagagaggtc acagtcacga   2100

agctcatggt agactgaggc cactaaacac ccgtctcctg attttcagtg gcgtcctcat   2160

ttgcatacac ctgggccatc ttggtttttg caagaaaaaa gcgaggaaat cagagaaact   2220

ctttgggctg tgtgttttta tttccacctc ctcctgttga ccagtgagtc ggtggcttct   2280

ggactgaagc tattttcttc tccaaactgc tgtctctaat ttggcctctg tggcaagacc   2340

acgcccagca aaagtggtcg gctgcagtgc caggaccacc cttgcctgca gcctttgcga   2400

ccagagccct tttcaagcac aattaatatg ggagttgcta aatttggcct tcttaggctt   2460

cttgagcaga gctcttattt ctggtgagga atgaaagggc caagtgttcc tgttcattgt   2520

gagtcctgtt tgctgaaaaa agctctgggg ctgtctgagg ctctggaatg ctctctggag   2580

ggttaactct gcctgtcccc agggtctgct ccgcctgcca ggcaagggaa caggtcctcc   2640

caagggcctc tgccttcatt tctcctgtca ccttccgggg agctgggact tcttagtgca   2700

tcagtggcct ggttgccagg ggctggggtc caggcatctg tggactcaag gagtccaggt   2760

gacggtgttg cgctgcctct tgagcagcct cgtgcctgtc tcctttgcta catgtgatga   2820

ttctgaaatc caggcagcag gctggaataa acgctgctgg tatgtctgta ttggctactg   2880

ttctttgaat aagtgaatgt ttctttattg cataactggc gtgtagcaca aagaaaaagc   2940

cccttctcca ccagatattt gcttcctaag aatagttctc attggaggct gaggtcgaag   3000

cagcctccca ccagcgatcc cttggggcgg gcacctggca gtgagggaca gagctagtgg   3060

ggtgggctca gcagaagtgg gtgcatttct gcaaaggaag ctgtaggttt cttgtcagtt   3120
```

-continued

```
tgttgtgggg tctgaggcac atgggagtgg gaccagcaga aaagatactc aggtcagtta   3180

actaatgagg cggggctgtg gcagccagcg gttttcctct cttctctatc tgtagctact   3240

ttctctgggc tgcagccttg aaaaagcagt gtttgattat tcataacaat gagtgtcttt   3300

tagtgtcaca gggaacagtt attaggtttg aagcaacctc cagcttgagg cctcggcatc   3360

ttgagatgga agagcagcct tgtgtttaga cctggattga attgggccct gttgtttcct   3420

gggatcttgg ggctgggggt gcccaacagc ctggcatctt cttgtttctc tgtgtgttta   3480

ctcattcatt catttattca gctgataaat attgactgat gccagctctg tgccagacac   3540

attggacatg ggggatacac tagtgggcag aaatagcccc gtcccagagc cggccatggt   3600

ggctcatacc tgttatacca gcactttggg aggctgaagt gggaggatcg cttgagcctg   3660

ggagttcaag accagcctgg gcaacatggc aagaccctgt ctctactaaa aatac        3715
```

<210> SEQ ID NO 24
<211> LENGTH: 1740
<212> TYPE: DNA
<213> ORGANISM: Homo sapiens

<400> SEQUENCE: 24

```
agattgcgtg ggttctgcct aaagctgaat tcccagcgct ttggcttctc tgagttgggg     60

ttgtgtatag gggtcttcga acagttccgg aaccagccag cagcctttaa ttcttgggcg    120

gaccacggcc ggttctgtgt tcttggctaa gatgagcagc caccatacca cctttccttt    180

tgaccctgag cggcgagtcc ggagtacgct gaagaaggtc tttgggtttg actcttttaa    240

gacgccttta caggagagtg cgaccatggc tgtagtaaaa ggtaacaagg acgtctttgt    300

gtgcatgccc acaggggcag gaaaatccct atgctatcag ctccctgctc tgttggccaa    360

aggcaacacc attgtagtct ctcctctcat tgctttgatt caggaccaag tggaccactt    420

gctaacccta aaggtacgag taagttccct gaactcgaag ctctctgcac aggaaaggaa    480

ggagctgctt gctgacctgg agcgagaaaa gccccagacc aagattctgt acatcacccc    540

agagatggca gcttcatcct ccttccagcc caccctgaac tccctggtgt cccgccacct    600

gctgtcttac ttggtggtgg atgaagctca ttgtgtttcc caatgggggc atgactttcg    660

tcctgactac ttgcgtctgg gtgccctgcg ctcccgcctg ggacatgccc cttgtgtggc    720

tctgaccgcc acagccaccc cacaggtcca agaggacgtg tttgctgccc tgcacctgaa    780

gaaaccagtt gccatcttca agactccctg cttccgggcc aacctcttct atgatgtgca    840

attcaaggaa ctgatttctg atccctatgg gaacctgaag gacttctgcc ttaaggctct    900

tggacaggag gctgataaag ggttatctgg ctgcggcatt gtgtactgca ggactagaga    960

ggcttgtgaa cagctggcca tagagctcag ctgcaggggt gtgaacgcca aggcttacca   1020

tgcagggctg aaggcctctg aaagaacgct ggtgcagaac gactggatgg aggagaaggt   1080

ccctgtaatt gttgcaacca ttagttttgg gatgggagtg gataaagcca atgtcaggtt   1140

tgtcgcccat tggaatattg ccaagtctat ggctgggtac taccaggagt ctggccgggc   1200

tggcagggat gggaagcctt cctggtgccg tctctattac tccaggaatg accgggacca   1260

agtcagcttc ctgatcagga aggaagtagc aaaactccag gaaaagagag gaaacaaagc   1320

atctgataaa gccactatca tggcctttga tgccctggtg accttctgtg aagaactggg   1380

gcgatggggc aggggccacg gaaagagtct gagggctgct tggtgtagtc aggttgtgtc   1440

caggcatgcg gagctgtgag tgcctgcagg agagacaccc aggaggagtt tttacatttt   1500

ggtctaaaaa gctcttggat tcatctcatc tcatggaatg atcctgtcgg atgacgctga   1560
```

cgtgattgct tcagacttag aggtgaataa attgaggtcc agagaggtca cagtcacgaa 1620
gctcatggta gactgaggcc actaaacacc cgtctcctga ttttcagtgg cgtcctcatt 1680
tgcatacacc tgggccatct tggtttttgc aagaaaaaag cgaggaaatc agagaaactc 1740

<210> SEQ ID NO 25
<211> LENGTH: 1233
<212> TYPE: DNA
<213> ORGANISM: Homo sapiens

<400> SEQUENCE: 25
atgagcagcc accataccac ctttcctttt gaccctgagc ggcgagtccg gagtacgctg 60
aagaaggtct ttgggtttga ctcttttaag acgcctttac aggagagtgc gaccatggct 120
gtagtaaaag gtaacaagga cgtctttgtg tgcatgccca caggggcagg aaaatcccta 180
tgctatcagc tccctgctct gttggccaaa ggcatcacca ttgtagtctc tcctctcatt 240
gctttgattc aggaccaagt ggaccacttg ctaaccctaa aggtacgagt aagttccctg 300
aactcgaagc tctctgcaca ggaaaggaag gagctgcttg ctgacctgga gcgagaaaag 360
ccccagacca agattctgta catcacccca gagatggcag cttcatcctc cttccagccc 420
accctgaact ccctggtgtc ccgccacctg ctgtcttact tggtggtgga tgaagctcat 480
tgtgtttccc aatgggggca tgactttcgt cctgactact tgcgtctggg tgccctgcgc 540
tcccgcctgg gacatgcccc ttgtgtggct ctgaccgcca cagccacccc acaggtccaa 600
gaggacgtgt ttgctgccct gcacctgaag aaaccagttg ccatcttcaa gactccctgc 660
ttccgggcca acctcttcta tgatgtgcaa ttcaaggaac tgatttctga tccctatggg 720
aacctgaagg acttctgcct taaggctctt ggacaggagg ctgataaagg gttatctggc 780
tgcggcattg tgtactgcag gactagagag gcttgtgaac agctggccat agagctcagc 840
tgcaggggtg tgaacgccaa ggcttaccat gcagggctga aggcctctga aagaacgctg 900
gtgcagaacg actggatgga ggagaaggtc cctgtaattg ttgcaaccat tagttttggg 960
atgggagtgg ataaagccaa tgtcaggttt gtcgcccatt ggaatattgc caagtctatg 1020
gctgggtact accaggagtc tggccgggct ggcagggatg ggaagccttc ctggtgccgt 1080
ctctattact ccaggaatga ccgggaccaa gtcagcttcc tgatcaggaa ggaagtagca 1140
aaactccagg aaaagagagg aaacaaagca tctgataaag ccactatcat ggcctttgat 1200
gccctggtga ccttctgtga agaactgggg taa 1233

<210> SEQ ID NO 26
<211> LENGTH: 1749
<212> TYPE: DNA
<213> ORGANISM: Homo sapiens

<400> SEQUENCE: 26
acggatataa gattgcgtgg gttctgccta aagctgaatt cccagcgctt tggcttctct 60
gagttggggt tgtgtatagg ggtcttcgaa cagttccgga accagccagc agcctttaat 120
tcttgggcgg accacggccg gttctgtgtt cttggctaag atgagcagcc accataccac 180
ctttcctttt gaccctgagc ggcgagtccg gagtacgctg aagaaggtct ttgggtttga 240
ctcttttaag acgcctttac aggagagtgc gaccatggct gtagtaaaag gtaacaagga 300
cgtctttgtg tgcatgccca caggggcagg aaaatcccta tgctatcagc tccctgctct 360
gttggccaaa ggcatcacca ttgtagtctc tcctctcatt gctttgattc aggaccaagt 420
ggaccacttg ctaaccctaa aggtacgagt aagttccctg aactcgaagc tctctgcaca 480
ggaaaggaag gagctgcttg ctgacctgga gcgagaaaag ccccagacca agattctgta 540
catcacccca gagatggcag cttcatcctc cttccagccc accctgaact ccctggtgtc 600
ccgccacctg ctgtcttact tggtggtgga tgaagctcat tgtgtttccc aatgggggca 660
tgactttcgt cctgactact tgcgtctggg tgccctgcgc tcccgcctgg gacatgcccc 720
ttgtgtggct ctgaccgcca cagccacccc acaggtccaa gaggacgtgt ttgctgccct 780
gcacctgaag aaaccagttg ccatcttcaa gactccctgc ttccgggcca acctcttcta 840
tgatgtgcaa ttcaaggaac tgatttctga tccctatggg aacctgaagg acttctgcct 900
taaggctctt ggacaggagg ctgataaagg gttatctggc tgcggcattg tgtactgcag 960
gactagagag gcttgtgaac agctggccat agagctcagc tgcaggggtg tgaacgccaa 1020
ggcttaccat gcagggctga aggcctctga aagaacgctg gtgcagaacg actggatgga 1080
ggagaaggtc cctgtaattg ttgcaaccat tagttttggg atgggagtgg ataaagccaa 1140
tgtcaggttt gtcgcccatt ggaatattgc caagtctatg gctgggtact accaggagtc 1200
tggccgggct ggcagggatg ggaagccttc ctggtgccgt ctctattact ccaggaatga 1260
ccgggaccaa gtcagcttcc tgatcaggaa ggaagtagca aaactccagg aaaagagagg 1320
aaacaaagca tctgataaag ccactatcat ggcctttgat gccctggtga ccttctgtga 1380
agaactgggg cgatggggca ggggccacgg gaagagtctg agggctgctt ggtgtagtca 1440
ggttgtgtcc aggcatgcgg agctgtgagt gcctgcagga gagacaccca ggaggagttt 1500
ttacattttg gtctaaaaag ctcttggatt catctcatct catggaatga tcctgtcgga 1560
tgacgctgac gtgattgctt cagacttaga ggtgaataaa ttgaggtcca gagaggtcac 1620
agtcacgaag ctcatggtag actgaggcca ctaaacaccc gtctcctgat tttcagtggc 1680
gtcctcattt gcatacacct gggccatctt ggtttttgca agaaaaaagc gaggaaatca 1740
gagaaactc 1749

<210> SEQ ID NO 27
<211> LENGTH: 3703
<212> TYPE: DNA
<213> ORGANISM: Homo sapiens

<400> SEQUENCE: 27
acggatataa gattgcgtgg gttctgccta aagctgaatt cccagcgctt tggcttctct 60
gagttggggt tgtgtatagg ggtcttcgaa cagttccgga accagccagc agcctttaat 120
tcttgggcgg accacggccg gttctgtgtt cttggctaag atgagcagcc accataccac 180
ctttcctttt gaccctgagc ggcgagtccg gagtacgctg aagaaggtct ttgggtttga 240
ctcttttaag acgcctttac aggagagtgc gaccatggct gtagtaaaag gtaacaagga 300
cgtctttgtg tgcatgccca caggggcagg aaaatcccta tgctatcagc tccctgctct 360
gttggccaaa ggcatcacca ttgtagtctc tcctctcatt gctttgattc aggaccaagt 420
ggaccacttg ctaaccctaa aggtacgagt aagttccctg aactcgaagc tctctgcaca 480
ggaaaggaag gagctgcttg ctgacctgga gcgagaaaag ccccagacca agattctgta 540
catcacccca gagatggcag cttcatcctc cttccagccc accctgaact ccctggtgtc 600
ccgccacctg ctgtcttact tggtggtgga tgaagctcat tgtgtttccc aatgggggca 660
tgactttcgt cctgactact tgcgtctggg tgccctgcgc tcccgcctgg gacatgcccc 720
ttgtgtggct ctgaccgcca cagccacccc acaggtccaa gaggacgtgt ttgctgccct 780
gcacctgaag aaaccagttg ccatcttcaa gactccctgc ttccgggcca acctcttcta 840

-continued

```
tgatgtgcaa ttcaaggaac tgatttctga tccctatggg aacctgaagg acttctgcct    900

taaggctctt ggacaggagg ctgataaagg gttatctggc tgcggcattg tgtactgcag    960

gactagagag gcttgtgaac agctggccat agagctcagc tgcaggggtg tgaacgccaa   1020

ggcttaccat gcagggctga aggcctctga aagaacgctg gtgcagaacg actggatgga   1080

ggagaaggtc cctgtaattg ttgcaaccat tagttttggg atgggagtgg ataaagccaa   1140

tgtcaggttt gtcgcccatt ggaatattgc caagtctatg gctgggtact accaggagtc   1200

tggccgggct ggcagggatg ggaagccttc ctggtgccgt ctctattact ccaggaatga   1260

ccgggaccaa gtcagcttcc tgatcaggaa ggaagtagca aaactccagg aaaagagagg   1320

aaacaaagca tctgataaag ccactatcat ggcctttgat gccctggtga ccttctgtga   1380

agaactgggg tgccgccatg ccgccattgc caagtacttc ggggatgcgc tgcctgcctg   1440

cgccaaaggc tgcgaccact gccagaaccc cacggccgtg cggaggcggc tggaggcctt   1500

ggagcgcagc agcagctgga gcaagacctg catcgggccc tcccagggga acggctttga   1560

ccccgagctg tacgagggag gccgcaaggg ctacggggac ttcagcaggt atgacgaagg   1620

ttctggaggc agcggggatg aaggcagaga tgaggcccac aagcgggagt ggaacctctt   1680

ctatcagaag cagatgcagc tgcgcaaggg caaagacccc aagatagaag aatttgtacc   1740

cccagatgag aactgtcccc tgaaagaggc ttctagcagg aggatcccca ggctgactgt   1800

gaaggcacgg gagcactgcc tgcggcttct ggaggaggcg ctgagcagca accgccagtc   1860

aacacgtacc gctgatgaag ctgacctccg ggccaaggcc gtggagctgg aacatgagac   1920

attccggaac gccaaggtgg ccaacctcta caaggccagc gtgctgaaga aggtggccga   1980

tatccacaga gcctccaagg atgggcagcc ctatgacatg ggaggcagtg ccaagagctg   2040

cagtgcccaa gctgagcccc cggagcccaa tgagtatgac attccaccag cctcccatgt   2100

gtactcgctc aaacccaagc gggtgggagc tggtttcccc aaaggctcct gcccgttcca   2160

gacggccacg gaactgatgg agacgactcg gatcagggag caagcccccc agcccgagcg   2220

gggaggcgag cacgagcccc cgagccggcc ctgtggcctc ctggatgagg atgggagtga   2280

gcccctccct gggcccagag gggaggtccc tggaggcagc gctcactatg gggggccctc   2340

ccctgagaag aaggcaaaaa gttcctctgg gggcagctcc cttgccaagg gccgggctag   2400

caagaaacag cagctcctag ccacagcggc ccacaaggat tctcagagca tcgcccgctt   2460

cttctgccga agggtggaaa gcccagctct gctggcatca gccccagagg cagaaggtgc   2520

ctgcccctcc tgtgaggggg ttcagggacc cccgatggcc ccagagaagt acacagggga   2580

ggaagatgga gccgggggac attcgcctgc cctcccccag actgaggagt gcctcaggga   2640

gaggccaagc acctgcccgc ccagagacca gggcacccct gaagtccagc ccacccctgc   2700

aaaggacaca tggaagggca agcggcctcg atcccagcag gagaacccag agagccagcc   2760

tcagaagagg ccacgcccct cagccaagcc ctccgtcgta gctgaggtca agggcagcgt   2820

ctcggccagc gaacagggca ccttgaatcc cacggctcaa gacccettcc agctctccgc   2880

tcctggcgtc tccttgaagg aggctgcaaa tgttgtggtc aagtgcctca ccccttteta   2940

caaggagggc aagtttgctt ccaaggagtt gtttaaaggc tttgcccgcc acctctcaca   3000

cttgctgact cagaagacct ctcctggaag gagcgtgaaa gaagaggccc agaacctcat   3060

caggcacttc ttccatggcc gggcccggtg cgagagcgaa gctgactggc atggcctgtg   3120

tggcccccag agatgaccaa ctgctggctg ggcagggccc gcgtcctccc ccagattcta   3180

gcatgggtca tcctgggcct cacctgctga tgccagggcc atcgtctttt ctcagtcctt   3240
```

-continued

```
ctcctttcca accatacttg gctttgggga tgaccccaga cacccccctga atccaggtca   3300

gaggtcagcc cacctttctt tctgcttgca aagcctatag acccttctca gagcggtcct   3360

catggctggg ttttctggga cacatgtcga ggacagaagg tggagggtgg tggagctgct   3420

gctggaagaa ggggaaggaa gagtggcccc tccccgagtt ctaagtcagg atgaggccca   3480

cctgtccaag gtatcggaac ctacccaggg gaccctcaga tcctccaccc actcccccat   3540

ccattacgat gccagcttcc agccttgccc aggtcagagc tgtggcagag gagaggcagc   3600

caggccctgt tcctgctcag ctcctgctca ggaaggccag gcctgacaga tgtttgggag   3660

aggaataaag ttgtgttgtt gtggggcatg caggcgtgca cac                      3703
```

<210> SEQ ID NO 28
<211> LENGTH: 3715
<212> TYPE: DNA
<213> ORGANISM: Homo sapiens

<400> SEQUENCE: 28

```
acggatataa gattgcgtgg gttctgccta aagctgaatt cccagcgctt tggcttctct     60

gagttggggt tgtgtatagg ggtcttcgaa cagttccgga accagccagc agcctttaat    120

tcttgggcgg accacggccg gttctgtgtt cttggctaag atgagcagcc accataccac    180

ctttcctttt gaccctgagc ggcgagtccg gagtacgctg aagaaggtct ttgggtttga    240

ctcttttaag acgcctttac aggagagtgc gaccatggct gtagtaaaag gtaacaagga    300

cgtctttgtg tgcatgccca caggggcagg aaaatcccta tgctatcagc tccctgctct    360

gttggccaaa ggcatcacca ttgtagtctc tcctctcatt gctttgattc aggaccaagt    420

ggaccacttg ctaaccctaa aggtacgagt aagttccctg aactcgaagc tctctgcaca    480

ggaaaggaag gagctgcttg ctgacctgga gcgagaaaag ccccagacca agattctgta    540

catcacccca gagatggcag cttcatcctc cttccagccc accctgaact ccctggtgtc    600

ccgccacctg ctgtcttact tggtggtgga tgaagctcat tgtgtttccc aatgggggca    660

tgactttcgt cctgactact tgcgtctggg tgccctgcgc tcccgcctgg gacatgcccc    720

ttgtgtggct ctgaccgcca cagccacccc acaggtccaa gaggacgtgt ttgctgccct    780

gcacctgaag aaaccagttg ccatcttcaa gactccctgc ttccgggcca acctcttcta    840

tgatgtgcaa ttcaaggaac tgatttctga tccctatggg aacctgaagg acttctgcct    900

taaggctctt ggacaggagg ctgataaagg gttatctggc tgcggcattg tgtactgcag    960

gactagagag gcttgtgaac agctggccat agagctcagc tgcaggggtg tgaacgccaa   1020

ggcttaccat gcagggctga aggcctctga aagaacgctg gtgcagaacg actggatgga   1080

ggagaaggtc cctgtaattg ttgcaaccat tagttttggg atgggagtgg ataaagccaa   1140

tgtcaggttt gtcgcccatt ggaatattgc caagtctatg gctgggtact accaggagtc   1200

tggccgggct ggcagggatg ggaagccttc ctggtgccgt ctctattact ccaggaatga   1260

ccgggaccaa gtcagcttcc tgatcaggaa ggaagtagca aaactccagg aaaagagagg   1320

aaacaaagca tctgataaag ccactatcat ggcctttgat gccctggtga ccttctgtga   1380

agaactgggg taagtgactt attttatatg tggagcaaag tgtcagtgag atcatttact   1440

tccccggcac gccctagtta agcagctgac ataagacagc ccgtaggcta ccaagggaca   1500

cctgcctgca aaggccattg tgtcgggcag tgtggaagtc aggaccttgc tcttctctat   1560

tggaggcccc gggatctctc gcagtgtggg gatttgctca gtattctgag tggtgtcctt   1620

ccctccactc caccctcttc tgggatggct ggccccacaa gccactcagt tccaagggat   1680
```

-continued gtgaccagct ctgagccatc ggctttgtgg tcatcatgtt ccacccgagc tgggacttct 1740
ggcatcactt gagttatcct caccccttatc caggacccaa caacagaagc ctgtggcccc 1800
aacttacctc ggggagtcat gtgctttgaa ctcaacgcat ctgttttacc tgcatctgca 1860
ggcgatgggg caggggccac gggaagagtc tgagggctgc ttggtgtagt caggttgtgt 1920
ccaggcatgc ggagctgtga gtgcctgcag gagagacacc caggaggagt ttttacattt 1980
tggtctaaaa agctcttgga ttcatctcat ctcatggaat gatcctgtcg gatgacgctg 2040
acgtgattgc ttcagactta gaggtgaata aattgaggtc cagagaggtc acagtcacga 2100
agctcatggt agactgaggc cactaaacac ccgtctcctg attttcagtg gcgtcctcat 2160
ttgcatacac ctgggccatc ttggtttttg caagaaaaaa gcgaggaaat cagagaaact 2220
ctttgggctg tgtgttttta tttccacctc ctcctgttga ccagtgagtc ggtggcttct 2280
ggactgaagc tattttcttc tccaaactgc tgtctctaat ttggcctctg tggcaagacc 2340
acgcccagca aaagtggtcg gctgcagtgc caggaccacc cttgcctgca gcctttgcga 2400
ccagagccct tttcaagcac aattaatatg ggagttgcta aatttggcct tcttaggctt 2460
cttgagcaga gctcttattt ctggtgagga atgaaagggc caagtgttcc tgttcattgt 2520
gagtcctgtt tgctgaaaaa agctctgggg ctgtctgagg ctctggaatg ctctctggag 2580
ggttaactct gcctgtcccc agggtctgct ccgcctgcca ggcaagggaa caggtcctcc 2640
caagggcctc tgccttcatt tctcctgtca ccttccgggg agctgggact tcttagtgca 2700
tcagtggcct ggttgccagg ggctggggtc caggcatctg tggactcaag gagtccaggt 2760
gacggtgttg cgctgcctct tgagcagcct cgtgcctgtc tcctttgcta catgtgatga 2820
ttctgaaatc caggcagcag gctggaataa acgctgctgg tatgtctgta ttggctactg 2880
ttctttgaat aagtgaatgt ttctttattg cataactggc gtgtagcaca aagaaaaagc 2940
cccttctcca ccagatattt gcttcctaag aatagttctc attggaggct gaggtcgaag 3000
cagcctccca ccagcgatcc cttggggcgg gcacctggca gtgagggaca gagctagtgg 3060
ggtgggctca gcagaagtgg gtgcatttct gcaaaggaag ctgtaggttt cttgtcagtt 3120
tgttgtgggg tctgaggcac atgggagtgg gaccagcaga aaagatactc aggtcagtta 3180
actaatgagg cggggctgtg gcagccagcg gttttcctct cttctctatc tgtagctact 3240
ttctctgggc tgcagccttg aaaaagcagt gtttgattat tcataacaat gagtgtcttt 3300
tagtgtcaca gggaacagtt attaggtttg aagcaacctc cagcttgagg cctcggcatc 3360
ttgagatgga agagcagcct tgtgtttaga cctggattga attgggccct gttgtttcct 3420
gggatcttgg ggctgggggt gcccaacagc ctggcatctt cttgtttctc tgtgtgttta 3480
ctcattcatt catttattca gctgataaat attgactgat gccagctctg tgccagacac 3540
attggacatg ggggatacac tagtgggcag aaatagcccc gtcccagagc cggccatggt 3600
ggctcatacc tgttatacca gcactttggg aggctgaagt gggaggatcg cttgagcctg 3660
ggagttcaag accagcctgg gcaacatggc aagaccctgt ctctactaaa aatac 3715

<210> SEQ ID NO 29
<211> LENGTH: 3676
<212> TYPE: DNA
<213> ORGANISM: Homo sapiens

<400> SEQUENCE: 29
ctgaattccc agcgctttgg cttctctgag ttggggttgt gtataggggt cttcgaacag 60
ttccggaacc agccagcagc ctttaattct tgggcggacc acggccggtt ctgtgttctt 120

-continued

```
ggctaagatg agcagccacc ataccacctt tccttttgac cctgagcggc gagtccggag    180
tacgctgaag aaggtctttg ggtttgactc ttttaagacg cctttacagg agagtgcgac    240
catggctgta gtaaaaggta acaaggacgt ctttgtgtgc atgcccacag ggcaggaaa    300
atccctatgc tatcagctcc ctgctctgtt ggccaaaggc atcaccattg tagtctctcc    360
tctcattgct ttgattcagg accaagtgga ccacttgcta accctaaagg tacgagtaag    420
ttccctgaac tcgaagctct ctgcacagga aaggaaggag ctgcttgctg acctggagcg    480
agaaaagccc cagaccaaga ttctgtacat caccccagag atggcagctt catcctcctt    540
ccagcccacc ctgaactccc tggtgtcccg ccacctgctg tcttacttgg tggtggatga    600
agctcattgt gtttcccaat gggggcatga ctttcgtcct gactacttgc gtctgggtgc    660
cctgcgctcc cgcctgggac atgccccttg tgtggctctg accgccacag ccaccccaca    720
ggtccaagag gacgtgtttg ctgccctgca cctgaagaaa ccagttgcca tcttcaagac    780
tccctgcttc cgggccaacc tcttctatga tgtgcaattc aaggaactga tttctgatcc    840
ctatgggaac ctgaaggact tctgccttaa ggctcttgga caggaggctg ataaagggtt    900
atctggctgc ggcattgtgt actgcaggac tagagaggct tgtgaacagc tggccataga    960
gctcagctgc aggggtgtga acgccaaggc ttaccatgca gggctgaagg cctctgaaag   1020
aacgctggtg cagaacgact ggatggagga gaaggtccct gtaattgttg caaccattag   1080
ttttgggatg ggagtggata aagccaatgt caggtttgtc gcccattgga atattgccaa   1140
gtctatggct gggtactacc aggagtctgg ccgggctggc agggatggga agccttcctg   1200
gtgccgtctc tattactcca ggaatgaccg ggaccaagtc agcttcctga tcaggaagga   1260
agtagcaaaa ctccaggaaa agagaggaaa caaagcatct gataaagcca ctatcatggc   1320
ctttgatgcc ctggtgacct tctgtgaaga actggggtaa gtgacttatt ttatatgtgg   1380
agcaaagtgt cagtgagatc atttacttcc ccggcacgcc ctagttaagc agctgacata   1440
agacagcccg taggctacca agggacacct gcctgcaaag gctgttgtgt cgggcagtgt   1500
ggaagtcagg accttgctct tctctattgg aggccccggg atctctcgca gtgtggggat   1560
ttgctcagta ttctgagtgg tgtccttccc tccactccac cctcttctgg gatggctggc   1620
cccacaagcc actcagttcc aagggatgtg accagctctg agccatcggc tttgtggtca   1680
tcatgtgcca ccgagctggg acttctggca tcacttgagt agtcctcacc cttatccagg   1740
acccacacag aagcctgtgg ccccacttac ctcggggagt catgtgcttt gaactcacgc   1800
atctgtttta cctgcatctg caggcgatgg ggcaggggcc acggaaagag tctgagggct   1860
gcttggtgta gtcaggttgt gtccaggcat gcggagctgt gagtgcctgc aggagagaca   1920
cccaggagga gtttttacat tttggtctaa aaagctcttg gattcatctc atctcatgga   1980
atgatcctgt cggatgacgc tgacgtgatt gcttcagact tagaggtgaa taaattgagg   2040
tccagagagg tcacagtcac gaagctcatg gtagactgag gccactaaac acccgtctcc   2100
tgattttcag tggcgtcctc atttgcatac acctgggcca tcttggtttt tgcaagaaaa   2160
aagcgaggaa atcagagaac tctttgggct gtgtgttttt atttccacct cctcctgttg   2220
accagtgagt cggtggcttc tggactgaag ctattttctt ctccaaactg ctgtctctaa   2280
tttggcctct gtggcaagac cacgcccagc aaaagtggtc ggctgcagtg ccaggaccac   2340
ccttgcctgc agcctttgcg accagagccc ttttcaagca caattaatat gggagttgct   2400
aaatttggcc ttcttaggct tcttgagcag agctcttatt tctggtgagg aatgaaaggg   2460
ccaagtgttc ctgttcattg tgagtcctgt ttgctgaaaa aagctctggg gctgtctgag   2520
```

-continued

```
gctctggaat gctctctgga gggttaactc tgcctgtccc cagggtctgc tccgcctgcc   2580

aggcaaggga acaggtcctc ccaagggcct ctgccttcat ttctcctgtc accttccggg   2640

gagctgggac ttcttagtgc atcagtggcc tggttgccag gggctggggt ccaggcatct   2700

gtggactcaa ggagtccagg tgacggtgtt gcgctgcctc ttgagcagcc tcgtgcctgt   2760

ctcctttgct acatgtgatg attctgaaat ccaggcagca ggctggaata aacgctgctg   2820

gtatgtctgt attggctact gttctttgaa taagtgaatg tttctttatt gcataactgg   2880

cgtgtagcac aaagaaaaag ccccttctcc accagatatt tgcttcctaa gaatagttct   2940

cattggaggc tgaggtcgaa gcagcctccc accagcgatc ccttggggcg ggcacctggc   3000

agtgagggac agagctagtg gggtgggctc agcagaagtg ggtgcatttc tgcaaaggaa   3060

gctgtaggtt tcttgtcagt ttgttgtggg gtctgaggca catgggagtg ggaccagcag   3120

aaaagatact caggtcagtt aactaatgag gcggggctgt ggcagccagc ggttttcctc   3180

tcttctctat ctgtagctac tttctctggg ctgcagcctt gaaaaagcag tgtttgatta   3240

ttcataacaa tgagtgtctt ttagtgtcac agggaacagt tattaggttt gaagcaacct   3300

ccagcttgag gcctcggcat cttgagatgg aagagcagcc ttgtgtttag acctggattg   3360

aattgggccc tgttgtttcc tgggatcttg gggctggggg tgcccaacag cctggcatct   3420

tcttgtttct ctgtgtgttt actcattcat tcatttattc agctgataaa tattgactga   3480

tgccagctct gtgccaggca cattggacat gggggataca ctagtgggca gaaatagccc   3540

cgtcccagag ccggccatgg tggctcatac ctgttatacc agcactttgg gaggctgaag   3600

tgggaggatc gcttgagcct gggagttcaa gaccagcctg ggcaacatgg caagaccctg   3660

tctctactaa aaatac                                                   3676
```

<210> SEQ ID NO 30
<211> LENGTH: 1935
<212> TYPE: DNA
<213> ORGANISM: Homo sapiens

<400> SEQUENCE: 30

```
gtgggttctg cctaaagctg aattcccagc gctttggctt ctctgagttg gggttgtgta     60

taggggtctt cgaacagttc cggaaccagc cagcagcctt taattcttgg gcggaccacg    120

gccggttctg atatcttagg gtgaagagag ggaggtgtcg gccagccaag agagaaaatt    180

gcggatcttg ggctcaggaa gacgggagaa ggggttcggg gtcccggggt ggaagaacgg    240

tcgtcgtggt tgcgcttata gaagtaggag cagagggttc tcgtggcaac cttttactac    300

ctttgcctta acctttggcc actgttcttg gctaagatga gcagccacca taccaccttt    360

ccttttgacc ctgagcggcg agtccggagt acgctgaaga aggtctttgg gtttgactct    420

tttaagacgc ctttacagga gagtgcgacc atggctgtag taaaaggtaa caaggacgtc    480

tttgtgtgca tgcccacagg ggcaggaaaa tccctatgct atcagctccc tgctctgttg    540

gccaaaggca tcaccattgt agtctctcct ctcattgctt tgattcagga ccaagtggac    600

cacttgctaa ccctaaaggt acgagtaagt tccctgaact cgaagctctc tgcacaggaa    660

aggaaggagc tgcttgctga cctggagcga gaaaagcccc agaccaagat tctgtacatc    720

accccagaga tggcagcttc atcctccttc cagcccaccc tgaactccct ggtgtcccgc    780

cacctgctgt cttacttggt ggtggatgaa gctcattgtg tttcccaatg gggcatgac    840

tttcgtcctg actacttgcg tctgggtgcc ctgcgctccc gcctgggaca tgccccttgt    900

gtggctctga ccgccacagc caccccacag gtccaagagg acgtgtttgc tgccctgcac    960
```

```
ctgaagaaac cagttgccat cttcaagact ccctgcttcc gggccaacct cttctatgat   1020

gtgcaattca aggaactgat ttctgatccc tatgggaacc tgaaggactt ctgccttaag   1080

gctcttggac aggaggctga taaagggtta tctggctgcg gcattgtgta ctgcaggact   1140

agagaggctt gtgaacagct ggccatagag ctcagctgca ggggtgtgaa cgccaaggct   1200

taccatgcag ggctgaaggc ctctgaaaga acgctggtgc agaacgactg gatggaggag   1260

aaggtccctg taattgttgc aaccattagt tttgggatgg gagtggataa agccaatgtc   1320

aggtttgtcg cccattggaa tattgccaag tctatggctg ggtactacca ggagtctggc   1380

cgggctggca gggatgggaa gccttcctgg tgccgtctct attactccag gaatgaccgg   1440

gaccaagtca gcttcctgat caggaaggaa gtagcaaaac tccaggaaaa gagaggaaac   1500

aaagcatctg ataaagccac tatcatggcc tttgatgccc tggtgacctt ctgtgaagaa   1560

ctggggcgat ggggcagggg ccacggaaag agtctgaggg ctgcttggtg tagtcaggtt   1620

gtgtccaggc atgcggagct gtgagtgcct gcaggagaga cacccaggag gagtttttac   1680

attttggtct aaaaagctct tggattcatc tcatctcatg gaatgatcct gtcggatgac   1740

gctgacgtga ttgcttcaga cttagaggtg aataaattga ggtccagaga ggtcacagtc   1800

acgaagctca tggtagactg aggccactaa acacccgtct cctgattttc agtggcgtcc   1860

tcatttgcat acacctgggc catcttggtt tttgcaagaa aaaagcgagg aaatcagaga   1920

aaaaaaaaaa aaaaa                                                    1935


<210> SEQ ID NO 31
<211> LENGTH: 21
<212> TYPE: DNA
<213> ORGANISM: Artificial Sequence
<220> FEATURE:
<223> OTHER INFORMATION: an artificially synthesized DNA/RNA hybrid
      sequence

<400> SEQUENCE: 31

gccuaugaag caaggagaut t                                               21


<210> SEQ ID NO 32
<211> LENGTH: 21
<212> TYPE: DNA
<213> ORGANISM: Artificial Sequence
<220> FEATURE:
<223> OTHER INFORMATION: an artificially synthesized DNA/RNA hybrid
      sequence

<400> SEQUENCE: 32

guucacugcu guagucagut t                                               21


<210> SEQ ID NO 33
<211> LENGTH: 21
<212> TYPE: DNA
<213> ORGANISM: Artificial Sequence
<220> FEATURE:
<223> OTHER INFORMATION: an artificially synthesized DNA/RNA hybrid
      sequence

<400> SEQUENCE: 33

gauccugaag caggcagagt t                                               21


<210> SEQ ID NO 34
<211> LENGTH: 21
<212> TYPE: DNA
<213> ORGANISM: Artificial Sequence
<220> FEATURE:
```

<223> OTHER INFORMATION: an artificially synthesized DNA/RNA hybrid
sequence

<400> SEQUENCE: 34
gccagaugug agguuuguut t 21

<210> SEQ ID NO 35
<211> LENGTH: 21
<212> TYPE: DNA
<213> ORGANISM: Artificial Sequence
<220> FEATURE:
<223> OTHER INFORMATION: an artificially synthesized DNA/RNA hybrid
sequence

<400> SEQUENCE: 35
ggagaucagu ggaaacuuct t 21

<210> SEQ ID NO 36
<211> LENGTH: 21
<212> TYPE: DNA
<213> ORGANISM: Artificial Sequence
<220> FEATURE:
<223> OTHER INFORMATION: an artificially synthesized DNA/RNA hybrid
sequence

<400> SEQUENCE: 36
gaccaagugc uacagcuuat t 21

<210> SEQ ID NO 37
<211> LENGTH: 21
<212> TYPE: DNA
<213> ORGANISM: Artificial Sequence
<220> FEATURE:
<223> OTHER INFORMATION: an artificially synthesized DNA/RNA hybrid
sequence

<400> SEQUENCE: 37
gugaggaaga cacagaugct t 21

<210> SEQ ID NO 38
<211> LENGTH: 21
<212> TYPE: DNA
<213> ORGANISM: Artificial Sequence
<220> FEATURE:
<223> OTHER INFORMATION: an artificially synthesized DNA/RNA hybrid
sequence

<400> SEQUENCE: 38
ggaccagaua ugugacuuct t 21

<210> SEQ ID NO 39
<211> LENGTH: 21
<212> TYPE: DNA
<213> ORGANISM: Artificial Sequence
<220> FEATURE:
<223> OTHER INFORMATION: an artificially synthesized DNA/RNA hybrid
sequence

<400> SEQUENCE: 39
gccaauguca gguuugucgt t 21

<210> SEQ ID NO 40
<211> LENGTH: 21
<212> TYPE: DNA
<213> ORGANISM: Artificial Sequence
<220> FEATURE:
<223> OTHER INFORMATION: an artificially synthesized DNA/RNA hybrid
sequence

<400> SEQUENCE: 40
ggaaggagcu gcuugcugat t 21

<210> SEQ ID NO 41
<211> LENGTH: 21
<212> TYPE: DNA
<213> ORGANISM: Artificial Sequence
<220> FEATURE:
<223> OTHER INFORMATION: an artificially synthesized DNA/RNA hybrid
sequence

<400> SEQUENCE: 41
uucuccgaac gugucacgut t 21

<210> SEQ ID NO 42
<211> LENGTH: 21
<212> TYPE: DNA
<213> ORGANISM: Artificial Sequence
<220> FEATURE:
<223> OTHER INFORMATION: an artificially synthesized DNA/RNA hybrid
sequence

<400> SEQUENCE: 42
acgugacacg uucggagaat t 21

<210> SEQ ID NO 43
<211> LENGTH: 21
<212> TYPE: DNA
<213> ORGANISM: Artificial Sequence
<220> FEATURE:
<223> OTHER INFORMATION: an artificially synthesized DNA/RNA hybrid
sequence

<400> SEQUENCE: 43
gcuugaaacu auuaacguat t 21

<210> SEQ ID NO 44
<211> LENGTH: 21
<212> TYPE: DNA
<213> ORGANISM: Artificial Sequence
<220> FEATURE:
<223> OTHER INFORMATION: an artificially synthesized DNA/RNA hybrid
sequence

<400> SEQUENCE: 44
gaccacaguu cauagaaaat t 21

<210> SEQ ID NO 45
<211> LENGTH: 21
<212> TYPE: DNA
<213> ORGANISM: Artificial Sequence
<220> FEATURE:
<223> OTHER INFORMATION: an artificially synthesized DNA/RNA hybrid
sequence

<400> SEQUENCE: 45
ggcucaacau uuugaugaat t 21

<210> SEQ ID NO 46
<211> LENGTH: 21
<212> TYPE: DNA
<213> ORGANISM: Artificial Sequence
<220> FEATURE:
<223> OTHER INFORMATION: an artificially synthesized DNA/RNA hybrid
sequence

<400> SEQUENCE: 46
ggaacugaau gaaaaacuct t 21

<210> SEQ ID NO 47
<211> LENGTH: 21
<212> TYPE: DNA
<213> ORGANISM: Artificial Sequence
<220> FEATURE:
<223> OTHER INFORMATION: an artificially synthesized DNA/RNA hybrid sequence

<400> SEQUENCE: 47
gguucaugcu gaaaugguat t 21

<210> SEQ ID NO 48
<211> LENGTH: 21
<212> TYPE: DNA
<213> ORGANISM: Artificial Sequence
<220> FEATURE:
<223> OTHER INFORMATION: an artificially synthesized DNA/RNA hybrid sequence

<400> SEQUENCE: 48
gcuugaaacu auuaacguat t 21

<210> SEQ ID NO 49
<211> LENGTH: 21
<212> TYPE: DNA
<213> ORGANISM: Artificial Sequence
<220> FEATURE:
<223> OTHER INFORMATION: an artificially synthesized DNA/RNA hybrid sequence

<400> SEQUENCE: 49
gcaaggagau uuacucgaat t 21

<210> SEQ ID NO 50
<211> LENGTH: 21
<212> TYPE: DNA
<213> ORGANISM: Artificial Sequence
<220> FEATURE:
<223> OTHER INFORMATION: an artificially synthesized DNA/RNA hybrid sequence

<400> SEQUENCE: 50
gagcuuaugu uaccaguuat t 21

<210> SEQ ID NO 51
<211> LENGTH: 21
<212> TYPE: DNA
<213> ORGANISM: Artificial Sequence
<220> FEATURE:
<223> OTHER INFORMATION: an artificially synthesized DNA/RNA hybrid sequence

<400> SEQUENCE: 51
ccauggucug guaaaguuat t 21

<210> SEQ ID NO 52
<211> LENGTH: 21
<212> TYPE: DNA
<213> ORGANISM: Artificial Sequence
<220> FEATURE:
<223> OTHER INFORMATION: an artificially synthesized DNA/RNA hybrid sequence

<400> SEQUENCE: 52
agaacuuacg gaaaggcaat t 21

<210> SEQ ID NO 53
<211> LENGTH: 21
<212> TYPE: DNA
<213> ORGANISM: Artificial Sequence
<220> FEATURE:
<223> OTHER INFORMATION: an artificially synthesized DNA/RNA hybrid sequence

<400> SEQUENCE: 53
ccuucaagcu aaugaagaat t 21

<210> SEQ ID NO 54
<211> LENGTH: 21
<212> TYPE: DNA
<213> ORGANISM: Artificial Sequence
<220> FEATURE:
<223> OTHER INFORMATION: an artificially synthesized DNA/RNA hybrid sequence

<400> SEQUENCE: 54
agucuaacuu ggagaaguut t 21

<210> SEQ ID NO 55
<211> LENGTH: 21
<212> TYPE: DNA
<213> ORGANISM: Artificial Sequence
<220> FEATURE:
<223> OTHER INFORMATION: an artificially synthesized DNA/RNA hybrid sequence

<400> SEQUENCE: 55
ggaugaaugu gcagaauaat t 21

<210> SEQ ID NO 56
<211> LENGTH: 21
<212> TYPE: DNA
<213> ORGANISM: Artificial Sequence
<220> FEATURE:
<223> OTHER INFORMATION: an artificially synthesized DNA/RNA hybrid sequence

<400> SEQUENCE: 56
ggacaaaacg aaaaggggat t 21

<210> SEQ ID NO 57
<211> LENGTH: 21
<212> TYPE: DNA
<213> ORGANISM: Artificial Sequence
<220> FEATURE:
<223> OTHER INFORMATION: an artificially synthesized DNA/RNA hybrid sequence

<400> SEQUENCE: 57
aggcgaaaaa cagggaauat t 21

<210> SEQ ID NO 58
<211> LENGTH: 21
<212> TYPE: DNA
<213> ORGANISM: Artificial Sequence
<220> FEATURE:
<223> OTHER INFORMATION: an artificially synthesized DNA/RNA hybrid sequence

<400> SEQUENCE: 58
ggguuucuau cuuacuaaat t 21

-continued

<210> SEQ ID NO 59
<211> LENGTH: 21
<212> TYPE: DNA
<213> ORGANISM: Artificial Sequence
<220> FEATURE:
<223> OTHER INFORMATION: an artificially synthesized DNA/RNA hybrid sequence

<400> SEQUENCE: 59
gauuaguagu uacaugguat t 21

<210> SEQ ID NO 60
<211> LENGTH: 21
<212> TYPE: DNA
<213> ORGANISM: Artificial Sequence
<220> FEATURE:
<223> OTHER INFORMATION: an artificially synthesized DNA/RNA hybrid sequence

<400> SEQUENCE: 60
gccuguuauu ucggcacaat t 21

<210> SEQ ID NO 61
<211> LENGTH: 21
<212> TYPE: DNA
<213> ORGANISM: Artificial Sequence
<220> FEATURE:
<223> OTHER INFORMATION: an artificially synthesized DNA/RNA hybrid sequence

<400> SEQUENCE: 61
cucuguugga agucaucaat t 21

<210> SEQ ID NO 62
<211> LENGTH: 21
<212> TYPE: DNA
<213> ORGANISM: Artificial Sequence
<220> FEATURE:
<223> OTHER INFORMATION: an artificially synthesized DNA/RNA hybrid sequence

<400> SEQUENCE: 62
gaaguuucuc gguauaacat t 21

<210> SEQ ID NO 63
<211> LENGTH: 21
<212> TYPE: DNA
<213> ORGANISM: Artificial Sequence
<220> FEATURE:
<223> OTHER INFORMATION: an artificially synthesized DNA/RNA hybrid sequence

<400> SEQUENCE: 63
gaguaagcac ugcucagaat t 21

<210> SEQ ID NO 64
<211> LENGTH: 21
<212> TYPE: DNA
<213> ORGANISM: Artificial Sequence
<220> FEATURE:
<223> OTHER INFORMATION: an artificially synthesized DNA/RNA hybrid sequence

<400> SEQUENCE: 64
gaugcucagg aaagugacut t 21

<210> SEQ ID NO 65
<211> LENGTH: 21

<212> TYPE: DNA
<213> ORGANISM: Artificial Sequence
<220> FEATURE:
<223> OTHER INFORMATION: an artificially synthesized DNA/RNA hybrid
sequence

<400> SEQUENCE: 65
gagucaauuc agaauuauat t 21

<210> SEQ ID NO 66
<211> LENGTH: 21
<212> TYPE: DNA
<213> ORGANISM: Artificial Sequence
<220> FEATURE:
<223> OTHER INFORMATION: an artificially synthesized DNA/RNA hybrid
sequence

<400> SEQUENCE: 66
caaggaauga gaaauauaat t 21

<210> SEQ ID NO 67
<211> LENGTH: 21
<212> TYPE: DNA
<213> ORGANISM: Artificial Sequence
<220> FEATURE:
<223> OTHER INFORMATION: an artificially synthesized DNA/RNA hybrid
sequence

<400> SEQUENCE: 67
gaaucucaau guacauagat t 21

<210> SEQ ID NO 68
<211> LENGTH: 21
<212> TYPE: DNA
<213> ORGANISM: Artificial Sequence
<220> FEATURE:
<223> OTHER INFORMATION: an artificially synthesized DNA/RNA hybrid
sequence

<400> SEQUENCE: 68
cgcuagacag auaaguuuat t 21

<210> SEQ ID NO 69
<211> LENGTH: 21
<212> TYPE: DNA
<213> ORGANISM: Artificial Sequence
<220> FEATURE:
<223> OTHER INFORMATION: an artificially synthesized DNA/RNA hybrid
sequence

<400> SEQUENCE: 69
gguggcauuu gauugccuat t 21

<210> SEQ ID NO 70
<211> LENGTH: 649
<212> TYPE: PRT
<213> ORGANISM: Homo sapiens
<300> PUBLICATION INFORMATION:
<308> DATABASE ACCESSION NUMBER: GenBank/NM_002907
<309> DATABASE ENTRY DATE: 2006-11-17
<313> RELEVANT RESIDUES IN SEQ ID NO: (472)..(2421)

<400> SEQUENCE: 70

Met Ala Ser Val Ser Ala Leu Thr Glu Glu Leu Asp Ser Ile Thr Ser
1 5 10 15

Glu Leu His Ala Val Glu Ile Gln Ile Gln Glu Leu Thr Glu Arg Gln
20 25 30

-continued

```
Gln Glu Leu Ile Gln Lys Lys Lys Val Leu Thr Lys Lys Ile Lys Gln
        35                  40                  45

Cys Leu Glu Asp Ser Asp Ala Gly Ala Ser Asn Glu Tyr Asp Ser Ser
    50                  55                  60

Pro Ala Ala Trp Asn Lys Glu Asp Phe Pro Trp Ser Gly Lys Val Lys
65                  70                  75                  80

Asp Ile Leu Gln Asn Val Phe Lys Leu Glu Lys Phe Arg Pro Leu Gln
                85                  90                  95

Leu Glu Thr Ile Asn Val Thr Met Ala Gly Lys Glu Val Phe Leu Val
            100                 105                 110

Met Pro Thr Gly Gly Gly Lys Ser Leu Cys Tyr Gln Leu Pro Ala Leu
        115                 120                 125

Cys Ser Asp Gly Phe Thr Leu Val Ile Cys Pro Leu Ile Ser Leu Met
    130                 135                 140

Glu Asp Gln Leu Met Val Leu Lys Gln Leu Gly Ile Ser Ala Thr Met
145                 150                 155                 160

Leu Asn Ala Ser Ser Ser Lys Glu His Val Lys Trp Val His Ala Glu
                165                 170                 175

Met Val Asn Lys Asn Ser Glu Leu Lys Leu Ile Tyr Val Thr Pro Glu
            180                 185                 190

Lys Ile Ala Lys Ser Lys Met Phe Met Ser Arg Leu Glu Lys Ala Tyr
        195                 200                 205

Glu Ala Arg Arg Phe Thr Arg Ile Ala Val Asp Glu Val His Cys Cys
    210                 215                 220

Ser Gln Trp Gly His Asp Phe Arg Pro Asp Tyr Lys Ala Leu Gly Ile
225                 230                 235                 240

Leu Lys Arg Gln Phe Pro Asn Ala Ser Leu Ile Gly Leu Thr Ala Thr
                245                 250                 255

Ala Thr Asn His Val Leu Thr Asp Ala Gln Lys Ile Leu Cys Ile Glu
            260                 265                 270

Lys Cys Phe Thr Phe Thr Ala Ser Phe Asn Arg Pro Asn Leu Tyr Tyr
        275                 280                 285

Glu Val Arg Gln Lys Pro Ser Asn Thr Glu Asp Phe Ile Glu Asp Ile
    290                 295                 300

Val Lys Leu Ile Asn Gly Arg Tyr Lys Gly Gln Ser Gly Ile Ile Tyr
305                 310                 315                 320

Cys Phe Ser Gln Lys Asp Ser Glu Gln Val Thr Val Ser Leu Gln Asn
                325                 330                 335

Leu Gly Ile His Ala Gly Ala Tyr His Ala Asn Leu Glu Pro Glu Asp
            340                 345                 350

Lys Thr Thr Val His Arg Lys Trp Ser Ala Asn Glu Ile Gln Val Val
        355                 360                 365

Val Ala Thr Val Ala Phe Gly Met Gly Ile Asp Lys Pro Asp Val Arg
    370                 375                 380

Phe Val Ile His His Ser Met Ser Lys Ser Met Glu Asn Tyr Tyr Gln
385                 390                 395                 400

Glu Ser Gly Arg Ala Gly Arg Asp Asp Met Lys Ala Asp Cys Ile Leu
                405                 410                 415

Tyr Tyr Gly Phe Gly Asp Ile Phe Arg Ile Ser Ser Met Val Val Met
            420                 425                 430

Glu Asn Val Gly Gln Gln Lys Leu Tyr Glu Met Val Ser Tyr Cys Gln
        435                 440                 445

Asn Ile Ser Lys Cys Arg Arg Val Leu Met Ala Gln His Phe Asp Glu
    450                 455                 460
```

Val Trp Asn Ser Glu Ala Cys Asn Lys Met Cys Asp Asn Cys Cys Lys
465 470 475 480

Asp Ser Ala Phe Glu Arg Lys Asn Ile Thr Glu Tyr Cys Arg Asp Leu
485 490 495

Ile Lys Ile Leu Lys Gln Ala Glu Glu Leu Asn Glu Lys Leu Thr Pro
500 505 510

Leu Lys Leu Ile Asp Ser Trp Met Gly Lys Gly Ala Ala Lys Leu Arg
515 520 525

Val Ala Gly Val Val Ala Pro Thr Leu Pro Arg Glu Asp Leu Glu Lys
530 535 540

Ile Ile Ala His Phe Leu Ile Gln Gln Tyr Leu Lys Glu Asp Tyr Ser
545 550 555 560

Phe Thr Ala Tyr Ala Thr Ile Ser Tyr Leu Lys Ile Gly Pro Lys Ala
565 570 575

Asn Leu Leu Asn Asn Glu Ala His Ala Ile Thr Met Gln Val Thr Lys
580 585 590

Ser Thr Gln Asn Ser Phe Arg Ala Glu Ser Ser Gln Thr Cys His Ser
595 600 605

Glu Gln Gly Asp Lys Lys Met Glu Glu Lys Asn Ser Gly Asn Phe Gln
610 615 620

Lys Lys Ala Ala Asn Met Leu Gln Gln Ser Gly Ser Lys Asn Thr Gly
625 630 635 640

Ala Lys Lys Arg Lys Ile Asp Asp Ala
645

<210> SEQ ID NO 71
<211> LENGTH: 1432
<212> TYPE: PRT
<213> ORGANISM: Homo sapiens
<300> PUBLICATION INFORMATION:
<308> DATABASE ACCESSION NUMBER: GenBank/NM_000553
<309> DATABASE ENTRY DATE: 2006-12-03
<313> RELEVANT RESIDUES IN SEQ ID NO: (789)..(5087)

<400> SEQUENCE: 71

Met Ser Glu Lys Lys Leu Glu Thr Thr Ala Gln Gln Arg Lys Cys Pro
1 5 10 15

Glu Trp Met Asn Val Gln Asn Lys Arg Cys Ala Val Glu Glu Arg Lys
20 25 30

Ala Cys Val Arg Lys Ser Val Phe Glu Asp Asp Leu Pro Phe Leu Glu
35 40 45

Phe Thr Gly Ser Ile Val Tyr Ser Tyr Asp Ala Ser Asp Cys Ser Phe
50 55 60

Leu Ser Glu Asp Ile Ser Met Ser Leu Ser Asp Gly Asp Val Val Gly
65 70 75 80

Phe Asp Met Glu Trp Pro Pro Leu Tyr Asn Arg Gly Lys Leu Gly Lys
85 90 95

Val Ala Leu Ile Gln Leu Cys Val Ser Glu Ser Lys Cys Tyr Leu Phe
100 105 110

His Val Ser Ser Met Ser Val Phe Pro Gln Gly Leu Lys Met Leu Leu
115 120 125

Glu Asn Lys Ala Val Lys Lys Ala Gly Val Gly Ile Glu Gly Asp Gln
130 135 140

Trp Lys Leu Leu Arg Asp Phe Asp Ile Lys Leu Lys Asn Phe Val Glu
145 150 155 160

Leu Thr Asp Val Ala Asn Lys Lys Leu Lys Cys Thr Glu Thr Trp Ser

-continued

```
                165                 170                 175

Leu Asn Ser Leu Val Lys His Leu Leu Gly Lys Gln Leu Leu Lys Asp
            180                 185                 190

Lys Ser Ile Arg Cys Ser Asn Trp Ser Lys Phe Pro Leu Thr Glu Asp
        195                 200                 205

Gln Lys Leu Tyr Ala Ala Thr Asp Ala Tyr Ala Gly Phe Ile Ile Tyr
    210                 215                 220

Arg Asn Leu Glu Ile Leu Asp Asp Thr Val Gln Arg Phe Ala Ile Asn
225                 230                 235                 240

Lys Glu Glu Glu Ile Leu Leu Ser Asp Met Asn Lys Gln Leu Thr Ser
                245                 250                 255

Ile Ser Glu Glu Val Met Asp Leu Ala Lys His Leu Pro His Ala Phe
            260                 265                 270

Ser Lys Leu Glu Asn Pro Arg Arg Val Ser Ile Leu Leu Lys Asp Ile
        275                 280                 285

Ser Glu Asn Leu Tyr Ser Leu Arg Arg Met Ile Ile Gly Ser Thr Asn
    290                 295                 300

Ile Glu Thr Glu Leu Arg Pro Ser Asn Asn Leu Asn Leu Leu Ser Phe
305                 310                 315                 320

Glu Asp Ser Thr Thr Gly Gly Val Gln Gln Lys Gln Ile Arg Glu His
                325                 330                 335

Glu Val Leu Ile His Val Glu Asp Glu Thr Trp Asp Pro Thr Leu Asp
            340                 345                 350

His Leu Ala Lys His Asp Gly Glu Asp Val Leu Gly Asn Lys Val Glu
        355                 360                 365

Arg Lys Glu Asp Gly Phe Glu Asp Gly Val Glu Asp Asn Lys Leu Lys
    370                 375                 380

Glu Asn Met Glu Arg Ala Cys Leu Met Ser Leu Asp Ile Thr Glu His
385                 390                 395                 400

Glu Leu Gln Ile Leu Glu Gln Gln Ser Gln Glu Glu Tyr Leu Ser Asp
                405                 410                 415

Ile Ala Tyr Lys Ser Thr Glu His Leu Ser Pro Asn Asp Asn Glu Asn
            420                 425                 430

Asp Thr Ser Tyr Val Ile Glu Ser Asp Glu Asp Leu Glu Met Glu Met
        435                 440                 445

Leu Lys His Leu Ser Pro Asn Asp Asn Glu Asn Asp Thr Ser Tyr Val
    450                 455                 460

Ile Glu Ser Asp Glu Asp Leu Glu Met Glu Met Leu Lys Ser Leu Glu
465                 470                 475                 480

Asn Leu Asn Ser Gly Thr Val Glu Pro Thr His Ser Lys Cys Leu Lys
                485                 490                 495

Met Glu Arg Asn Leu Gly Leu Pro Thr Lys Glu Glu Glu Glu Asp Asp
            500                 505                 510

Glu Asn Glu Ala Asn Glu Gly Glu Glu Asp Asp Asp Lys Asp Phe Leu
        515                 520                 525

Trp Pro Ala Pro Asn Glu Glu Gln Val Thr Cys Leu Lys Met Tyr Phe
    530                 535                 540

Gly His Ser Ser Phe Lys Pro Val Gln Trp Lys Val Ile His Ser Val
545                 550                 555                 560

Leu Glu Glu Arg Arg Asp Asn Val Ala Val Met Ala Thr Gly Tyr Gly
                565                 570                 575

Lys Ser Leu Cys Phe Gln Tyr Pro Pro Val Tyr Val Gly Lys Ile Gly
            580                 585                 590
```

-continued

```
Leu Val Ile Ser Pro Leu Ile Ser Leu Met Glu Asp Gln Val Leu Gln
        595                 600                 605

Leu Lys Met Ser Asn Ile Pro Ala Cys Phe Leu Gly Ser Ala Gln Ser
    610                 615                 620

Glu Asn Val Leu Thr Asp Ile Lys Leu Gly Lys Tyr Arg Ile Val Tyr
625                 630                 635                 640

Val Thr Pro Glu Tyr Cys Ser Gly Asn Met Gly Leu Leu Gln Gln Leu
                645                 650                 655

Glu Ala Asp Ile Gly Ile Thr Leu Ile Ala Val Asp Glu Ala His Cys
            660                 665                 670

Ile Ser Glu Trp Gly His Asp Phe Arg Asp Ser Phe Arg Lys Leu Gly
        675                 680                 685

Ser Leu Lys Thr Ala Leu Pro Met Val Pro Ile Val Ala Leu Thr Ala
    690                 695                 700

Thr Ala Ser Ser Ser Ile Arg Glu Asp Ile Val Arg Cys Leu Asn Leu
705                 710                 715                 720

Arg Asn Pro Gln Ile Thr Cys Thr Gly Phe Asp Arg Pro Asn Leu Tyr
                725                 730                 735

Leu Glu Val Arg Arg Lys Thr Gly Asn Ile Leu Gln Asp Leu Gln Pro
            740                 745                 750

Phe Leu Val Lys Thr Ser Ser His Trp Glu Phe Glu Gly Pro Thr Ile
        755                 760                 765

Ile Tyr Cys Pro Ser Arg Lys Met Thr Gln Gln Val Thr Gly Glu Leu
    770                 775                 780

Arg Lys Leu Asn Leu Ser Cys Gly Thr Tyr His Ala Gly Met Ser Phe
785                 790                 795                 800

Ser Thr Arg Lys Asp Ile His His Arg Phe Val Arg Asp Glu Ile Gln
                805                 810                 815

Cys Val Ile Ala Thr Ile Ala Phe Gly Met Gly Ile Asn Lys Ala Asp
            820                 825                 830

Ile Arg Gln Val Ile His Tyr Gly Ala Pro Lys Asp Met Glu Ser Tyr
        835                 840                 845

Tyr Gln Glu Ile Gly Arg Ala Gly Arg Asp Gly Leu Gln Ser Ser Cys
    850                 855                 860

His Val Leu Trp Ala Pro Ala Asp Ile Asn Leu Asn Arg His Leu Leu
865                 870                 875                 880

Thr Glu Ile Arg Asn Glu Lys Phe Arg Leu Tyr Lys Leu Lys Met Met
                885                 890                 895

Ala Lys Met Glu Lys Tyr Leu His Ser Ser Arg Cys Arg Arg Gln Ile
            900                 905                 910

Ile Leu Ser His Phe Glu Asp Lys Gln Val Gln Lys Ala Ser Leu Gly
        915                 920                 925

Ile Met Gly Thr Glu Lys Cys Cys Asp Asn Cys Arg Ser Arg Leu Asp
    930                 935                 940

His Cys Tyr Ser Met Asp Asp Ser Glu Asp Thr Ser Trp Asp Phe Gly
945                 950                 955                 960

Pro Gln Ala Phe Lys Leu Leu Ser Ala Val Asp Ile Leu Gly Glu Lys
                965                 970                 975

Phe Gly Ile Gly Leu Pro Ile Leu Phe Leu Arg Gly Ser Asn Ser Gln
            980                 985                 990

Arg Leu Ala Asp Gln Tyr Arg Arg  His Ser Leu Phe Gly  Thr Gly Lys
        995                 1000                 1005

Asp Gln  Thr Glu Ser Trp Trp  Lys Ala Phe Ser Arg  Gln Leu Ile
    1010                 1015                 1020
```

-continued

```
Thr Glu  Gly Phe Leu Val Glu  Val Ser Arg Tyr Asn  Lys Phe Met
    1025                 1030                 1035

Lys Ile  Cys Ala Leu Thr Lys  Lys Gly Arg Asn Trp  Leu His Lys
    1040                 1045                 1050

Ala Asn  Thr Glu Ser Gln Ser  Leu Ile Leu Gln Ala  Asn Glu Glu
    1055                 1060                 1065

Leu Cys  Pro Lys Lys Phe Leu  Leu Pro Ser Ser Lys  Thr Val Ser
    1070                 1075                 1080

Ser Gly  Thr Lys Glu His Cys  Tyr Asn Gln Val Pro  Val Glu Leu
    1085                 1090                 1095

Ser Thr  Glu Lys Lys Ser Asn  Leu Glu Lys Leu Tyr  Ser Tyr Lys
    1100                 1105                 1110

Pro Cys  Asp Lys Ile Ser Ser  Gly Ser Asn Ile Ser  Lys Lys Ser
    1115                 1120                 1125

Ile Met  Val Gln Ser Pro Glu  Lys Ala Tyr Ser Ser  Ser Gln Pro
    1130                 1135                 1140

Val Ile  Ser Ala Gln Glu Gln  Glu Thr Gln Ile Val  Leu Tyr Gly
    1145                 1150                 1155

Lys Leu  Val Glu Ala Arg Gln  Lys His Ala Asn Lys  Met Asp Val
    1160                 1165                 1170

Pro Pro  Ala Ile Leu Ala Thr  Asn Lys Ile Leu Val  Asp Met Ala
    1175                 1180                 1185

Lys Met  Arg Pro Thr Thr Val  Glu Asn Val Lys Arg  Ile Asp Gly
    1190                 1195                 1200

Val Ser  Glu Gly Lys Ala Ala  Met Leu Ala Pro Leu  Leu Glu Val
    1205                 1210                 1215

Ile Lys  His Phe Cys Gln Thr  Asn Ser Val Gln Thr  Asp Leu Phe
    1220                 1225                 1230

Ser Ser  Thr Lys Pro Gln Glu  Glu Gln Lys Thr Ser  Leu Val Ala
    1235                 1240                 1245

Lys Asn  Lys Ile Cys Thr Leu  Ser Gln Ser Met Ala  Ile Thr Tyr
    1250                 1255                 1260

Ser Leu  Phe Gln Glu Lys Lys  Met Pro Leu Lys Ser  Ile Ala Glu
    1265                 1270                 1275

Ser Arg  Ile Leu Pro Leu Met  Thr Ile Gly Met His  Leu Ser Gln
    1280                 1285                 1290

Ala Val  Lys Ala Gly Cys Pro  Leu Asp Leu Glu Arg  Ala Gly Leu
    1295                 1300                 1305

Thr Pro  Glu Val Gln Lys Ile  Ile Ala Asp Val Ile  Arg Asn Pro
    1310                 1315                 1320

Pro Val  Asn Ser Asp Met Ser  Lys Ile Ser Leu Ile  Arg Met Leu
    1325                 1330                 1335

Val Pro  Glu Asn Ile Asp Thr  Tyr Leu Ile His Met  Ala Ile Glu
    1340                 1345                 1350

Ile Leu  Lys His Gly Pro Asp  Ser Gly Leu Gln Pro  Ser Cys Asp
    1355                 1360                 1365

Val Asn  Lys Arg Arg Cys Phe  Pro Gly Ser Glu Glu  Ile Cys Ser
    1370                 1375                 1380

Ser Ser  Lys Arg Ser Lys Glu  Glu Val Gly Ile Asn  Thr Glu Thr
    1385                 1390                 1395

Ser Ser  Ala Glu Arg Lys Arg  Arg Leu Pro Val Trp  Phe Ala Lys
    1400                 1405                 1410

Gly Ser  Asp Thr Ser Lys Lys  Leu Met Asp Lys Thr  Lys Arg Gly
```

1415 1420 1425

Gly Leu Phe Ser
1430

<210> SEQ ID NO 72
<211> LENGTH: 1417
<212> TYPE: PRT
<213> ORGANISM: Homo sapiens
<300> PUBLICATION INFORMATION:
<308> DATABASE ACCESSION NUMBER: GenBank/NM_000057
<309> DATABASE ENTRY DATE: 2006-11-18
<313> RELEVANT RESIDUES IN SEQ ID NO: (98)..(4351)

<400> SEQUENCE: 72

Met Ala Ala Val Pro Gln Asn Asn Leu Gln Glu Gln Leu Glu Arg His
1 5 10 15

Ser Ala Arg Thr Leu Asn Asn Lys Leu Ser Leu Ser Lys Pro Lys Phe
20 25 30

Ser Gly Phe Thr Phe Lys Lys Lys Thr Ser Ser Asp Asn Asn Val Ser
35 40 45

Val Thr Asn Val Ser Val Ala Lys Thr Pro Val Leu Arg Asn Lys Asp
50 55 60

Val Asn Val Thr Glu Asp Phe Ser Phe Ser Glu Pro Leu Pro Asn Thr
65 70 75 80

Thr Asn Gln Gln Arg Val Lys Asp Phe Phe Lys Asn Ala Pro Ala Gly
85 90 95

Gln Glu Thr Gln Arg Gly Gly Ser Lys Ser Leu Leu Pro Asp Phe Leu
100 105 110

Gln Thr Pro Lys Glu Val Val Cys Thr Thr Gln Asn Thr Pro Thr Val
115 120 125

Lys Lys Ser Arg Asp Thr Ala Leu Lys Lys Leu Glu Phe Ser Ser Ser
130 135 140

Pro Asp Ser Leu Ser Thr Ile Asn Asp Trp Asp Asp Met Asp Asp Phe
145 150 155 160

Asp Thr Ser Glu Thr Ser Lys Ser Phe Val Thr Pro Pro Gln Ser His
165 170 175

Phe Val Arg Val Ser Thr Ala Gln Lys Ser Lys Lys Gly Lys Arg Asn
180 185 190

Phe Phe Lys Ala Gln Leu Tyr Thr Thr Asn Thr Val Lys Thr Asp Leu
195 200 205

Pro Pro Pro Ser Ser Glu Ser Glu Gln Ile Asp Leu Thr Glu Glu Gln
210 215 220

Lys Asp Asp Ser Glu Trp Leu Ser Ser Asp Val Ile Cys Ile Asp Asp
225 230 235 240

Gly Pro Ile Ala Glu Val His Ile Asn Glu Asp Ala Gln Glu Ser Asp
245 250 255

Ser Leu Lys Thr His Leu Glu Asp Glu Arg Asp Asn Ser Glu Lys Lys
260 265 270

Lys Asn Leu Glu Glu Ala Glu Leu His Ser Thr Glu Lys Val Pro Cys
275 280 285

Ile Glu Phe Asp Asp Asp Asp Tyr Asp Thr Asp Phe Val Pro Pro Ser
290 295 300

Pro Glu Glu Ile Ile Ser Ala Ser Ser Ser Ser Ser Lys Cys Leu Ser
305 310 315 320

Thr Leu Lys Asp Leu Asp Thr Ser Asp Arg Lys Glu Asp Val Leu Ser
325 330 335

-continued

```
Thr Ser Lys Asp Leu Leu Ser Lys Pro Glu Lys Met Ser Met Gln Glu
            340                 345                 350

Leu Asn Pro Glu Thr Ser Thr Asp Cys Asp Ala Arg Gln Ile Ser Leu
        355                 360                 365

Gln Gln Gln Leu Ile His Val Met Glu His Ile Cys Lys Leu Ile Asp
    370                 375                 380

Thr Ile Pro Asp Asp Lys Leu Lys Leu Leu Asp Cys Gly Asn Glu Leu
385                 390                 395                 400

Leu Gln Gln Arg Asn Ile Arg Arg Lys Leu Leu Thr Glu Val Asp Phe
                405                 410                 415

Asn Lys Ser Asp Ala Ser Leu Leu Gly Ser Leu Trp Arg Tyr Arg Pro
            420                 425                 430

Asp Ser Leu Asp Gly Pro Met Glu Gly Asp Ser Cys Pro Thr Gly Asn
        435                 440                 445

Ser Met Lys Glu Leu Asn Phe Ser His Leu Pro Ser Asn Ser Val Ser
    450                 455                 460

Pro Gly Asp Cys Leu Leu Thr Thr Thr Leu Gly Lys Thr Gly Phe Ser
465                 470                 475                 480

Ala Thr Arg Lys Asn Leu Phe Glu Arg Pro Leu Phe Asn Thr His Leu
                485                 490                 495

Gln Lys Ser Phe Val Ser Ser Asn Trp Ala Glu Thr Pro Arg Leu Gly
            500                 505                 510

Lys Lys Asn Glu Ser Ser Tyr Phe Pro Gly Asn Val Leu Thr Ser Thr
        515                 520                 525

Ala Val Lys Asp Gln Asn Lys His Thr Ala Ser Ile Asn Asp Leu Glu
    530                 535                 540

Arg Glu Thr Gln Pro Ser Tyr Asp Ile Asp Asn Phe Asp Ile Asp Asp
545                 550                 555                 560

Phe Asp Asp Asp Asp Asp Trp Glu Asp Ile Met His Asn Leu Ala Ala
                565                 570                 575

Ser Lys Ser Ser Thr Ala Ala Tyr Gln Pro Ile Lys Glu Gly Arg Pro
            580                 585                 590

Ile Lys Ser Val Ser Glu Arg Leu Ser Ser Ala Lys Thr Asp Cys Leu
        595                 600                 605

Pro Val Ser Ser Thr Ala Gln Asn Ile Asn Phe Ser Glu Ser Ile Gln
    610                 615                 620

Asn Tyr Thr Asp Lys Ser Ala Gln Asn Leu Ala Ser Arg Asn Leu Lys
625                 630                 635                 640

His Glu Arg Phe Gln Ser Leu Ser Phe Pro His Thr Lys Glu Met Met
                645                 650                 655

Lys Ile Phe His Lys Lys Phe Gly Leu His Asn Phe Arg Thr Asn Gln
            660                 665                 670

Leu Glu Ala Ile Asn Ala Ala Leu Leu Gly Glu Asp Cys Phe Ile Leu
        675                 680                 685

Met Pro Thr Gly Gly Gly Lys Ser Leu Cys Tyr Gln Leu Pro Ala Cys
    690                 695                 700

Val Ser Pro Gly Val Thr Val Val Ile Ser Pro Leu Arg Ser Leu Ile
705                 710                 715                 720

Val Asp Gln Val Gln Lys Leu Thr Ser Leu Asp Ile Pro Ala Thr Tyr
                725                 730                 735

Leu Thr Gly Asp Lys Thr Asp Ser Glu Ala Thr Asn Ile Tyr Leu Gln
            740                 745                 750

Leu Ser Lys Lys Asp Pro Ile Ile Lys Leu Leu Tyr Val Thr Pro Glu
        755                 760                 765
```

-continued

```
Lys Ile Cys Ala Ser Asn Arg Leu Ile Ser Thr Leu Glu Asn Leu Tyr
    770                 775                 780

Glu Arg Lys Leu Leu Ala Arg Phe Val Ile Asp Glu Ala His Cys Val
785                 790                 795                 800

Ser Gln Trp Gly His Asp Phe Arg Gln Asp Tyr Lys Arg Met Asn Met
                805                 810                 815

Leu Arg Gln Lys Phe Pro Ser Val Pro Val Met Ala Leu Thr Ala Thr
            820                 825                 830

Ala Asn Pro Arg Val Gln Lys Asp Ile Leu Thr Gln Leu Lys Ile Leu
        835                 840                 845

Arg Pro Gln Val Phe Ser Met Ser Phe Asn Arg His Asn Leu Lys Tyr
    850                 855                 860

Tyr Val Leu Pro Lys Lys Pro Lys Lys Val Ala Phe Asp Cys Leu Glu
865                 870                 875                 880

Trp Ile Arg Lys His His Pro Tyr Asp Ser Gly Ile Ile Tyr Cys Leu
                885                 890                 895

Ser Arg Arg Glu Cys Asp Thr Met Ala Asp Thr Leu Gln Arg Asp Gly
            900                 905                 910

Leu Ala Ala Leu Ala Tyr His Ala Gly Leu Ser Asp Ser Ala Arg Asp
        915                 920                 925

Glu Val Gln Gln Lys Trp Ile Asn Gln Asp Gly Cys Gln Val Ile Cys
    930                 935                 940

Ala Thr Ile Ala Phe Gly Met Gly Ile Asp Lys Pro Asp Val Arg Phe
945                 950                 955                 960

Val Ile His Ala Ser Leu Pro Lys Ser Val Glu Gly Tyr Tyr Gln Glu
                965                 970                 975

Ser Gly Arg Ala Gly Arg Asp Gly Glu Ile Ser His Cys Leu Leu Phe
            980                 985                 990

Tyr Thr Tyr His Asp Val Thr Arg  Leu Lys Arg Leu Ile  Met Met Glu
        995                 1000                1005

Lys Asp  Gly Asn His His Thr  Arg Glu Thr His Phe  Asn Asn Leu
    1010                1015                1020

Tyr Ser  Met Val His Tyr Cys  Glu Asn Ile Thr Glu  Cys Arg Arg
    1025                1030                1035

Ile Gln  Leu Leu Ala Tyr Phe  Gly Glu Asn Gly Phe  Asn Pro Asp
    1040                1045                1050

Phe Cys  Lys Lys His Pro Asp  Val Ser Cys Asp Asn  Cys Cys Lys
    1055                1060                1065

Thr Lys  Asp Tyr Lys Thr Arg  Asp Val Thr Asp Asp  Val Lys Ser
    1070                1075                1080

Ile Val  Arg Phe Val Gln Glu  His Ser Ser Ser Gln  Gly Met Arg
    1085                1090                1095

Asn Ile  Lys His Val Gly Pro  Ser Gly Arg Phe Thr  Met Asn Met
    1100                1105                1110

Leu Val  Asp Ile Phe Leu Gly  Ser Lys Ser Ala Lys  Ile Gln Ser
    1115                1120                1125

Gly Ile  Phe Gly Lys Gly Ser  Ala Tyr Ser Arg His  Asn Ala Glu
    1130                1135                1140

Arg Leu  Phe Lys Lys Leu Ile  Leu Asp Lys Ile Leu  Asp Glu Asp
    1145                1150                1155

Leu Tyr  Ile Asn Ala Asn Asp  Gln Ala Ile Ala Tyr  Val Met Leu
    1160                1165                1170

Gly Asn  Lys Ala Gln Thr Val  Leu Asn Gly Asn Leu  Lys Val Asp
```

```
    1175                1180                1185

Phe Met  Glu Thr Glu Asn Ser  Ser Ser Val Lys Lys  Gln Lys Ala
    1190                1195                1200

Leu Val  Ala Lys Val Ser Gln  Arg Glu Glu Met Val  Lys Lys Cys
    1205                1210                1215

Leu Gly  Glu Leu Thr Glu Val  Cys Lys Ser Leu Gly  Lys Val Phe
    1220                1225                1230

Gly Val  His Tyr Phe Asn Ile  Phe Asn Thr Val Thr  Leu Lys Lys
    1235                1240                1245

Leu Ala  Glu Ser Leu Ser Ser  Asp Pro Glu Val Leu  Leu Gln Ile
    1250                1255                1260

Asp Gly  Val Thr Glu Asp Lys  Leu Glu Lys Tyr Gly  Ala Glu Val
    1265                1270                1275

Ile Ser  Val Leu Gln Lys Tyr  Ser Glu Trp Thr Ser  Pro Ala Glu
    1280                1285                1290

Asp Ser  Ser Pro Gly Ile Ser  Leu Ser Ser Ser Arg  Gly Pro Gly
    1295                1300                1305

Arg Ser  Ala Ala Glu Glu Leu  Asp Glu Glu Ile Pro  Val Ser Ser
    1310                1315                1320

His Tyr  Phe Ala Ser Lys Thr  Arg Asn Glu Arg Lys  Arg Lys Lys
    1325                1330                1335

Met Pro  Ala Ser Gln Arg Ser  Lys Arg Arg Lys Thr  Ala Ser Ser
    1340                1345                1350

Gly Ser  Lys Ala Lys Gly Gly  Ser Ala Thr Cys Arg  Lys Ile Ser
    1355                1360                1365

Ser Lys  Thr Lys Ser Ser Ser  Ile Ile Gly Ser Ser  Ser Ala Ser
    1370                1375                1380

His Thr  Ser Gln Ala Thr Ser  Gly Ala Asn Ser Lys  Leu Gly Ile
    1385                1390                1395

Met Ala  Pro Pro Lys Pro Ile  Asn Arg Pro Phe Leu  Lys Pro Ser
    1400                1405                1410

Tyr Ala  Phe Ser
    1415


<210> SEQ ID NO 73
<211> LENGTH: 1208
<212> TYPE: PRT
<213> ORGANISM: Homo sapiens
<300> PUBLICATION INFORMATION:
<308> DATABASE ACCESSION NUMBER: GenBank/NM_004260
<309> DATABASE ENTRY DATE: 2006-11-18
<313> RELEVANT RESIDUES IN SEQ ID NO: (33)..(3659)

<400> SEQUENCE: 73

Met Glu Arg Leu Arg Asp Val Arg Glu Arg Leu Gln Ala Trp Glu Arg
1               5                   10                  15

Ala Phe Arg Arg Gln Arg Gly Arg Arg Pro Ser Gln Asp Asp Val Glu
            20                  25                  30

Ala Ala Pro Glu Glu Thr Arg Ala Leu Tyr Arg Glu Tyr Arg Thr Leu
        35                  40                  45

Lys Arg Thr Thr Gly Gln Ala Gly Gly Gly Leu Arg Ser Ser Glu Ser
    50                  55                  60

Leu Pro Ala Ala Ala Glu Glu Ala Pro Glu Pro Arg Cys Trp Gly Pro
65                  70                  75                  80

His Leu Asn Arg Ala Ala Thr Lys Ser Pro Gln Pro Thr Pro Gly Arg
                85                  90                  95
```

-continued

```
Ser Arg Gln Gly Ser Val Pro Asp Tyr Gly Gln Arg Leu Lys Ala Asn
            100                 105                 110

Leu Lys Gly Thr Leu Gln Ala Gly Pro Ala Leu Gly Arg Arg Pro Trp
        115                 120                 125

Pro Leu Gly Arg Ala Ser Ser Lys Ala Ser Thr Pro Lys Pro Pro Gly
    130                 135                 140

Thr Gly Pro Val Pro Ser Phe Ala Glu Lys Val Ser Asp Glu Pro Pro
145                 150                 155                 160

Gln Leu Pro Glu Pro Gln Pro Arg Pro Gly Arg Leu Gln His Leu Gln
                165                 170                 175

Ala Ser Leu Ser Gln Arg Leu Gly Ser Leu Asp Pro Gly Trp Leu Gln
            180                 185                 190

Arg Cys His Ser Glu Val Pro Asp Phe Leu Gly Ala Pro Lys Ala Cys
        195                 200                 205

Arg Pro Asp Leu Gly Ser Glu Glu Ser Gln Leu Leu Ile Pro Gly Glu
    210                 215                 220

Ser Ala Val Leu Gly Pro Gly Ala Gly Ser Gln Gly Pro Glu Ala Ser
225                 230                 235                 240

Ala Phe Gln Glu Val Ser Ile Arg Val Gly Ser Pro Gln Pro Ser Ser
                245                 250                 255

Ser Gly Gly Glu Lys Arg Arg Trp Asn Glu Glu Pro Trp Glu Ser Pro
            260                 265                 270

Ala Gln Val Gln Gln Glu Ser Ser Gln Ala Gly Pro Pro Ser Glu Gly
        275                 280                 285

Ala Gly Ala Val Ala Val Glu Glu Asp Pro Pro Gly Glu Pro Val Gln
    290                 295                 300

Ala Gln Pro Pro Gln Pro Cys Ser Ser Pro Ser Asn Pro Arg Tyr His
305                 310                 315                 320

Gly Leu Ser Pro Ser Ser Gln Ala Arg Ala Gly Lys Ala Glu Gly Thr
                325                 330                 335

Ala Pro Leu His Ile Phe Pro Arg Leu Ala Arg His Asp Arg Gly Asn
            340                 345                 350

Tyr Val Arg Leu Asn Met Lys Gln Lys His Tyr Val Arg Gly Arg Ala
        355                 360                 365

Leu Arg Ser Arg Leu Leu Arg Lys Gln Ala Trp Lys Gln Lys Trp Arg
    370                 375                 380

Lys Lys Gly Glu Cys Phe Gly Gly Gly Gly Ala Thr Val Thr Thr Lys
385                 390                 395                 400

Glu Ser Cys Phe Leu Asn Glu Gln Phe Asp His Trp Ala Ala Gln Cys
                405                 410                 415

Pro Arg Pro Ala Ser Glu Glu Asp Thr Asp Ala Val Gly Pro Glu Pro
            420                 425                 430

Leu Val Pro Ser Pro Gln Pro Val Pro Glu Val Pro Ser Leu Asp Pro
        435                 440                 445

Thr Val Leu Pro Leu Tyr Ser Leu Gly Pro Ser Gly Gln Leu Ala Glu
    450                 455                 460

Thr Pro Ala Glu Val Phe Gln Ala Leu Glu Gln Leu Gly His Gln Ala
465                 470                 475                 480

Phe Arg Pro Gly Gln Glu Arg Ala Val Met Arg Ile Leu Ser Gly Ile
                485                 490                 495

Ser Thr Leu Leu Val Leu Pro Thr Gly Ala Gly Lys Ser Leu Cys Tyr
            500                 505                 510

Gln Leu Pro Ala Leu Leu Tyr Ser Arg Arg Ser Pro Cys Leu Thr Leu
        515                 520                 525
```

-continued

```
Val Val Ser Pro Leu Leu Ser Leu Met Asp Asp Gln Val Ser Gly Leu
    530                 535                 540

Pro Pro Cys Leu Lys Ala Ala Cys Ile His Ser Gly Met Thr Arg Lys
545                 550                 555                 560

Gln Arg Glu Ser Val Leu Gln Lys Ile Arg Ala Ala Gln Val His Val
                565                 570                 575

Leu Met Leu Thr Pro Glu Ala Leu Val Gly Ala Gly Gly Leu Pro Pro
            580                 585                 590

Ala Ala Gln Leu Pro Pro Val Ala Phe Ala Cys Ile Asp Glu Ala His
        595                 600                 605

Cys Leu Ser Gln Trp Ser His Asn Phe Arg Pro Cys Tyr Leu Arg Val
    610                 615                 620

Cys Lys Val Leu Arg Glu Arg Met Gly Val His Cys Phe Leu Gly Leu
625                 630                 635                 640

Thr Ala Thr Ala Thr Arg Arg Thr Ala Ser Asp Val Ala Gln His Leu
                645                 650                 655

Ala Val Ala Glu Glu Pro Asp Leu His Gly Pro Ala Pro Val Pro Thr
            660                 665                 670

Asn Leu His Leu Ser Val Ser Met Asp Arg Asp Thr Asp Gln Ala Leu
        675                 680                 685

Leu Thr Leu Leu Gln Gly Lys Arg Phe Gln Asn Leu Asp Ser Ile Ile
    690                 695                 700

Ile Tyr Cys Asn Arg Arg Glu Asp Thr Glu Arg Ile Ala Ala Leu Leu
705                 710                 715                 720

Arg Thr Cys Leu His Ala Ala Trp Val Pro Gly Ser Gly Gly Arg Ala
                725                 730                 735

Pro Lys Thr Thr Ala Glu Ala Tyr His Ala Gly Met Cys Ser Arg Glu
            740                 745                 750

Arg Arg Arg Val Gln Arg Ala Phe Met Gln Gly Gln Leu Arg Val Val
        755                 760                 765

Val Ala Thr Val Ala Phe Gly Met Gly Leu Asp Arg Pro Asp Val Arg
    770                 775                 780

Ala Val Leu His Leu Gly Leu Pro Pro Ser Phe Glu Ser Tyr Val Gln
785                 790                 795                 800

Ala Val Gly Arg Ala Gly Arg Asp Gly Gln Pro Ala His Cys His Leu
                805                 810                 815

Phe Leu Gln Pro Gln Gly Glu Asp Leu Arg Glu Leu Arg Arg His Val
            820                 825                 830

His Ala Asp Ser Thr Asp Phe Leu Ala Val Lys Arg Leu Val Gln Arg
        835                 840                 845

Val Phe Pro Ala Cys Thr Cys Thr Cys Thr Arg Pro Pro Ser Glu Gln
    850                 855                 860

Glu Gly Ala Val Gly Gly Glu Arg Pro Val Pro Lys Tyr Pro Pro Gln
865                 870                 875                 880

Glu Ala Glu Gln Leu Ser His Gln Ala Ala Pro Gly Pro Arg Arg Val
                885                 890                 895

Cys Met Gly His Glu Arg Ala Leu Pro Ile Gln Leu Thr Val Gln Ala
            900                 905                 910

Leu Asp Met Pro Glu Glu Ala Ile Glu Thr Leu Leu Cys Tyr Leu Glu
        915                 920                 925

Leu His Pro His His Trp Leu Glu Leu Leu Ala Thr Thr Tyr Thr His
    930                 935                 940

Cys Arg Leu Asn Cys Pro Gly Gly Pro Ala Gln Leu Gln Ala Leu Ala
```

-continued 945 950 955 960

His Arg Cys Pro Pro Leu Ala Val Cys Leu Ala Gln Gln Leu Pro Glu
965 970 975

Asp Pro Gly Gln Gly Ser Ser Ser Val Glu Phe Asp Met Val Lys Leu
980 985 990

Val Asp Ser Met Gly Trp Glu Leu Ala Ser Val Arg Arg Ala Leu Cys
995 1000 1005

Gln Leu Gln Trp Asp His Glu Pro Arg Thr Gly Val Arg Arg Gly
1010 1015 1020

Thr Gly Val Leu Val Glu Phe Ser Glu Leu Ala Phe His Leu Arg
1025 1030 1035

Ser Pro Gly Asp Leu Thr Ala Glu Glu Lys Asp Gln Ile Cys Asp
1040 1045 1050

Phe Leu Tyr Gly Arg Val Gln Ala Arg Glu Arg Gln Ala Leu Ala
1055 1060 1065

Arg Leu Arg Arg Thr Phe Gln Ala Phe His Ser Val Ala Phe Pro
1070 1075 1080

Ser Cys Gly Pro Cys Leu Glu Gln Gln Asp Glu Glu Arg Ser Thr
1085 1090 1095

Arg Leu Lys Asp Leu Leu Gly Arg Tyr Phe Glu Glu Glu Glu Gly
1100 1105 1110

Gln Glu Pro Gly Gly Met Glu Asp Ala Gln Gly Pro Glu Pro Gly
1115 1120 1125

Gln Ala Arg Leu Gln Asp Trp Glu Asp Gln Val Arg Cys Asp Ile
1130 1135 1140

Arg Gln Phe Leu Ser Leu Arg Pro Glu Glu Lys Phe Ser Ser Arg
1145 1150 1155

Ala Val Ala Arg Ile Phe His Gly Ile Gly Ser Pro Cys Tyr Pro
1160 1165 1170

Ala Gln Val Tyr Gly Gln Asp Arg Arg Phe Trp Arg Lys Tyr Leu
1175 1180 1185

His Leu Ser Phe His Ala Leu Val Gly Leu Ala Thr Glu Glu Leu
1190 1195 1200

Leu Gln Val Ala Arg
1205

<210> SEQ ID NO 74
<211> LENGTH: 991
<212> TYPE: PRT
<213> ORGANISM: Homo sapiens
<300> PUBLICATION INFORMATION:
<308> DATABASE ACCESSION NUMBER: GenBank/NM_004259
<309> DATABASE ENTRY DATE: 2006-11-18
<313> RELEVANT RESIDUES IN SEQ ID NO: (161)..(3055)

<400> SEQUENCE: 74

Met Ser Ser His His Thr Thr Phe Pro Phe Asp Pro Glu Arg Arg Val
1 5 10 15

Arg Ser Thr Leu Lys Lys Val Phe Gly Phe Asp Ser Phe Lys Thr Pro
20 25 30

Leu Gln Glu Ser Ala Thr Met Ala Val Val Lys Gly Asn Lys Asp Val
35 40 45

Phe Val Cys Met Pro Thr Gly Ala Gly Lys Ser Leu Cys Tyr Gln Leu
50 55 60

Pro Ala Leu Leu Ala Lys Gly Ile Thr Ile Val Val Ser Pro Leu Ile
65 70 75 80

-continued

```
Ala Leu Ile Gln Asp Gln Val Asp His Leu Leu Thr Leu Lys Val Arg
                85                  90                  95

Val Ser Ser Leu Asn Ser Lys Leu Ser Ala Gln Glu Arg Lys Glu Leu
            100                 105                 110

Leu Ala Asp Leu Glu Arg Glu Lys Pro Gln Thr Lys Ile Leu Tyr Ile
        115                 120                 125

Thr Pro Glu Met Ala Ala Ser Ser Ser Phe Gln Pro Thr Leu Asn Ser
    130                 135                 140

Leu Val Ser Arg His Leu Leu Ser Tyr Leu Val Val Asp Glu Ala His
145                 150                 155                 160

Cys Val Ser Gln Trp Gly His Asp Phe Arg Pro Asp Tyr Leu Arg Leu
                165                 170                 175

Gly Ala Leu Arg Ser Arg Leu Gly His Ala Pro Cys Val Ala Leu Thr
            180                 185                 190

Ala Thr Ala Thr Pro Gln Val Gln Glu Asp Val Phe Ala Ala Leu His
        195                 200                 205

Leu Lys Lys Pro Val Ala Ile Phe Lys Thr Pro Cys Phe Arg Ala Asn
    210                 215                 220

Leu Phe Tyr Asp Val Gln Phe Lys Glu Leu Ile Ser Asp Pro Tyr Gly
225                 230                 235                 240

Asn Leu Lys Asp Phe Cys Leu Lys Ala Leu Gly Gln Glu Ala Asp Lys
                245                 250                 255

Gly Leu Ser Gly Cys Gly Ile Val Tyr Cys Arg Thr Arg Glu Ala Cys
            260                 265                 270

Glu Gln Leu Ala Ile Glu Leu Ser Cys Arg Gly Val Asn Ala Lys Ala
        275                 280                 285

Tyr His Ala Gly Leu Lys Ala Ser Glu Arg Thr Leu Val Gln Asn Asp
    290                 295                 300

Trp Met Glu Glu Lys Val Pro Val Ile Val Ala Thr Ile Ser Phe Gly
305                 310                 315                 320

Met Gly Val Asp Lys Ala Asn Val Arg Phe Val Ala His Trp Asn Ile
                325                 330                 335

Ala Lys Ser Met Ala Gly Tyr Tyr Gln Glu Ser Gly Arg Ala Gly Arg
            340                 345                 350

Asp Gly Lys Pro Ser Trp Cys Arg Leu Tyr Tyr Ser Arg Asn Asp Arg
        355                 360                 365

Asp Gln Val Ser Phe Leu Ile Arg Lys Glu Val Ala Lys Leu Gln Glu
    370                 375                 380

Lys Arg Gly Asn Lys Ala Ser Asp Lys Ala Thr Ile Met Ala Phe Asp
385                 390                 395                 400

Ala Leu Val Thr Phe Cys Glu Glu Leu Gly Cys Arg His Ala Ala Ile
                405                 410                 415

Ala Lys Tyr Phe Gly Asp Ala Leu Pro Ala Cys Ala Lys Gly Cys Asp
            420                 425                 430

His Cys Gln Asn Pro Thr Ala Val Arg Arg Arg Leu Glu Ala Leu Glu
        435                 440                 445

Arg Ser Ser Ser Trp Ser Lys Thr Cys Ile Gly Pro Ser Gln Gly Asn
    450                 455                 460

Gly Phe Asp Pro Glu Leu Tyr Glu Gly Gly Arg Lys Gly Tyr Gly Asp
465                 470                 475                 480

Phe Ser Arg Tyr Asp Glu Gly Ser Gly Gly Ser Gly Asp Glu Gly Arg
                485                 490                 495

Asp Glu Ala His Lys Arg Glu Trp Asn Leu Phe Tyr Gln Lys Gln Met
            500                 505                 510
```

-continued

```
Gln Leu Arg Lys Gly Lys Asp Pro Lys Ile Glu Glu Phe Val Pro Pro
        515                 520                 525

Asp Glu Asn Cys Pro Leu Lys Glu Ala Ser Ser Arg Arg Ile Pro Arg
    530                 535                 540

Leu Thr Val Lys Ala Arg Glu His Cys Leu Arg Leu Leu Glu Glu Ala
545                 550                 555                 560

Leu Ser Ser Asn Arg Gln Ser Thr Arg Thr Ala Asp Glu Ala Asp Leu
                565                 570                 575

Arg Ala Lys Ala Val Glu Leu Glu His Glu Thr Phe Arg Asn Ala Lys
            580                 585                 590

Val Ala Asn Leu Tyr Lys Ala Ser Val Leu Lys Lys Val Ala Asp Ile
        595                 600                 605

His Arg Ala Ser Lys Asp Gly Gln Pro Tyr Asp Met Gly Gly Ser Ala
    610                 615                 620

Lys Ser Cys Ser Ala Gln Ala Glu Pro Pro Glu Pro Asn Glu Tyr Asp
625                 630                 635                 640

Ile Pro Pro Ala Ser His Val Tyr Ser Leu Lys Pro Lys Arg Val Gly
                645                 650                 655

Ala Gly Phe Pro Lys Gly Ser Cys Pro Phe Gln Thr Ala Thr Glu Leu
            660                 665                 670

Met Glu Thr Thr Arg Ile Arg Glu Gln Ala Pro Gln Pro Glu Arg Gly
        675                 680                 685

Gly Glu His Glu Pro Pro Ser Arg Pro Cys Gly Leu Leu Asp Glu Asp
    690                 695                 700

Gly Ser Glu Pro Leu Pro Gly Pro Arg Gly Glu Val Pro Gly Gly Ser
705                 710                 715                 720

Ala His Tyr Gly Gly Pro Ser Pro Glu Lys Lys Ala Lys Ser Ser Ser
                725                 730                 735

Gly Gly Ser Ser Leu Ala Lys Gly Arg Ala Ser Lys Lys Gln Gln Leu
            740                 745                 750

Leu Ala Thr Ala Ala His Lys Asp Ser Gln Ser Ile Ala Arg Phe Phe
        755                 760                 765

Cys Arg Arg Val Glu Ser Pro Ala Leu Leu Ala Ser Ala Pro Glu Ala
    770                 775                 780

Glu Gly Ala Cys Pro Ser Cys Glu Gly Val Gln Gly Pro Pro Met Ala
785                 790                 795                 800

Pro Glu Lys Tyr Thr Gly Glu Glu Asp Gly Ala Gly Gly His Ser Pro
                805                 810                 815

Ala Pro Pro Gln Thr Glu Glu Cys Leu Arg Glu Arg Pro Ser Thr Cys
            820                 825                 830

Pro Pro Arg Asp Gln Gly Thr Pro Glu Val Gln Pro Thr Pro Ala Lys
        835                 840                 845

Asp Thr Trp Lys Gly Lys Arg Pro Arg Ser Gln Gln Glu Asn Pro Glu
    850                 855                 860

Ser Gln Pro Gln Lys Arg Pro Arg Pro Ser Ala Lys Pro Ser Val Val
865                 870                 875                 880

Ala Glu Val Lys Gly Ser Val Ser Ala Ser Glu Gln Gly Thr Leu Asn
                885                 890                 895

Pro Thr Ala Gln Asp Pro Phe Gln Leu Ser Ala Pro Gly Val Ser Leu
            900                 905                 910

Lys Glu Ala Ala Asn Val Val Val Lys Cys Leu Thr Pro Phe Tyr Lys
        915                 920                 925

Glu Gly Lys Phe Ala Ser Lys Glu Leu Phe Lys Gly Phe Ala Arg His
```

-continued

| | | | | | | | | | | | | | | | |
|---|---|---|---|---|---|---|---|---|---|---|---|---|---|---|---|
| | 930 | | | | 935 | | | | 940 | | | | | | |
| Leu | Ser | His | Leu | Leu | Thr | Gln | Lys | Thr | Ser | Pro | Gly | Arg | Ser | Val | Lys |
| 945 | | | | | 950 | | | | | 955 | | | | | 960 |
| Glu | Glu | Ala | Gln | Asn | Leu | Ile | Arg | His | Phe | Phe | His | Gly | Arg | Ala | Arg |
| | | | | 965 | | | | | 970 | | | | | 975 | |
| Cys | Glu | Ser | Glu | Ala | Asp | Trp | His | Gly | Leu | Cys | Gly | Pro | Gln | Arg | |
| | | | 980 | | | | | 985 | | | | | 990 | | |

APOPTOSIS INDUCER FOR CANCER CELL

CROSS-REFERENCE TO RELATED APPLICATION

This application is a continuation of U.S. patent application Ser. No. 10/556,968, filed Jan. 23, 2007, which application is a U.S. national phase of International Application No. PCT/JP04/007145, filed May 19, 2004, which application claims the benefit of Japanese Application No. 2003-140685, filed May 19, 2003, where these applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 390081_401C1_SEQUENCE_LISTING.txt. The text file is 164 KB, was created on Mar. 10, 2010, and is being submitted electronically via EFS-Web.

TECHNICAL FIELD

The present invention relates to apoptosis inducers for cancer cells, which comprise as an active ingredient a compound that suppresses the expression of a gene belonging to the RecQ DNA helicase family, or a compound that suppresses the function of the protein encoded by that gene, and screening methods to select candidate compounds for the apoptosis inducers.

BACKGROUND ART

Genes belonging to the RecQ DNA helicase family are widely present in organisms ranging from prokaryotes such as *Escherichia coli* (*E. coli*) to higher eukaryotes including humans. Conserved in the evolution process, these genes diversified along with the multicellularization of organisms. The *E. coli* RecQ gene was the first of the RecQ family genes to be discovered. This gene was identified as a gene participating in zygotic recombination and in the RecF pathway for UV damage repair (see Non-Patent Document 1). *E. coli* RecQ gene has been revealed to have the function of suppressing incorrect recombinations (see Non-Patent Document 2). The budding yeast SGS1 gene and the fission yeast Rqh1 gene are the only known RecQ homologues in these yeasts. Both of these genes mainly suppress recombination and play important roles in genome stabilization (see Non-Patent Documents 3 and 4). Higher eukaryotes carry a plurality of RecQ homologues. In humans, there are five types of genes known to belong to the RecQ family: the RecQL1 (see Non-Patent Document 6), BLM, WRN, RTS, and RecQL5 genes. Of these five, the RTS gene (see Non-Patent Document 5, and Patent Documents 1 and 2) and the RecQL5 gene (see Non-Patent Document 5, and Patent Document 3) were identified by the present inventors. BLM, WRN, and RTS genes respectively cause Bloom's syndrome (see Non-Patent Document 7), Werner's syndrome (see Non-Patent Document 8), and Rothmund-Thomson syndrome (see Non-Patent Document 9). These genes all play important roles in genome stabilization in cells.

In fibroblast cells and lymphocytic cell lines derived from patients with Werner's syndrome, chromosomal translocation and deletion, which are indexes for genome instability, have been reported to occur with a high frequency (see Non-Patent Document 10). Chromosomal breakage and sister chromatid exchange (SCE) are frequently detected in cells derived from patients with Bloom's syndrome (see Non-Patent Document 11). Trisomies of human chromosome 2 and 8 are frequently found in lymphocytes derived from patients with Rothmund-Thomson syndrome (see Non-Patent Document 12). These findings suggest that WRN helicase, BLM helicase, and RTS helicase encoded by the various causative genes of these three genetic diseases play important roles in genome stabilization in cells.

Telomere length abnormalities are seen in lymphocytic cell lines derived from patients with Werner's syndrome compared to cell lines derived from normal healthy subjects (see Non-Patent Document 13). In addition, cell immortalization was not observed in lymphocytic cell lines derived from patients with Werner's syndrome, although about 15% of cell lines derived from normal healthy subjects were immortalized after passaging (see Non-Patent Document 14). This finding indicates that WRN helicase contributes to telomere structure maintenance, and is thus essential for the immortalization (canceration) of lymphocytic cell lines.

It has been suggested that WRN helicase is associated with homologous recombination-mediated repair, because the helicase forms foci in the nucleus in response to DNA-damaging agents, and these foci are co-localized with the single-stranded DNA-binding protein RPA (which is a WRN-binding protein) and with the recombination repair factor RAD51 (see Non-Patent Document 15). In addition, WRN helicase has been known to bind to the DNA-dependent protein kinase complex (DNA-PK) and to flap endonuclease 1 (FEN-1). By binding to DNA-PK, WRN helicase plays an important role in the processing of terminals generated by DNA double strand breaks, which are repaired in the pathway of non-homologous end joining (see Non-Patent Document 16). WRN helicase is believed to activate FEN-1 by binding to it, and to provide a site for precise reconstruction of the replication fork through homologous recombination by processing Okazaki fragments (see Non-Patent Document 17). The above findings suggest that WRN helicase plays an important role in DNA repair during DNA replication.

BLM helicase is localized in the PML body, a specific structure found in the nucleus, and it binds to topoisomerase III (see Non-Patent Document 18). The helicase has the unwinding activity of the G-quadruplex structure, and thus is considered to contribute to telomere maintenance (see Non-Patent Document 19). Furthermore, the helicase has been reported to unwind the Holliday junction and to interact with the Rad51 protein (see Non-Patent Document 20). These findings suggest that BLM helicase cooperates with other DNA-metabolizing enzymes and plays important roles in recombinational DNA repair and telomere maintenance.

Of the five human proteins belonging to the RecQ DNA helicase family (RecQ1, BLM, WRN, RTS, and RecQ5), RecQ1, BLM, WRN, and RTS are expressed at negligible levels in resting cells, whereas they are expressed at high levels in cells whose proliferation has been enhanced by transformation with viruses (see Non-Patent Document 21). Furthermore, when the carcinogenic promoter TPA is added to resting cells, the expression of RecQ1, BLM, WRN, and RTS is induced along with the induction of cell division (see Non-Patent Document 21). These findings suggest the importance of the RecQ DNA helicase family in cell proliferation.

Taken collectively, these findings suggest that the RecQ DNA helicase family members may be potential target molecules for anti-cancer therapy because the family members participate in genomic repair in cells (BLM, WRN and RTS)

and also the maintenance of telomere structure (BLM and WRN), play important roles in the immortalization of certain cells (WRN), and their expression is induced following cell division (RecQ1, BLM, WRN and RTS).

In addition, the expression levels of genes in the RecQ DNA helicase family are markedly higher in tumor cells. Thus compounds that suppress tumor growth can be screened using the suppression of expression of RecQ DNA helicase family genes as an index (see Patent Document 4). It has also been suggested that compounds suppressing RecQ helicase gene expression may suppress cancer cell growth (see Patent Document 4).

However, no one has reported the correlation between the suppression of RecQ DNA helicase family gene expression and the cancer cell-specific induction of apoptosis, and there have been no findings that suggest such a correlation.

[Patent document 1] Japanese Patent Application No. Hei 9-200387

[Patent document 2] Japanese Patent Application No. Hei 11-11218

[Patent document 3] Japanese Patent Application No. Hei 10-81492

[Patent document 4] Japanese Patent Application Kokai Publication No. (JP-A) 2000-166600 (unexamined, published Japanese patent application)

[Non-Patent Document 1] Nakayama, H., Nakayama, K., Nakayama, R., Irino, N., Nakayama, Y., and Hanawalt, P. C., "Isolation and genetic characterization of a thymineless death-resistant mutant of *Escherichia coli* K12: identification of a new mutation (recQ1) that blocks the RecF recombination pathway.", Mol. Gen. Genet., 1984, Vol. 195, pp. 474-480.

[Non-Patent Document 2] Hanada, K., Ukita, T., Kohno, Y., Saito, K., Kato, J., and Ikeda, H., "RecQ DNA helicase is a suppressor of illegitimate recombination in *Escherichia coli*.", Proc. Natl. Acad. Sci. USA., 1997, Vol. 94, pp. 3860-3865

[Non-Patent Document 3] Myung, K., Datta, A., Chen, C., and Kolodner, R. D., "SGS1, the *Saccharomyces cerevisiae* homologue of BLM and WRN, suppresses genome instability and homeologous recombination.", Nat. Genet., 2001, Vol. 27, pp. 113-116

[Non-Patent Document 4] Doe, C. L., Dixon, J., Osman, F., and Whitby, M. C., "Partial suppression of the fission yeast rqh1(−) phenotype by expression of a bacterial Holliday junction resolvase.", EMBO J., 2000, Vol. 19, pp. 2751-2762

[Non-Patent Document 5] Kitao, S., Ohsugi, I., Ichikawa, K., Goto, M., Furuichi, Y., and Shimamoto, A., "Cloning of two new human helicase genes of the RecQ family: biological significance of multiple species in higher eukaryotes.", Genomics., 1998, Vol. 54, pp. 443-452

[Non-Patent Document 6] Seki, M., Miyazawa, H., Tada, S., Yanagisawa, J., Yamaoka, T., Hoshino, S., Ozawa, K., Eki, T., Nogami, M., Okumura, K. et al., "Molecular cloning of cDNA encoding human DNA helicase Q1 which has homology to *Escherichia coli* Rec Q helicase and localization of the gene at chromosome 12p12.", Nucleic Acids Res., 1994, Vol. 22, No. 22, pp. 4566-4573

[Non-Patent Document 7] Ellis, N. A., Groden, J., Ye, T. Z., Straughen, J., Lennon, D. J., Ciocci, S., Proytcheva, M., and German, J., "The Bloom's syndrome gene product is homologous to RecQ helicases.", Cell, 1995, Vol. 83, pp. 655-666

[Non-Patent Document 8] Yu, C. E., Oshima, J., Fu, Y. H., Wijsman, E. M., Hisama, F., Alisch, R., Matthews, S., Nakura, J., Mild, T., Ouais, S., Martin, G. M., Mulligan, J., and Schellenberg, G. D., "Positional cloning of the Werner's syndrome gene.", Science, 1996, Vol. 272, pp. 258-262

[Non-Patent Document 9] Kitao, S., Shimamoto, A., Goto, M., Miller, R. W., Smithson, W. A., Lindor, N. M., and Furuichi, Y., "Mutations in RECQL4 cause a subset of cases of Rothmund-Thomson syndrome.", Nat. Genet., 1999, Vol. 22, pp. 82-84

[Non-Patent Document 10] Goto, M., "Hierarchical deterioration of body systems in Werner's syndrome: implications for normal ageing.", Mech. Ageing Dev., 1997, Vol. 98, pp. 239-254

[Non-Patent Document 11] Ellis, N. A. and German, J., "Molecular genetics of Bloom's syndrome.", Hum. Mol. Genet., 1996, Vol. 5, pp. 1457-1463

[Non-Patent Document 12] Lindor, N. M., Devries, E. M., Michels, V. V., Schad, C. R., Jalal, S. M., Donovan, K. M., Smithson, W. A., Kvols, L. K., Thibodeau, S, N., and Dewald, G. W., "Rothmund-Thomson syndrome in siblings: evidence for acquired in vivo mosaicism.", Clin. Genet., 1996, Vol. 49, pp. 124-129

[Non-Patent Document 13] Tahara, H., Tokutake, Y., Maeda, S., Kataoka, H., Watanabe, T., Satoh, M., Matsumoto, T., Sugawara, M., Ide, T., Goto, M., Furuichi, Y., and Sugimoto, M., "Abnormal telomere dynamics of B-lymphoblastoid cell strains from Werner's syndrome patients transformed by Epstein-Barr virus.", Oncogene, 1997, Vol. 15, pp. 1911-1920

[Non-Patent Document 14] Sugimoto, M., Furuichi, Y., Ide, T., and Goto, M., "Incorrect us of "immortalization" for B-lymphoblastoid cell lines transformed by Epstein-Barr virus.", Virol., 1999, Vol. 73, pp. 9690-9691

[Non-Patent Document 15] Sakamoto, S., Nishikawa, K., Heo, S. J., Goto, M., Furuichi, Y., and Shimamoto, A., "Werner helicase relocates into nuclear foci in response to DNA damaging agents and co-localizes with RPA and Rad51.", Genes Cells., 2001, Vol. 6, pp. 421-430

[Non-Patent Document 16] Yannone, S. M., Roy, S., Chan, D. W., Murphy, M. B., Huang, S., Campisi, J., and Chen, D. J., "Werner syndrome protein is regulated and phosphorylated by DNA-dependent protein kinase.", J. Biol. Chem., 2001, Vol. 276, pp. 38242-38248

[Non-Patent Document 17] Brosh, R. M. Jr, von Kobbe, C., Sommers, J. A., Karmakar, P., Opresko, P. L., Piotrowski, J., Dianova, I., Dianov, G. L., and Bohr, V. A., "Werner syndrome protein interacts with human flap endonuclease 1 and stimulates its cleavage activity.", EMBO J., 2001, Vol. 20, pp. 5791-5801

[Non-Patent Document 18] Johnson, F. B., Lombard, D. B., Neff, N. F., Mastrangelo, M. A., Dewolf, W., Ellis, N. A., Marciniak, R. A., Yin, Y., Jaenisch, R., and Guarente, L., "Association of the Bloom syndrome protein with topoisomerase III alpha in somatic and meiotic cells.", Cancer Res., 2000, Vol. 60, pp. 1162-1167

[Non-Patent Document 19] Mohaghegh, P., Karow, J. K., Brosh, Jr R. M. Jr, Bohr, V. A., and Hickson, I. D., "The Bloom's and Werner's syndrome proteins are DNA structure-specific helicases.", Nucleic Acids Res., 2001, Vol. 29, pp. 2843-2849

[Non-Patent Document 20] Wu, L., Davies, S. L., Levitt, N. C., and Hickson, I. D., "Potential role for the BLM helicase in recombinational repair via a conserved interaction with RAD51.", J. Biol. Chem., 2001, Vol. 276, pp. 19375-19381

[Non-Patent Document 21] Kawabe, T., Tsuyama, N., Kitao, S., Nishikawa, K., Shimamoto, A., Shiratori, M., Matsumoto, T., Anno, K., Sato, T., Mitsui, Y., Seki, M., Enomoto, T., Goto, M., Ellis, N. A., Ide, T., Furuichi, Y., and Sugimoto, M., "Differential regulation of human RecQ family helicases in cell transformation and cell cycle.", Oncogene., 2000, Vol. 19, No. 41, pp. 4764-4772.

DISCLOSURE OF THE INVENTION

The present invention was achieved under such circumstances. An objective of the present invention is to provide apoptosis inducers for cancer cells, which comprise as an active ingredient a compound that suppresses the expression of a RecQ DNA helicase family gene, or a compound that suppress the function of the protein encoded by that gene. Another objective is to provide screening methods to select candidate compounds for apoptosis inducers for cancer cells.

The present inventors conducted extensive research to achieve the above-described objectives. The expression levels of RecQ DNA helicase family genes are known to be higher in tumor cell lines (for example, cancer cells). Using siRNAs having the activity of suppressing human RecQ helicase family gene expression, the present inventors studied the influence of suppressing the expression of respective RecQ helicase family genes on cancer cell growth. As a result, the present inventors found, for the first time, that apoptosis can be induced in various cancer cells by suppressing the expression of the RecQ helicase family genes WRN, BLM, or RecQ1, and that cancer cell growth can thus be suppressed through this apoptosis. These effects were not observed in a diploid fibroblast cell line derived from normal human fetal lung. In addition, the present inventors found that, without significant side effects, WRN-siRNA and RecQ1-siRNA can inhibit in vivo tumor growth in cancer-bearing nude mice.

Thus, the RecQ helicase family genes WRN, BLM, and RecQ1 can serve as target molecules for superior anticancer agents having few side effects. Specifically, the above-described compounds are able to suppress the expression of RecQ helicase family genes, or the function of RecQ helicase proteins, and may have the activity of inducing apoptosis. Such compounds are expected to serve as anticancer agents having few side effects. For example, compounds based on the mRNA sequences of WRN, BLM, and RecQ1 that suppress the expression or activity of RecQ helicase family proteins such as siRNA, are expected to serve as anticancer agents having few side effects.

Apoptosis inducers can be screened by using the expression of RecQ helicase family genes as an index.

Specifically, the present invention relates to apoptosis inducers for cancer cells which comprise as an active ingredient a compound that suppresses the expression of a RecQ DNA helicase family gene, or a compound that suppresses the function of the protein encoded by that gene, and screening methods to select candidate compounds for apoptosis inducers for cancer cells. More specifically, the present invention provides the following:

[1] an (cancer cell-specific) apoptosis inducer for cancer cells, wherein the apoptosis inducer comprises as an active ingredient a compound that suppresses the expression of a gene belonging to the RecQ DNA helicase family;

[2] the apoptosis inducer according to [1], wherein the compound that suppresses the expression of a gene belonging to the RecQ DNA helicase family is a double-stranded RNA having RNAi activity towards that RecQ DNA helicase family gene;

[3] the apoptosis inducer according to [2], wherein the double-stranded RNA comprises a sense RNA comprising a sequence homologous to an arbitrary 20 to 30 consecutive nucleotides from the mRNA of a gene belonging to the RecQ helicase family, and an antisense RNA, comprising the sequence complementary to the sense RNA;

[4] an apoptosis inducer for cancer cells, wherein the apoptosis inducer comprises as an active ingredient a DNA that can express the double-stranded RNA having RNAi activity towards a RecQ DNA helicase family gene;

[5] the apoptosis inducer according to [1], wherein the compound that suppresses the expression of a RecQ DNA helicase family gene is either:

(a) an antisense nucleic acid targeting a transcript of the gene belonging to the RecQ DNA helicase family, or a portion thereof; or (b) a nucleic acid having the ribozyme activity of specifically cleaving a transcript of the RecQ DNA helicase family gene;

[6] an apoptosis inducer for cancer cells, which comprises as an active ingredient a compound that suppresses a function of a protein encoded by a RecQ DNA helicase family gene;

[7] the apoptosis inducer according to [6], wherein the compound that suppresses a function of a protein encoded by a gene belonging to the RecQ DNA helicase family is any one of:

(a) a mutant protein belonging to the RecQ DNA helicase family, where the mutant protein has a dominant-negative activity towards the protein encoded by the gene belonging to the RecQ DNA helicase family;
(b) an antibody that binds to the protein encoded by the gene belonging to the RecQ DNA helicase family; or
(c) a low-molecular-weight compound that binds to the protein encoded by the gene belonging to the RecQ DNA helicase family;

[8] the apoptosis inducer according to any one of [1] to [7], wherein the gene belonging to the RecQ DNA helicase is the WRN gene, the BLM gene, or the RecQ1 gene;

[9] the apoptosis inducer according to any one of [1] to [7], wherein the nucleotide sequence of the gene belonging to the RecQ DNA helicase family is the nucleotide sequence of any one of SEQ ID NOs: 6 to 30;

[10] the apoptosis inducer according to any one of [2] to [4], wherein either strand of the double-stranded RNA with RNAi activity comprises the nucleotide sequence of any one of SEQ ID NOs: 1 to 5, 31 to 40, and 43 to 69;

[11] an anticancer agent which comprises the apoptosis inducer according to any one of [1] to [10], as an active ingredient;

[12] a method of screening for a candidate compound for a cancer cell apoptosis inducer (a screening method for an apoptosis inducer for a cancer cell), which comprises the steps of:

(a) contacting a test compound with a protein encoded by a gene belonging to the RecQ DNA helicase family or a partial peptide thereof;
(b) assaying the binding activity between the protein, or the partial peptide thereof, and the test compound; and
(c) selecting a compound that binds to the protein encoded by the gene belonging to the RecQ DNA helicase family, or the partial peptide thereof;

[13] a method of screening for a candidate compound for a cancer cell apoptosis inducer (a screening method for an apoptosis inducer for a cancer cell), which comprises the steps of:

(a) contacting a test compound with cells expressing a gene belonging to the RecQ DNA helicase family or with an extract of those cells;
(b) determining the expression level of the gene belonging to the RecQ DNA helicase family; and
(c) selecting a compound that reduces the expression level by comparing the level with that determined in the absence of the test compound;

[14] a method of screening for a candidate compound for a cancer cell apoptosis inducer (a screening method for an apoptosis inducer for a cancer cell), which comprises the steps of:
(a) contacting a test compound with cells or an extract of those cells, wherein the cells have a DNA comprising a structure in which a reporter gene is operably linked to a transcriptional regulatory region of a gene belonging to the RecQ DNA helicase family;
(b) determining the expression level of the reporter gene; and
(c) selecting a compound that reduces the expression level by comparing the level with that determined in the absence of the test compound;

[15] a method of screening for a candidate compound for a cancer cell apoptosis inducer (a screening method for an apoptosis inducer for a cancer cell), which comprises the steps of:
(a) contacting a test compound with a protein encoded by a gene belonging to the RecQ DNA helicase family, or a cell expressing that protein or an extract of that cell;
(b) determining the activity of the protein; and
(c) selecting a compound that reduces the activity of the protein by comparing the level with that determined in the absence of the test compound;

[16] the method according to any one of [12] to [15], wherein the gene belonging to the RecQ DNA helicase family is the WRN gene, BLM gene, or RecQ1 gene; and

[17] a method for producing the apoptosis inducer according to [1] or [6] as a pharmaceutical composition, which comprises the steps of:
(a) screening for a compound using the method according to any one of [12] to [16] and
(b) combining the compound with a pharmaceutically acceptable carrier.

Preferably, the above-mentioned genes belonging to the RecQ DNA helicase family are human genes belonging to the RecQ DNA helicase family.

The present inventors revealed, for the first time, that apoptosis can be induced in cancer cells (tumor cells) by suppressing the expression of RecQ DNA helicase family genes. Thus, the present invention provides apoptosis inducers that comprise as an active ingredient a compound that suppresses the expression of a RecQ DNA helicase family gene. The apoptosis inducers of the present invention comprise the activity of selectively inducing apoptosis in cancer cells in particular. Specifically, a preferable embodiment of the present invention provides pharmaceutical agents comprising the activity of selectively (specifically) inducing apoptosis in cancer cells, where the pharmaceutical agents comprise as an active ingredient a compound that suppresses the expression of a RecQ DNA helicase family gene, or the function of the protein encoded by that gene.

The term "apoptosis" generally refers to cell death actively induced by the cell itself due to a physiological condition. Morphological features of apoptosis include, for example, chromosome condensation in the cell nucleus, nuclear fragmentation, loss of microvilli on the cell surface, and cytoplasmic shrinkage. Thus, as used herein, the term "apoptosis-inducing activity" refers to, for example, the activity of inducing in cells any of the above-described morphological features of apoptosis, but is not limited to those described above. One skilled in the art can appropriately assess whether apoptosis induction in cells is taking place or not.

For example, the present invention's apoptosis inducers for cancer cells can be anticancer agents (carcinostatic agents) having apoptosis-inducing activity as their mechanism of action.

More specifically, genes belonging to the RecQ DNA helicase family (hereinafter sometimes simply referred to as "RecQ helicase genes") include the RecQ1 gene, WRN gene, BLM gene, RTS gene, and RecQ5 gene. Those skilled in the art can readily obtain information on the nucleotide sequences of these genes from public gene databases (for example, GenBank). Exemplary GenBank accession numbers of the genes described above are listed below.

RecQ1 gene: NM_002907 (SEQ ID NO: 6), NM_032941 (SEQ ID NO: 7), BC001052 (SEQ ID NO: 8), D37984 (SEQ ID NO: 9), and L36140 (SEQ ID NO: 10).

WRN gene: NM_000553 (SEQ ID NO: 11), AF091214 (SEQ ID NO: 12), L76937 (SEQ ID NO: 13), and AL833572 (SEQ ID NO: 14).

BLM gene: U39817 (SEQ ID NO: 15), NM_000057 (SEQ ID NO: 16), and BC034480 (SEQ ID NO: 17).

RTS gene: NM_004260 (SEQ ID NO: 18), AB006532 (SEQ ID NO: 19), BC020496 (SEQ ID NO: 20), and BC011602 (SEQ ID NO: 21), and BC013277 (SEQ ID NO: 22).

RecQ5 gene: NM_004259 (SEQ ID NO: 23), AK075084 (SEQ ID NO: 24), AB006533 (SEQ ID NO: 25), AB042825 (SEQ ID NO: 26), AB042824 (SEQ ID NO: 27), AB042823 (SEQ ID NO: 28), AF135183 (SEQ ID NO: 29), and BC016911 (SEQ ID NO: 30).

One skilled in the art can readily obtain amino acid sequences of proteins encoded by the RecQ helicase genes of the present invention by, for example, using the accession numbers as indicated above. As examples of amino acid sequences of proteins encoded by the RecQ helicase genes of the present invention, the Sequence Listing shows the amino acid sequence of the protein encoded by each of the RecQ1 gene, WRN gene, BLM gene, RTS gene, and RecQ5 gene (the amino acid sequences of RecQ1 protein, WRN protein, BLM protein, RTS protein, and RecQ5 protein are shown in SEQ ID NO: 70, SEQ ID NO: 71, SEQ ID NO: 72, SEQ ID NO: 73, and SEQ ID NO: 74, respectively).

Depending on the presence of polymorphic variations in the nucleotide sequences, there may be multiple accession numbers for the same RecQ helicase gene. "Polymorphism" is not restricted to single-nucleotide polymorphisms (SNPs), such as mutations due to the substitution, deletion, or insertion of a single nucleotide, but also includes mutations due to the substitution, deletion, or insertion of several continuous nucleotides. Therefore, the RecQ helicase gene nucleotide sequences are not limited to the sequences available under the accession numbers described above. Likewise, amino acid sequences of proteins encoded by the RecQ helicase genes are also not limited to the amino acid sequences shown in SEQ ID NOs: 70 to 74. Specifically, the above-described proteins of the present invention are not limited to the amino acid sequences shown in SEQ ID NOs: 70 to 74; and include proteins functionally equivalent to any one of the proteins as shown in SEQ ID NOs: 70 to 74, and comprising amino acid sequences with one or more amino acid additions, deletions, substitutions, and/or insertions in the amino acid sequences shown in SEQ ID NOs: 70 to 74.

Preferable RecQ helicase genes of the present invention include, for example, the WRN gene, BLM gene, and RecQ1 gene. The RecQ helicase genes of the present invention typically include, but are not limited to, those derived from animals, more preferably those derived from mammals, and most preferably those derived from humans.

Preferable compounds that suppress the expression of a RecQ helicase gene of the present invention include, for example, double-stranded RNA having RNA interference (RNAi) activity towards the RecQ helicase gene. In general, the term "RNAi" refers to a phenomenon where target gene expression is inhibited by inducing disruption of the target gene mRNA. This disruption is caused by introducing into cells a double-stranded RNA that comprises, a) a sense RNA comprising a sequence homologous to the target gene mRNA sequence, and b) an antisense RNA comprising a sequence complementary to the sense RNA. While the precise RNAi mechanism remains unclear, it is thought that an enzyme called DICER (a member of the RNase III nuclease family) contacts double-stranded RNA, decomposing it into small fragments called "small interfering RNA" or "siRNA". This siRNA is also included in the double-stranded RNA comprising RNAi activity of the present invention. Furthermore, DNAs that allow the expression of the double-stranded RNA of the present invention are also included in the present invention. Specifically, the present invention provides DNAs (vectors) that allow the expression of a double-stranded RNA of the present invention. These DNAs (vectors) that allow the expression of a double-stranded RNA of the present invention are typically DNAs comprising a structure where a DNA encoding one strand of the double-stranded RNA, and a DNA encoding the other strand of the double-stranded RNA, are operably linked to a promoter. Those skilled in the art can readily prepare an above-described DNA of the present invention with routinely-used genetic engineering techniques. More specifically, expression vectors of the present invention can be prepared by appropriately inserting DNA encoding an RNA of the present invention into various known expression vectors.

The RNA used to achieve RNAi need not be completely identical (homologous) to the RecQ helicase gene or a portion of the gene; however such an RNA is preferable.

The double-stranded RNA comprising RNAi activity of the present invention is typically a double-stranded RNA that includes a) a sense RNA comprising a sequence homologous to an arbitrary RNA region of continuous nucleotide residues from the RecQ helicase gene mRNA, and b) an antisense RNA comprising a sequence complementary to the sense RNA. The above-mentioned "arbitrary RNA region of continuous nucleotide residues" is typically 20 to 30 nucleotides in length, and preferably 21 to 23 nucleotides in length. The length of the double-stranded RNA of the present invention is however not limited, because long-chain RNA that has no RNAi activity when intact may decompose to form siRNA comprising RNAi activity in cells. Furthermore, a long-chain double-stranded RNA corresponding to the full-length or near full-length mRNA of the RecQ helicase gene can be, for example, pre-digested with DICER, and the resulting decomposition products can be used as an apoptosis inducer of the present invention. The decomposition products are expected to contain double-stranded RNA molecules (siRNA) comprising RNAi activity. In this method, it is not necessary to select an mRNA region expected to comprise RNAi activity. Specifically, it is not essential to determine the RecQ helicase mRNA region comprising RNAi activity.

Usually, double-stranded RNAs comprising an overhang of several nucleotides at their ends are known to have a high RNAi activity. It is preferable that the double-stranded RNAs of the present invention comprise an overhang of several nucleotides at the ends. There is no limitation as to the length of the overhang nucleotide sequence, but it preferably comprises two nucleotide residues. A double-stranded RNA comprising an overhang of, for example, TT (a thymine doublet), UU (a uracil doublet), or some other nucleotide (most preferably, a molecule comprising a double-stranded RNA of 19 nucleotides and an overhang of two nucleotides (TT)) can be suitably used in the present invention. The double-stranded RNA of the present invention also includes molecules in which the overhanging nucleotides are DNAs.

Those skilled in the art can appropriately prepare the above-described "double-stranded RNA comprising RNAi activity towards a RecQ helicase gene" of the present invention based on the nucleotide sequence of a RecQ helicase gene that is the target of the double-stranded RNA. The nucleotide sequences of RecQ helicase genes can readily be obtained from public gene databases, as described above. For example, a double-stranded RNA of the present invention can be prepared based on the nucleotide sequence of any one of SEQ ID NOs: 6 to 30. Specifically, the selection of an arbitrary consecutive RNA region of an mRNA transcript based on the nucleotide sequence of any one of SEQ ID NOs: 6 to 30, and preparation of a double-stranded RNA corresponding to this region would be an easy task for one skilled in the art.

It is not essential to have information on the full-length nucleotide sequence of a gene (the target gene) from which the double-stranded RNA of the present invention is derived. It is enough that the arbitrary RNA region comprising consecutive nucleotides (for example, 20 to 30 nucleotides) which is to be selected has been identified. Thus, the double-stranded RNA of the present invention can be prepared based on the nucleotide sequence of a fragment of a gene, such as an Expressed Sequence Tag (EST), whose mRNA sequence has been determined partially, but not completely. The accession numbers and names of EST sequences in the GenBank database with a high homology to human genes belonging to the RecQ DNA helicase family are shown below. However, this list includes only a few examples of the many EST sequences. Those skilled in the art can readily obtain sequence information on appropriate EST fragments from public databases.

(a) RecQ1 gene: BQ436743, AU130503, BI756143, BQ962215.1|BQ962215, AU117557, BQ049370, AU129387, BQ882675, BM015357, BG392546, AU131006, BU190089, BE870195, BM786040, BQ182943, AU138156, AW629737, CA489724, BF031494, AA258050, AW149458, BG113470, BG177944, AV718094, BQ952333, BQ647346, AU127897, AA830035, BQ215072, BE708578, BM467595, AL042375, AA298927, BU858680, CB158017, AA298835, BG536173, AU280724, BU194296, BI090858, BG118947, AA070943, BG530720, BG529492, AW505210, AW673131, BE888299, BE794392, CA394258, Z33439, BX093234, AA298951, AA459772, BG542269, BF344325, BQ359629, CA396832, AA670042, BF061797, AI652053, CB306566, CB155969, BU160790, BM263857, AW338719, AI872607, AI560139, CA450066, CA310830, BQ776691, BM980368, BM976615, BF436358, BE502851, AW864567, AW057629, AI685944, AI671558, AI636512, AI478320, AI474213, AI434812, AI223294, AA969326, AA939175, AA889357, AA804459, AA456585, AA287557, BM151219, AI261327, AW779519, AW867647, T71941, BI559810, AW182531, BE246521, CA450299, CA311010, and AW672788.

(b) WRN gene: AW965099, AL707510, AL709832, BM785803, BG714322, BM552381, BF103840, BQ305613, T39125, BG992948, BQ305407, BU633322, CB156864, AA344201, AA373157, W40393, AA287985, AA193296, AA193286, BM721721, R58879, AW016548, AI203498, H80461, AA835784, BQ354585, N64051, A1025669, AW102683, BU683758, AA905633, BE939929, AI457716, BE787985, AA778924, BG941850, and BQ774611.

(c) BLM gene: AL556823, AL556853, BM451903, BI091601, BG199179, BI091772, BQ230262, BG772975, BG875917, BM542461, BM040993, BE618504, BM041661, BG574669, BI667071, BE538092, BG721596, AW502890, BM804157, CB243435, AL120858, BX106802, BE889560, BQ316432, BE963549, AI394601, BG397477, BG756262, BX283839, AI097184, AW503829, AW404657, BE535950, AA747832, AI590599, AW504704, AI114820, AA904488, BG531593, BE245802, BU588736, BQ359304, AA974756, BE778486, BM151892, AA769336, BG192554, BG187329, AW575595, AA214549, AA480209, AI423875, AW173139, AI630521, CA488994, AA862803, BE940055, BU431321, AA249737, BM150628, AW138812, AA903504, BE245666, BG210806, BG185919, BG182955, H53763, BG217661, AA887818, AA643177

(d) RTS gene: AL561020, BU902971, CA454998, BM557643, BU944576, BQ065027, BQ649577, BG824628, BQ072016, AL582326, BU173357, BU902969, BE560845, BG388102, BG337750, CA489272, BM763376, BQ646647, BU957442, BG757074, BE514063, BU171530, BQ218075, BE513519, BE379488, BE513709, BQ668351, BG338114, BQ883533, BM724503, BM849415, BE295951, BI457058, BG398209, BM679729, BM794167, BM853252, BM461584, BE466-402, BE281293, BE378846, BQ215879, BM847781, BE906701, BX116159, BE349634, BG337918, H16879, BG339379, AW236527, BM854499, AI858255, BG954668, $BF_{513150}$, BM144460, BM144537, AI886385, AI590776, BM848938, AI765149, CA449577, BM763607, AA768048, AA595239, BU729459, BM702983, AI872334, AA401146, BF909603, BE790022, AA984927, BM796016, BF935882, H16770, AI471262, AA627850, BG991513, BF800269, BX095851, BQ576069, BG059979, BF000493, AI341050, AI206129, BE243589, AW304768, BF115628, BE869080, AI365167, BQ651717, AA620446, BG822953, and AL042193.

(e) RecQ gene: BU187406, BI916256, BQ954275, BQ932656, BQ924931, BG762566, AL525351, BQ316263, BG424888, BG721800, BQ049337, BQ061205, BQ059196, BM449612, BM469366, BX099953, CB270726, BG763254, BU431740, BQ375153, BF982170, AI567000, AI671940, CB155215, AA155882, BI772198, AW368882, BQ322863, AI310229, BF896710, BF896709, BF182856, AL600850, BI198364, BI200066, AA155835, BE314216, BE313572, BE263134, BE261456, AI363275, AI218469, BQ316256, AW605932, and BI116483.

Specifically, a preferred embodiment of the present invention provides an apoptosis inducer that comprises a double-stranded RNA with RNAi activity, which comprises as one strand an RNA region of continuous nucleotides in mRNA corresponding to a gene of any one of the sequences of SEQ ID NOs: 6 to 30 or to any of the ESTs shown above.

As described above, some identical RecQ helicase genes comprise various polymorphic sequences. Those skilled in the art can appropriately design a sequence of RNA expected to have RNAi activity by basing the design on any one of the above-described SEQ ID NOs: 6 to 30 or EST sequences, for example by evaluating information on a RecQ helicase gene obtained from public databases for polymorphisms. An apoptosis inducer comprising such RNA is also included in the present invention. In addition, those skilled in the art can also prepare an apoptosis inducer by appropriately selecting, from a number of double-stranded RNAs of the present invention, an RNA comprising optimal RNAi activity.

The above-described "double-stranded RNA comprising RNAi activity" of the present invention is preferably exemplified by the double-stranded RNAs described in FIG. 1 or 2. In addition, siRNA molecules comprising a nucleotide sequence shown in FIG. 3 or the Sequence Listing as either strand of the double-stranded RNA (siRNA molecules comprising the nucleotide sequence of any one of SEQ ID NOs: 1 to 5, 31 to 40, and 43 to 69, and a complementary strand thereof) are also included. Specifically, an embodiment of the present invention provides cancer cell-specific apoptosis inducers that comprise as an active ingredient an siRNA molecule in which either strand of the double-stranded RNA having an RNAi effect comprises the nucleotide sequence of any one of SEQ ID NOs: 1 to 5, 31 to 40, and 43 to 69 (an siRNA molecule comprising the nucleotide sequence of any one of SEQ ID NOs: 1 to 5, 31 to 40, and 43 to 69, and a complementary strand thereof).

Another preferred embodiment of the present invention provides apoptosis inducers in which the compound that suppresses gene expression of the RecQ DNA helicase family is the compound of (a) or (b) described below:

(a) an antisense nucleic acid targeting a transcript of a RecQ DNA helicase family gene, or a portion thereof; and (b) a nucleic acid having the ribozyme activity of specifically cleaving the transcript of a RecQ DNA helicase family gene.

As used herein, the term "nucleic acid" refers to RNA and DNA. Methods well known to those skilled in the art for inhibiting (suppressing) the expression of a specific endogenous gene include those using antisense technology. Multiple factors contribute to the inhibition of a target gene expression by an antisense nucleic acid. These factors include, for example, inhibition of transcription initiation through triplex formation; inhibition of transcription through hybrid formation with a sequence at the site of a local open loop structure made by RNA polymerase; inhibition of transcription through hybrid formation with the RNA being synthesized; inhibition of splicing through hybrid formation with a sequence at an intron-exon junction; inhibition of splicing through hybrid formation with a sequence at the site of spliceosome formation; inhibition of transfer from the nucleus to the cytoplasm through hybrid formation with mRNA; inhibition of splicing through hybrid formation with a sequence at the capping site or poly(A) site; inhibition of translation initiation through hybrid formation with a sequence at the site of binding of the translation initiation factor; inhibition of translation through hybrid formation with a sequence at the ribosome binding site near the initiation codon; inhibition of peptide chain elongation through hybrid formation with a sequence at the site of the translational region or polysome binding site of the mRNA; and inhibition of gene expression through hybrid formation with a sequence at the site of interaction between the protein and the nucleic acid. Thus, an antisense nucleic acid inhibits target gene expression by inhibiting various processes, such as transcription, splicing and translation (Hirashima and Inoue, Shin Seikagaku Jikkenkoza 2 (New Lecture for Experimental Biochemistry 2), Kakusan IV (Nucleic Acid IV), Replication and Expression of Genes; Ed., Japanese Biochemical Society, Tokyo Kagaku Dozin Co., Ltd., pp. 319-347, 1993).

Antisense nucleic acids used in the present invention may inhibit the expression of a RecQ helicase gene through any one of the actions described above. In one embodiment, an antisense sequence is designed to be complementary to the 5'-untranslated region of a RecQ helicase gene mRNA. Thus such an antisense sequence is expected to effectively inhibit translation of that gene. A sequence complementary to the coding region or 3'-untranslated region can also be used for this purpose. Thus, a nucleic acid comprising the antisense sequence corresponding to the sequence of the translated as well as the untranslated regions of the RecQ helicase gene can be included as an antisense nucleic acid used in the present invention. The antisense nucleic acid to be used is ligated downstream of an appropriate promoter and preferably ligated with a sequence comprising a transcription termination signal at the 3' end. The antisense nucleic acid to be used for clinical applications is typically a synthetic oligomer. Such synthetic oligomers include the widely used S-oligo (phosphorothioate oligo nucleotide) in which S (sulfur) has been substituted for O (oxygen) at the phosphate ester bond, thus reducing sensitivity to nuclease digestion and maintaining antisense nucleic acid activity. S-oligo is currently being tested as an antisense drug in clinical trials where it is administered directly to affected areas. This S-oligo is also suitable for use in the present invention. It is preferable that the antisense nucleic acid sequence is complementary to the target gene sequence or a portion thereof; however perfect complementarity is not necessary as long as the antisense nucleic acid effectively suppresses target gene expression. The transcribed RNA has preferably 90% or higher complementarity, and most preferably 95% or higher complementarity to the target gene transcript. The length of the antisense nucleic acid used to effectively suppress target gene expression is at least 15 nucleotides or longer, preferably 100 nucleotides or longer, and more preferably 500 nucleotides or longer.

The inhibition of RecQ helicase gene expression can also be achieved using a ribozyme or ribozyme-encoding DNA. The term "ribozyme" refers to an RNA molecule comprising catalytic activity. Ribozymes can have a variety of activities, and can be designed to have the activity of cleaving RNA in a site-specific fashion. Ribozymes such as group I intron-type ribozymes and M1 RNA, which are RNase P ribozymes, are 400 nucleotides or more in length. Others such as hammerhead and hairpin ribozymes have active sites comprising about 40 nucleotides (M. Koizumi and E. Otsuka, Tanpakushitsu Kakusan Koso (Protein, Nucleic acid, and Enzyme), 1990, 35, 2191).

For example, the autolytic domain of a hammer-head ribozyme cleaves the 3' side of C15 in the sequence G13U14C15. Base pairing between U14 and A9 plays an important role in this activity, and A15 or U15 can be cleaved instead of C15 (Koizumi, M. et al., FEBS Lett, 228: 228, 1988). A restriction enzyme-like RNA-cleaving ribozyme that recognizes the target RNA sequences UC, UU or UA can be produced by designing the ribozyme such that the substrate binding site complements the RNA sequence near the target site (Koizumi, M. et al., FEBS Lett, 239: 285, 1988; M. Koizumi and E. Otsuka, Tanpakushitsu Kakusan Koso (Protein, Nucleic acid, and Enzyme), 35:2191, 1990; and Koizumi, M. et al., Nucl. Acids Res., 17: 7059, 1989).

The hairpin ribozyme can also be used for the purposes of the present invention. This ribozyme is found, for example, in the minus strand of tobacco ring spot virus satellite RNA (Buzayan, J. M., Nature, 323: 349, 1986). A target specific RNA-cleaving ribozyme can also be produced from a hairpin ribozyme (Kikuchi, Y. and Sasaki, N., Nucl. Acids Res., 19: 6751, 1991; Kikuchi, H., Kagaku to Seibutsu (Chemistry and Biology), 30: 112, 1992). Thus, the expression of a RecQ helicase gene of the present invention can be inhibited by specifically digesting the gene transcript using a ribozyme.

Furthermore, the present invention relates to apoptosis inducers comprising as an active ingredient a compound that suppresses the function (activity) of a protein encoded by a RecQ DNA helicase family gene (herein, also abbreviated as "RecQ helicase protein").

The RecQ helicase proteins of the present invention further include mutant and homologous proteins functionally equivalent to RecQ helicase proteins, but whose amino acid sequences contain one or more amino acid deletions, substitutions or additions compared to the normal RecQ helicase protein sequence. Herein, the term "functionally equivalent protein" refers to a protein having the same activity as a RecQ helicase protein. Alternatively, a protein functionally equivalent to a RecQ helicase protein can be defined as a protein having, for example, 90% or higher homology, preferably 95% or higher homology, and more preferably 99% or higher homology to the amino acid sequence of the RecQ helicase protein.

A preferred embodiment of the present invention provides apoptosis inducers in which the compound suppressing the function (activity) of a protein encoded by a RecQ DNA helicase gene is a compound of any one of (a) to (c) below. These compounds have the activity of inducing apoptosis in cells, cancer cells in particular, through inhibiting the function or activity of a RecQ helicase protein:

(a) a mutant RecQ DNA helicase family protein comprising dominant-negative activity against a protein encoded by a RecQ DNA helicase family gene;

(b) an antibody that binds to a protein encoded by a RecQ DNA helicase family gene; and (c) a low-molecular-weight compound that binds to a protein encoded by a RecQ DNA helicase family gene.

The phrase "mutant RecQ DNA helicase protein comprising dominant-negative activity against a protein encoded by a RecQ DNA helicase family gene" described above in (a) refers to a mutant RecQ helicase protein comprising the function of eliminating or reducing the function of the endogenous wild-type protein. An example is a mutant RecQ helicase family protein reported to have no ATP hydrolysis activity. This mutant is formed when alanine or methionine is substituted for lysine residues in motif I (ATP-binding motif), one of seven highly conserved helicase motifs in the helicase domain of a RecQ helicase family protein. This mutant functions as a dominant negative mutant protein. Thus, the dominant negative mutant of the present invention is exemplified by a mutant in which the lysine residues in the above-described motif I have been replaced with other amino acid residues.

The antibody that binds to a RecQ helicase protein, described in (b), can be prepared by a method known to those skilled in the art. When the antibody is a polyclonal antibody, it can be prepared, for example, using the following method: Antiserum is obtained by immunizing small animals such as rabbits with a natural or recombinant RecQ helicase protein, or a recombinant RecQ helicase protein expressed as a fusion protein with GST in microorganisms such as *E. coli*, or a partial peptide thereof. The antibody is purified from the serum using, for example, ammonium sulfate precipitation, a protein A column, a protein G column, DEAE ion-exchange chromatography, an affinity column where a RecQ helicase protein or synthetic peptide thereof has been immobilized, etc. Alternatively, a monoclonal antibody can be produced by, for example, immunizing a small animal such as mouse with the RecQ helicase protein or a partial peptide thereof, removing the spleen, gently grinding the spleen to separate cells, fusing the cells with mouse myeloma cells using a reagent such as polyethylene glycol, and then screening the fused cells (hybridomas) to select clones that produce antibodies that bind to the RecQ helicase protein. These hybridomas are then transplanted into a mouse peritoneal cavity and the ascites are collected from the same mouse. The monoclonal antibody thus prepared can be purified using, for example, ammonium sulfate precipitation, a protein A column, a protein G column, DEAE ion-exchange chromatography, an affinity column where a RecQ helicase protein or synthetic peptide thereof has been immobilized, etc.

There is no limitation as to the type of antibodies of the present invention, as long as they can bind to a RecQ helicase protein of the present invention. The antibodies include human antibodies, humanized antibodies prepared using genetic recombination, antibody fragments thereof, and modified antibodies, in addition to the polyclonal antibodies and monoclonal antibodies described above.

The RecQ helicase protein of the present invention to be used as an immunization antigen to obtain antibodies need not derive from the same species as the protein. However, mammalian proteins are preferable, for example, proteins from mice and humans, and proteins from humans are especially preferable.

Proteins to be used as an immunization antigen in the present invention may be intact proteins as well as partial peptides derived from those proteins. Such partial protein peptides include, for example, protein amino (N)-terminal fragments and carboxyl (C)-terminal fragments. As used herein, "antibody" usually refers to an antibody which reacts with a full-length protein or a fragment thereof.

In addition to obtaining the above-described hybridomas by immunizing non-human animals with an antigen, hybridomas producing a desired human antibody comprising binding activity with the protein can also be prepared in vitro by sensitizing human lymphocytes, for example, human lymphocytes infected with EB virus, with the protein, cells expressing the protein, or a lysate of those cells, and fusing these sensitized lymphocytes with immortalized human myeloma cells, for example, U266 cells. When an antibody of the present invention is intended to be administered into human bodies (antibody therapy), a human antibody or humanized antibody is preferable to reduce the immunogenicity.

Compounds known to bind to a protein belonging to the RecQ helicase family include, for example, monoclonal and polyclonal antibodies against RecQ1 helicase, WRN helicase, BLM helicase, RTS helicase, and RecQ5 helicase.

Compounds of the present invention that suppress RecQ helicase gene expression or the function (activity) of a protein encoded by that gene may be natural or synthetic compounds. Typically, the compounds can be produced, obtained or isolated using methods known to those skilled in the art. Such compounds include, for example, compounds comprising a single molecule, such as organic compounds, inorganic compounds, nucleic acids, proteins, peptides, and sugars; and libraries of compounds, expression products of gene libraries, cell extracts, cell culture supernatants, the products of fermenting microorganisms, marine organism extracts, plant extracts, and compounds purified or isolated from such extracts.

Compounds known to inhibit the function (activity) of a RecQ helicase family protein include, for example, distamycin A and netropsin that have the activity of inhibiting WRN helicase and BLM helicase (Brosh, R. M. Jr, Karow, J. K., White, E. J., Shaw, N.D., Hickson, I. D. and Bohr, V. A., "Potent inhibition of werner and bloom helicases by DNA minor groove binding drugs.", Nucleic Acids Res. 28, 2420-2430, 2000); 3,6,9-trisubstituted acridine that has the activity of inhibiting WRN helicase and BLM helicase (Li, J. L., Harrison, R. J., Reszka, A. P., Brosh, R. M. Jr, Bohr, V. A., Neidle, S, and Hickson, I. D., "Inhibition of the Bloom's and Werner's syndrome helicases by G-quadruplex interacting ligands.", Biochemistry 40, 15194-15202, 2001); and N-methyl mesoporphyrin IX that has the activity of inhibiting *E. coli* RecQ helicase (Wu, X. and Maizels, N., "Substrate-specific inhibition of RecQ helicase.", Nucleic Acids Res. 29, 1765-1771, 2001).

The present invention also provides screening methods to select candidate compounds for apoptosis inducers for cancer cells (screening methods for apoptosis inducers for cancer cells). Compounds selected by these screening methods are expected to have apoptosis-inducing activity.

In one embodiment of these methods, the binding of a test compound to a RecQ helicase protein or partial peptide thereof is used as an index. A compound that binds to a RecQ helicase protein or partial peptide thereof is typically expected to have the activity of inhibiting the function of that RecQ helicase protein.

In the above-described method of the present invention, first, a test compound is contacted with the protein encoded by a RecQ helicase gene or partial peptide thereof. Depending on the type of index used to detect test compound binding, the RecQ helicase protein or partial peptide thereof can be, for example, a purified protein or partial peptide; a protein or partial peptide expressed within or outside of cells; or a protein or partial peptide bound to an affinity column. The test compounds used in this method can be labeled as required. Such labels include, for example, radiolabels and fluorescent labels.

The next step of this method comprises detecting the binding between the test compound and the RecQ helicase gene protein or partial peptide thereof. The binding between the test compound and the RecQ helicase protein or partial peptide thereof can be detected, for example, by using a label attached to the test compound bound to the RecQ helicase protein or partial peptide thereof. Alternatively, binding can be detected by using as an index a change in RecQ helicase protein activity induced by the binding of the test compound to that protein or partial peptide thereof which is expressed within or outside of cells.

The next step of this method comprises selecting test compounds that bind to the RecQ helicase gene protein or partial peptide thereof.

There is no limitation as to the type of test compound used in the present invention. Such compounds include, but are not limited to, for example, single unmixed compounds of organic compounds, inorganic compounds, nucleic acids, proteins, peptides, sugars, natural compounds, and such; or compound libraries, expression products of gene libraries, cell extracts, cell culture supernatants, products of fermenting microorganisms, marine organism extracts, and plant extracts; and artificially synthesized compounds.

In an alternative embodiment of the screening method of the present invention, first, a test compound is contacted with cells that express a RecQ DNA helicase family gene, or with a cell extract prepared from such cells. The phrase "cells that express a RecQ DNA helicase family gene" described above include cells expressing an endogenous RecQ helicase gene, and cells into which an exogenous RecQ helicase gene has been introduced and in which that gene is expressed. The cells in which an exogenous RecQ helicase gene is expressed can typically be prepared by introducing into host cells a vector which contains the gene. Those skilled in the art can prepare such an expression vector using routine genetic engineering techniques. In the screening methods of the present invention, cells expressing a RecQ helicase gene preferably include various tumor cells, for example, MCF7 (breast cancer), A549 (lung cancer), U2OS (osteogenic sarcoma), C33A (cervical cancer), HT1080 (fibrosarcoma), PA-1 (ovarian teratocarcinoma), Tera2 (embryonal carcinoma), T24 (bladder cancer), K562 (chronic myelocytic leukemia), Molt4 (acute lymphoblastic leukemia), A172 (glioblastoma), HeLa (cervical cancer), and HepG2 (hepatic cancer), U251 (glioblastoma), UACC62 (melanoma), Caki-1 (renal cancer), KP4 (pancreatic cancer), MKN45 (stomach cancer), and LNCaP (prostatic cancer).

Typically, but without limitation, a test compound is contacted with cells expressing a RecQ helicase gene by adding the test compound to a culture medium of the cells expressing the RecQ helicase gene. When the test compound is a protein, the contact can be achieved by introducing into the cells a DNA vector that allows protein expression.

The next step of this method comprises determining the expression level of the RecQ helicase gene. Herein, the phrase "gene expression" refers to both transcription and translation. The gene expression level can be determined using a method known to those skilled in the art. For example, mRNA can be extracted from cells expressing the RecQ helicase gene according to a conventional method, and by using this mRNA as a template, the transcriptional level of the gene can be determined using Northern hybridization or RT-PCR. Alternatively, the translational level of the gene can be determined by collecting protein fractions from the cells expressing the RecQ helicase family gene, and then detecting the expression of the RecQ helicase protein using an electrophoresis method such as sodium dodecyl sulfate-polyacrylamide gel electrophoresis (SDS-PAGE). Furthermore, the translational level of the gene can be determined by detecting the expression of the RecQ helicase protein by Western blotting analysis using an antibody against the protein. There is no limitation as to the type of antibody used for RecQ helicase protein detection, as long as the protein can be detected. Such antibodies include, for example, both monoclonal and polyclonal antibodies. For example, the above-described antibodies of the present invention can also be used.

In this method, a compound is then selected such that it causes a reduction in expression level when compared to the expression level measured in the absence of a test compound (control). The compound selected by the above-described procedure is expected to have the activity of inducing apoptosis in cancer cells. This compound may be used as an anticancer agent whose mode of action is based on apoptosis induction.

In an alternative embodiment of the screening method of the present invention, a compound that reduces the expression level of a RecQ DNA helicase family gene of the present invention is selected using a reporter gene.

In this method, a test compound is first contacted with cells (or an extract of those cells) that comprise a DNA having a structure where a reporter gene is operably linked to a transcriptional regulatory region of a RecQ helicase gene. As used herein, the phrase "operably linked" means that the transcriptional regulatory region of a RecQ helicase gene is linked to a reporter gene in such a way as to induce reporter gene expression when a transcriptional factor binds to the transcriptional regulatory region of the RecQ helicase gene. Thus, even when the reporter gene is connected with another gene and thus forms a fusion protein with that gene product, such a connection can be expressed by the phrase "operably linked", as long as the expression of the fusion protein is induced when the transcriptional factor binds to the transcriptional regulatory region of the RecQ helicase gene. Using a known method and based on the cDNA nucleotide sequence for a RecQ helicase gene, those skilled in the art can obtain from the genome the transcriptional regulatory region of that RecQ helicase gene.

There is no limitation as to the type of reporter gene used in this method, as long as it can detect the expression of the gene. Such reporter genes include, for example, the CAT gene, lacZ gene, luciferase gene, and GFP gene. The "cells that comprise a DNA having a structure where a reporter gene is operably linked to a transcriptional regulatory region of a RecQ DNA helicase family gene" include, for example, cells into which a vector with the structure where a reporter gene is operably linked to a transcriptional regulatory region of a RecQ DNA helicase family gene has been introduced. Those skilled in the art can prepare the above-described vector using routine genetic engineering techniques. The introduction of such a vector into cells can be achieved using a conventional method, for example, using calcium phosphate precipitation, electroporation, the lipofectamine method, microinjection, etc. "Cells that comprise a DNA having a structure where a reporter gene is operably linked to a transcriptional regulatory region of a RecQ DNA helicase family gene" also includes cells in which that structure has been inserted into the chromosome. The DNA structure can be inserted into the chromosome by using a method routinely used by those skilled in the art, for example, a gene transfer method using homologous recombination.

An extract of those "cells that comprise a DNA having a structure where a reporter gene is operably linked to a transcriptional regulatory region of a RecQ DNA helicase family gene" includes, for example, a mixture prepared by adding a DNA to a cell extract included in a commercially available in vitro transcription translation kit, where that added DNA comprises a structure where a reporter gene is operably linked to a transcriptional regulatory region of a RecQ DNA helicase family gene.

In this method, the "contact" can be achieved by adding a test compound into a culture medium of "cells that comprise a DNA having a structure where a transcriptional regulatory region of a RecQ DNA helicase family gene is operably linked to a reporter gene", or by adding a test compound into the above-described commercially available cell extract, which contains the DNA. However, the method of contact is not limited to these methods described above. When the test compound is a protein, the contact can also be achieved, for example, by introducing into the cells a DNA vector that directs the expression of the protein.

The next step of this method comprises determining the level of reporter gene expression. The expression level of the reporter gene can be determined by a method that depends on the type of the reporter gene and which is known to those skilled in the art. For example, when the reporter gene is the CAT gene, expression level can be determined by detecting the acetylation of chloramphenicol, mediated by the CAT gene product. When the reporter gene is the lacZ gene, expression level can be determined by detecting color development in the chromogenic compound, mediated by the catalytic action of the lacZ gene expression product. When the reporter gene is the luciferase gene, the level can be determined by detecting the fluorescence of the fluorescent compound, mediated by the catalytic action of the luciferase gene expression product. Alternatively, when the reporter gene is the GFP gene, the level can be determined by detecting the fluorescence of the GFP protein.

The next step of this method comprises selecting compounds that reduce reporter gene expression level as compared to expression level determined in the absence of a test compound. The compounds selected by the above-described procedure can be candidate compounds for apoptosis inducers for cancer cells.

In an alternative embodiment of the method of the present invention, compounds are screened using as an index the activity of a protein encoded by a RecQ DNA helicase family gene of the present invention.

In this method, a test compound is first contacted with a protein encoded by a RecQ helicase gene, or cells expressing that protein, or an extract of such cells. The activity of the protein is then determined. The activity of the protein includes, for example, DNA helicase activity and DNA-dependent ATP hydrolysis activity. Helicase activity typically means the unwinding activity of double-stranded DNA into two single-stranded DNAs. DNA helicase activity can be determined by a method known to those skilled in the art. For example a radio-labeled complementary oligo DNA is annealed with single-stranded circular M13 phage DNA to form a partially double-stranded structure. Using this structure as a substrate, the enzyme is incubated in the presence of ATP and magnesium ions. The products of this reaction are then fractionated into single-stranded and double-stranded DNA using polyacrylamide gel electrophoresis or agarose gel electrophoresis, and then detected using autoradiography. In an alternative method, complementary single-stranded DNAs, labeled with europium and Qcy7 respectively, are annealed and the resulting double-stranded DNA is used as a substrate and incubated with the enzyme in the presence of ATP and magnesium ions, whereupon the fluorescence of the europium-labeled single-stranded DNA released from the double-stranded DNA by helicase activity is determined. Alternative methods include an electrochemiluminescence-based helicase assay, scintillation proximity assay, homogeneous time-resolved fluorescence quenching assay, and DELFIA helicase assay (Zhang, L., Schwartz, G., O'Donnell, M. and Harrison, R. K., "Development of a novel helicase assay using electrochemiluminescence.", Anal. Biochem. 293, 31-37, 2001).

The activity of the above-mentioned DNA-dependent ATP hydrolysis can be determined using a method known to those skilled in the art. Such methods include, for example, a method that comprises reacting the enzyme with ATP as a substrate in the presence of magnesium ions and plasmid DNA or salmon sperm DNA, and then quantifying color development associated with the release of inorganic phosphoric acid in the conversion of ATP to ADP using malachite green.

A compound is then selected that reduces RecQ helicase protein activity, compared with activity determined in the absence of the test compound. In the above-described method, it is preferable to use a full-length RecQ helicase protein having no mutations. However, a protein whose amino acid sequence contains partial substitutions and/or deletions can also be used, as long as it has an activity equivalent to that of the RecQ helicase protein.

In the above-mentioned screening method, the RecQ DNA helicase family gene is preferably the WRN gene, BLM gene, or RecQ1 gene.

The present invention also provides anticancer agents (pharmaceutical compounds for treating cancers) which comprise as an active ingredient an apoptosis inducer of the present invention that targets cancer cells (cancer cell-specific).

The present invention also provides a method for producing an apoptosis inducer as a pharmaceutical composition. In this method a candidate compound for the apoptosis inducer for cancer cells is first selected using a screening method of the present invention. Then, the selected compound is combined with a pharmaceutically acceptable carrier. Such a pharmaceutically acceptable carrier can include, but is not limited to, for example, detergents, excipients, coloring agents, flavoring agents, preservatives, stabilizers, buffers, suspensions, isotonizing agents, binders, disintegrating agents, lubricants, fluidizing agents, and correctives. Other conventional carriers can be also used appropriately.

The pharmaceutical agents of the present invention can be formulated by adding the above-indicated carriers as required and according to a conventional method. More specifically, such carriers include: light anhydrous silicic acid, lactose, crystalline cellulose, mannitol, starch, carmellose calcium, carmellose sodium, hydroxypropyl cellulose, hydroxypropylmethyl cellulose, polyvinylacetaldiethylamino acetate, polyvinylpyrrolidone, gelatin, medium chain triglyceride, polyoxyethylene hydrogenated castor oil 60, saccharose, carboxymethyl cellulose, cornstarch, and inorganic salts.

The dosage forms for the agents described above include, for example, oral forms, such as tablets, powders, pills, dispersing agents, granules, fine granules, soft and hard capsules, film-coated tablets, pellets, sublingual tablets, and pastes; and parenteral forms, such as injections, suppositories, endermic liniments, ointments, plasters, and liquids for external use. Those skilled in the art can select the optimal dosage form depending on the administration route, subject, and such. Viral vectors such as retrovirus, adenovirus, and Sendai virus vectors, and non-viral vectors such as liposomes, may be used to introduce, into the living body, DNAs expressing proteins encoded by RecQ DNA helicase family genes, or DNAs expressing antisense RNAs, ribozymes, or siRNAs that suppress RecQ DNA helicase family genes. Alternatively, non-viral vectors such as liposomes, polymer micelles, or cationic carriers, may be used to introduce, into the living body, synthetic antisense nucleic acids or synthetic siRNAs that suppress RecQ DNA helicase family genes. The introduction methods include, for example, in-vivo and ex-vivo methods.

The present invention also includes pharmaceutical compositions comprising the above-described apoptosis-inducing activity.

Ultimately, the dose of a pharmaceutical agent or pharmaceutical composition of the present invention can be appropriately determined by a physician considering the dosage form, administration method, patient's age, weight, symptoms, etc.

BRIEF DESCRIPTION OF THE DRAWINGS

FIG. 1: Nucleotide sequences of the siRNAs used in the Examples, and the nucleotide sequences of other siRNAs which exhibited exceedingly high gene expression suppression.

FIG. 2: A continuation of FIG. 1.

FIG. 3: The nucleotide sequences of siRNAs used in the Examples, which were highly capable of suppressing the expression of RecQ1, WRN, or BLM gene. "TT" represents a DNA overhang region, and the remaining nucleotides represent RNAs that are siRNAs forming double strands with the complementary strand.

FIG. 6: The result of quantification of the expression level of RecQ1, WRN, or BLM gene in HeLa cells 48 hours after introduction of siRNA against each gene by semi-quantitative RT-PCR. NS corresponds to the non-silencing siRNA treatment.

FIG. 9: The viability of HeLa cells determined 96 hours after transfection of the HeLa cells with each siRNA against RecQ1, WRN, or BLM. Shows cell counts when the number of cells transfected with non-silencing siRNA is taken to be 100%.

BEST MODE FOR CARRYING OUT THE INVENTION

Figure 4:
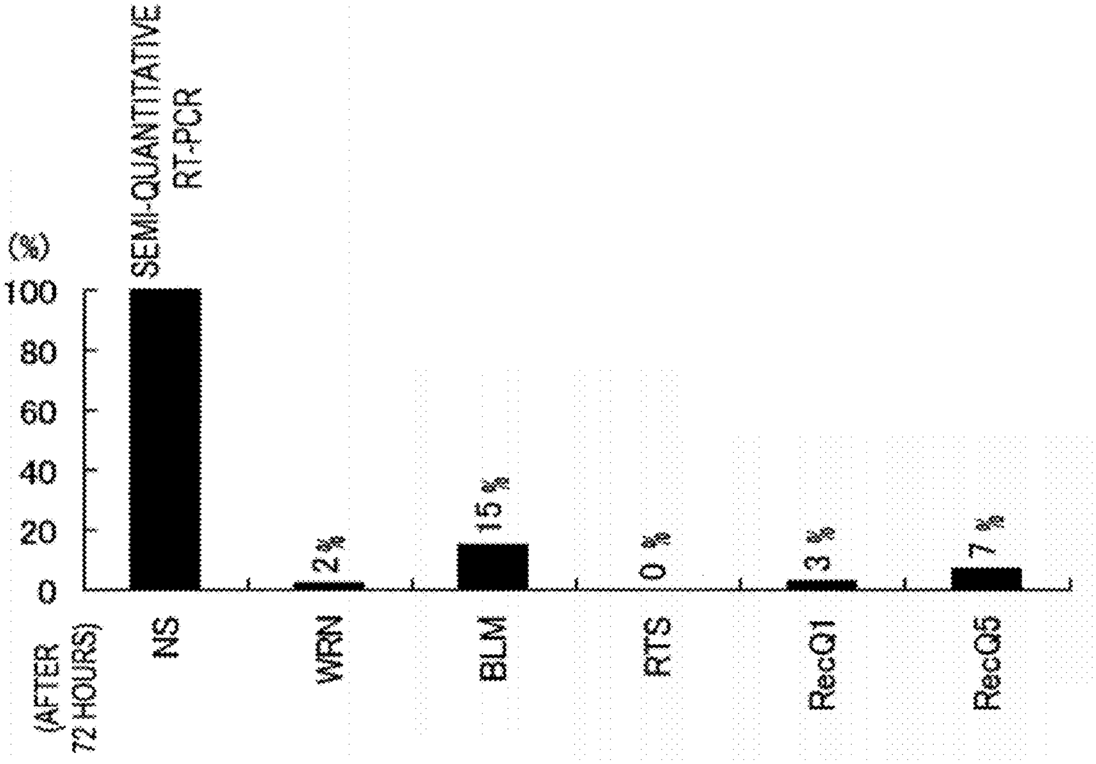
FIG. 4: A graph showing the results obtained by introducing each of the siRNAs corresponding to the five types of human RecQ helicases, WRN, BLM, RTS, RecQ1, and RecQ5, into HeLa cells respectively, and then quantifying each mRNA expression using Taqman PCR 72 hours later. NS is the control RNA.

The present invention is illustrated in detail below with reference to Examples, but it is not to be construed as being limited thereto.

EXAMPLE 1

Cell Culture

The human cells used were HeLa (uterocervical carcinoma cells), A549 (human lung cancer cells), MCF7 (human breast cancer cells), TIG3 (normal diploid fibroblast cells), U2OS (osteosarcoma), HepG2 (hepatic cancer), U251 (glioblastoma), UACC62 (melanoma), Caki-1 (renal cancer), KP4 (pancreatic cancer), MKN45 (stomach cancer), and LNCaP (prostatic cancer). All human cells were cultured under 5% $CO_2$ at 37° C. in Dulbecco's modified Eagle's medium containing 10% fetal bovine serum and 50 μg/ml gentamycin.

EXAMPLE 2

The Effect on Cancer Cell Growth of the Suppression of Expression of Five Types of Human RecQ Helicases Five siRNAs targeting each of the five types of human RecQ helicase genes (WRN, BLM, RTS, RecQ1, and RecQ5) were designed by using the method by Elbasher et al. (Elbasher, M. S. et al. Duplexes of 21-nucleotide RNAs mediate RNA interference in cultured mammalian cells. Nature 411, 494-498 (2001)) to examine the effect of suppressing the expression of each of the five human RecQ helicases on cancer cell growth. The siRNAs were synthesized by Dharmacon, Inc. and QIAGEN.

FIGS. 1 and 2 show the selected siRNAs, and the sequences used to synthesize these siRNAs (the lower-case letters represent residues homologous to the mRNA of a RecQ DNA helicase family gene), and the siRNA sequences that strongly suppressed gene expression, respectively. The Sequence Listing contains only sense strands sequences, and thus the corresponding antisense strands are omitted from the Sequence Listing.

The siRNAs were introduced into human uterocervical carcinoma-derived HeLa cells and fetal embryo-derived fibroblast TIG3 cells as normal cells. Twenty-four hours before siRNA transfection, the cells were plated in 24-well plates at a density of 1 to 3×$10^4$ cells/well. When these cells were 20 to 50% confluent, the siRNAs were transfected. Twenty-four hours after plating, cells were transfected with the siRNAs using Oligofectamine (Invitrogen) or Lipofectamine 2000 (Invitrogen) respectively, following the supplier's protocols.

Total RNA was extracted from the cells using RNeasy Mini Kits (Qiagen), 42 and 72 hours after siRNA transfection, respectively. Quantitative PCR was carried out using an ABI PRISM 7000 Sequence Detection System (Applied Biosystems). RT-PCR primers for the RecQ helicase genes and beta-actin gene, as well as TaqMan probes were purchased from Applied Biosystems. RT-PCR reactions were carried out using TaqMan One-Step RT-PCR Master Mix Reagents Kits (Applied Biosystems) according to the method described in the manual. The mRNA expression levels were compared quantitatively using beta-actin as a standard.

The expression of each mRNA in cells into which a control RNA (NS) had been introduced was taken as 100%, and then compared with the expression of each mRNA in cells into which each siRNA had been introduced. NS-siRNA is a duplex consisting of the following two strands: 5'-UUCUCCGAACGUGUCACGUdTdT-3' (SEQ ID NO: 41/"dTdT" is represented by "TT" in the Sequence Listing) and 5'-ACGUGACACGUUCGGAGAAdTdT-3' (SEQ ID NO: 42/"dTdT" is represented by "TT" in the Sequence Listing).

Figure 5:
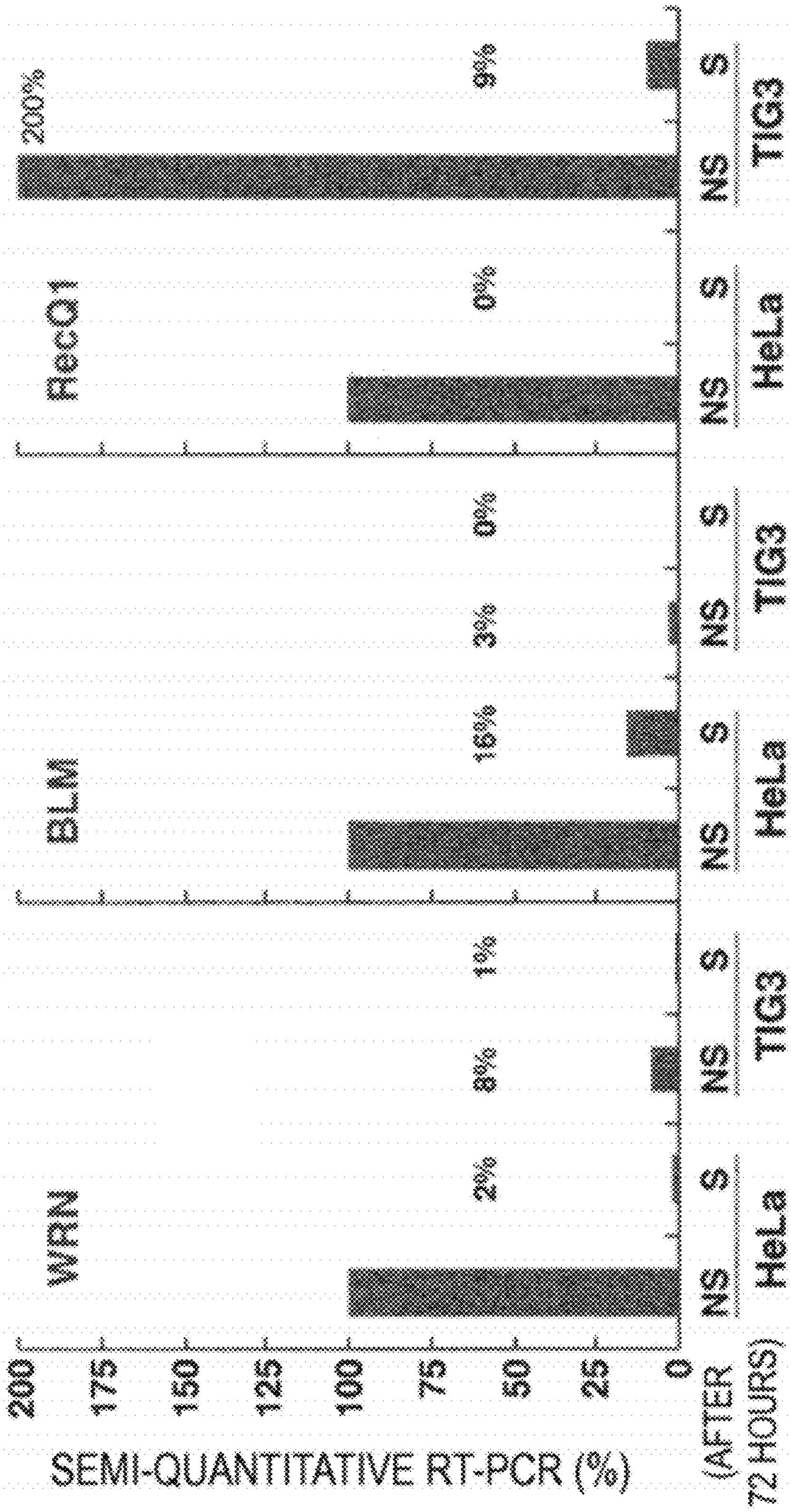
FIG. 5: Graphs showing the results obtained by semi-quantitative Taqman PCR assays for WRN, BLM, and RecQ1 mRNA expression 72 hours after the individual introduction of WRN, BLM, and RecQ1 siRNAs into TIG3 cells. NS is the control RNA.

As a result, in HeLa cells cultured for 72 hours, the siRNAs which reduced mRNA expression to the following values were identified: 2% in the case of WRN; 15% in the case of BLM; 0% in the case of RTS; 0% in the case of RecQ1; and 7% in the case of RecQ5 (FIG. 4). In contrast, in TIG3 cells, mRNA expression of WRN, BLM, and RecQ1 were suppressed down to 1%, 0%, and 9% respectively. Thus, expression was markedly suppressed when compared with expression in TIG3 cells in which control RNA (NS) had been introduced (FIG. 5).

Next, the present inventors also designed siRNAs against three types of human RecQ helicases, RecQ1, WRN, and BLM, by the same procedure as described above, and selected 14, 11, and 7 types of siRNAs for RecQ1, WRN, and BLM, respectively. The selected sequences also include some sequences already shown above. The selected siRNA sequences are shown in FIG. 3. In the Sequence Listing, only sense stands are shown while corresponding antisense strands are not.

The siRNAs were introduced into HeLa cells. 48 hours after introduction, the expression levels of RecQ1, WRN, and BLM genes were quantitated by semi-quantitative RT-PCR. The gene expression levels after introduction of each siRNA were compared taking the expression levels after treatment with non-silencing siRNA (NS) as 100%.

As a result, all 14 types of siRNAs for RecQ1 and the siRNAs for WRN3, WRN4, WRN6, and WRN12 exhibited 90% or stronger gene-suppression effect, while the siRNAs for BLM2, BLM3, BLM4, BLM5, and BLM7 suppressed the gene expression level by 80% or more (FIG. 6).

Western blot analysis was used to determine the expression levels of the proteins WRN, BLM, RTS, RecQ1, and RecQ5 in HeLa cells in which each mRNA expression was suppressed. The cells were harvested 48 and 72 hours, respectively, after transfection with the siRNAs, and then lysed in RIPA solutions (50 mM Tris-HCl, pH 8.0, 0.1% SDS, 1% Triton X 100, and 1% sodium deoxycholate). The proteins extracted were fractionated using SDS-PAGE on a polyacrylamide gel with a concentration gradient of 4% to 20%. The fractionated proteins were transferred onto a polyvinylidene difluoride (PVDF) membrane. As the primary antibodies, polyclonal antibodies against RecQ1 and BLM, monoclonal antibodies against WRN, RTS, and RecQ5, and β-actin antibody were used. The secondary antibody was an antibody conjugated with peroxidase. The proteins were detected by chemical luminescence using ECL Plus Western Blotting Detection Reagents (Amersham Biosciences).

Figure 7:
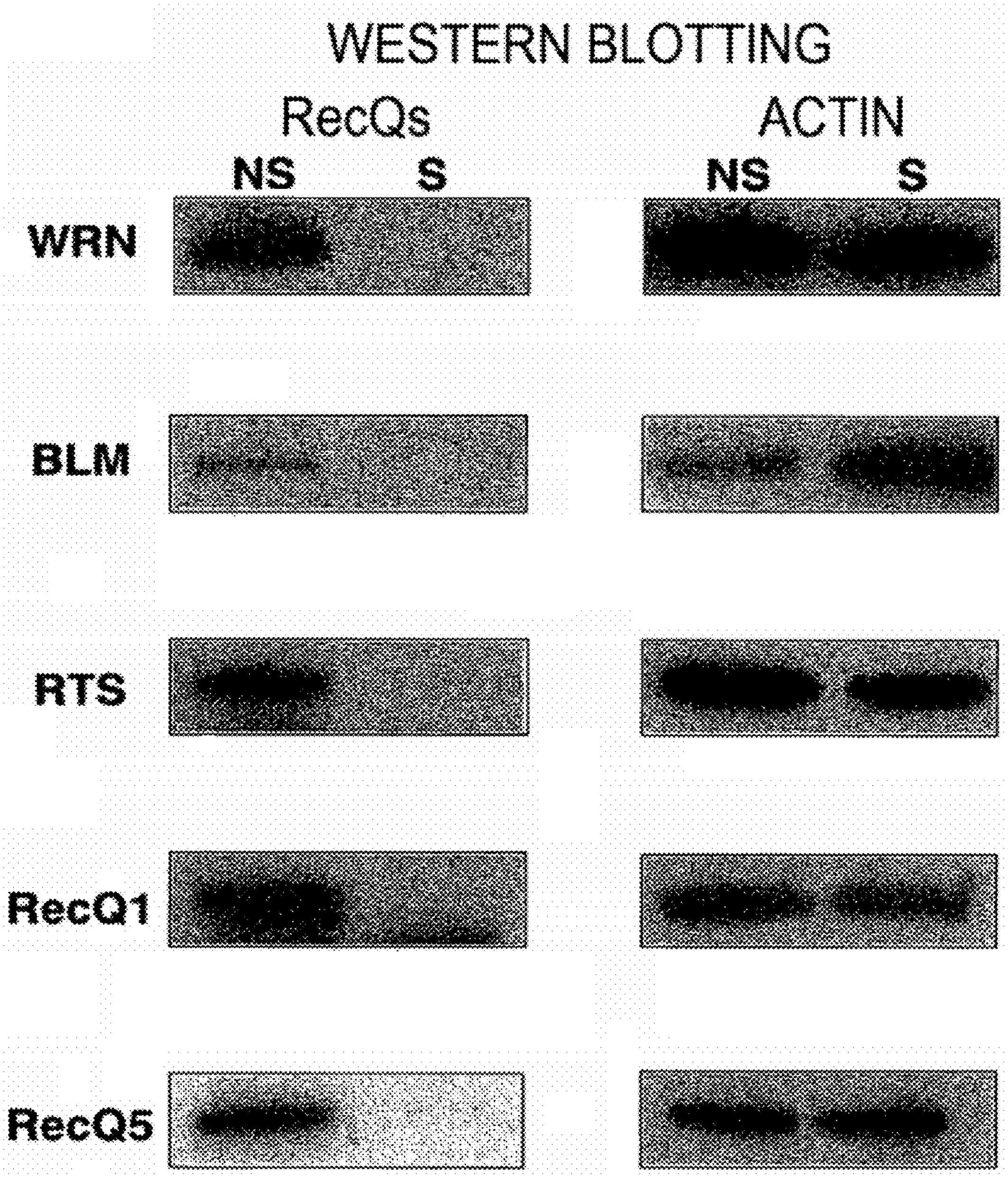
FIG. 7: Photographs showing the results obtained by Western blot analysis for the expression levels of the proteins, WRN, BLM, RTS, RecQ1, and RecQ5, in HeLa cells in which mRNA expression was revealed to be suppressed.

As a result, each helicase protein was detected by using an antibody specific for the helicase. It was confirmed that, even at the protein level, the expression of these gene products was suppressed when compared to expression in cells into which control RNA (NS) had been introduced (in a 72-hour cell cultivation; FIG. 7).

EXAMPLE 3

Viability of HeLa and TIG3 Cells

Each of the five types of siRNAs against human RecQ helicases selected in Example 2 was introduced into HeLa cells and TIG3 cells. The viable cell number after 96 hours was determined by a colorimetric assay for cell viability based on the cleavage of the tetrazolium salt WST-8 by mitochondrial dehydrogenase using Cell Count Reagent SF (Nacalai Tesque). The absorbance of formazan dye at 450 nm was determined three hours after addition of the reagent.

Figure 8:
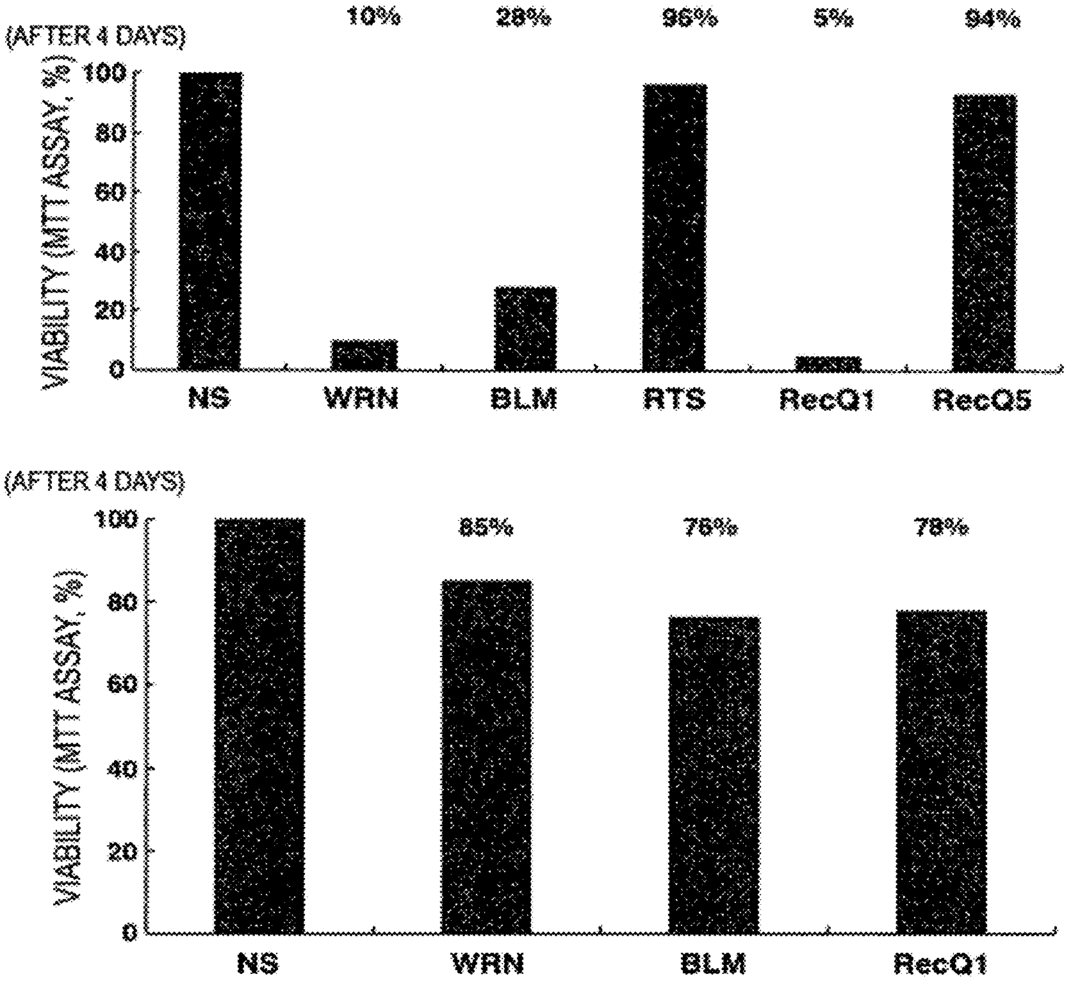
In FIG. 8: Upper panel: A graph showing the results obtained by introducing each of the five types of human RecQ helicase siRNAs into HeLa cells, and then determining cell viability using an MTT assay four days later. NS is the control RNA. Lower panel: A graph showing the results of MTT assays of cell viability four days after the individual introduction of WRN, BLM, and RecQ1 siRNAs into TIG3 cells. NS is the control RNA.

The viability of HeLa cells in which control RNA (NS) had been introduced was taken as 100%. The viabilities of HeLa cells in which RTS and RecQ5 siRNAs had been introduced were 96% and 94%, respectively, showing that viability was not largely affected. However, the viabilities of HeLa cells in which WRN, BLM, and RecQ1 siRNAs had been introduced were 10%, 28%, and 5% respectively, indicating a marked reduction in the viability of HeLa cells (FIG. 8, upper panel). In contrast, the viability of the resulting TIG3 cells was comparable to that of the TIG3 cells into which NS-siRNA had been introduced. The viabilities of cells into which WRN, BLM, and RecQ1 siRNAs were 85%, 76%, and 78%, respectively. Accordingly, the introduction of WRN, BLM, and RecQ1 siRNAs caused no significant reduction in the viability of TIG3 cells (the bottom panel in FIG. 8). These results show that the suppression of WRN, BLM, or RecQ1 expression reduces the viability of HeLa cells but not significantly influence the viability of TIG3 cells.

In addition, the present inventors introduced each of the newly designed siRNAs against RecQ1, WRN, and BLM into HeLa cells, and determined the cell viability by MTT assay after 96 hours. The siRNAs used are shown in FIG. 3.

The result showed that RecQ1-9, WRN4, and BLM2 reduced the viability to 20%, 5%, and 7%, respectively, when the number of cells treated with non-silencing siRNA (NS), a control, was taken as 100% (FIG. 9).

EXAMPLE 4

Effect of siRNA on the Proliferation of A549 Cells

Figure 10:
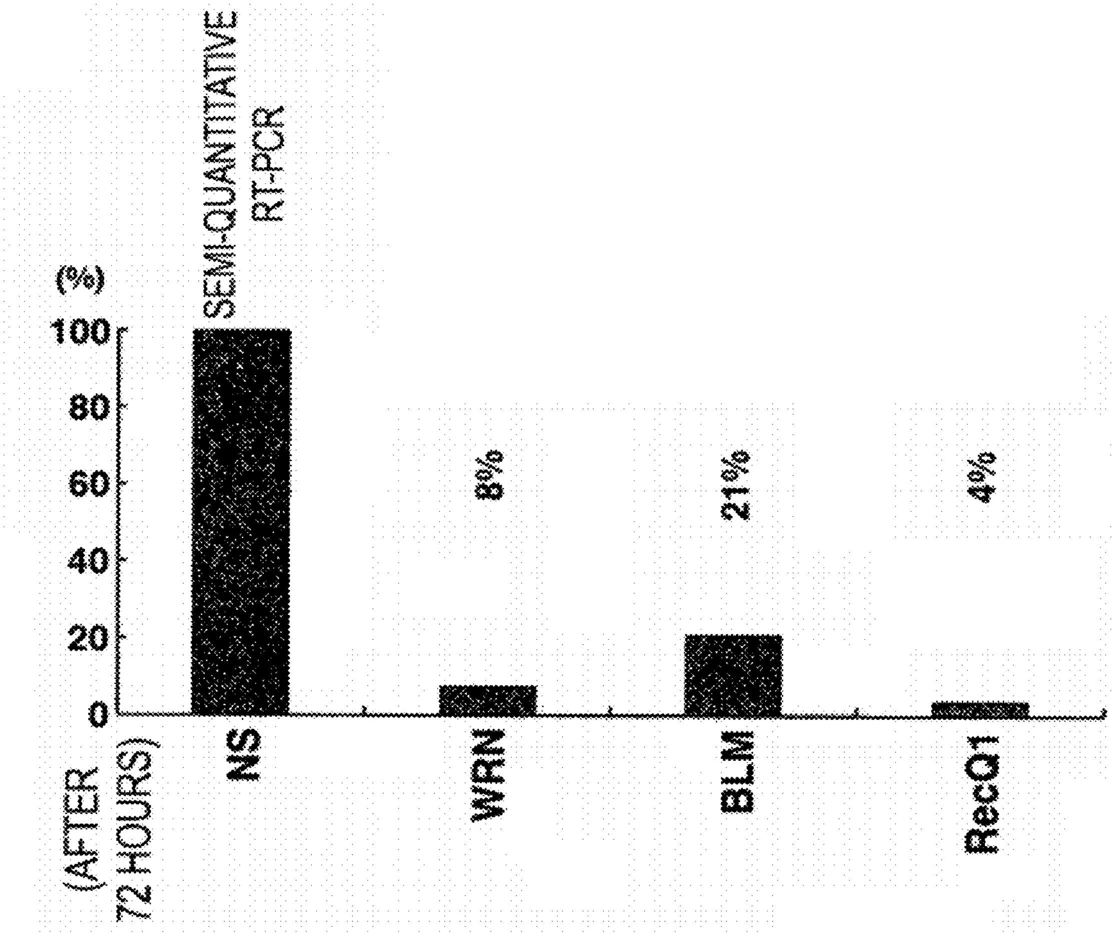
FIG. 10: A graph showing the results obtained by quantifying the mRNA expression of WRN, BLM, and RecQ1 using Taqman PCR 72 hours after the individual introduction of WRN, BLM, and RecQ1 siRNAs into A549 cells. NS is the control RNA.

The effects of the three of WRN, BLM, and RecQ1 siRNAs affecting HeLa cell proliferation in EXAMPLE 3, on the proliferation of human lung cancer-derived A549 cells were examined. WRN, BLM, and RecQ1 siRNAs were introduced into A549 cells, respectively, and 72 hours later, WRN, BLM, RecQ1 mRNA expression was quantified using Taqman PCR. The expression level of each mRNA in cells in which control RNA (NS) had been introduced was taken as 100%. Comparison of the respective mRNA expression levels in the cells into which each siRNA had been introduced revealed that the mRNA expression of WRN, BLM and RecQ1 had been suppressed to 8%, 21%, and 4% respectively (FIG. 10).

Figure 11:
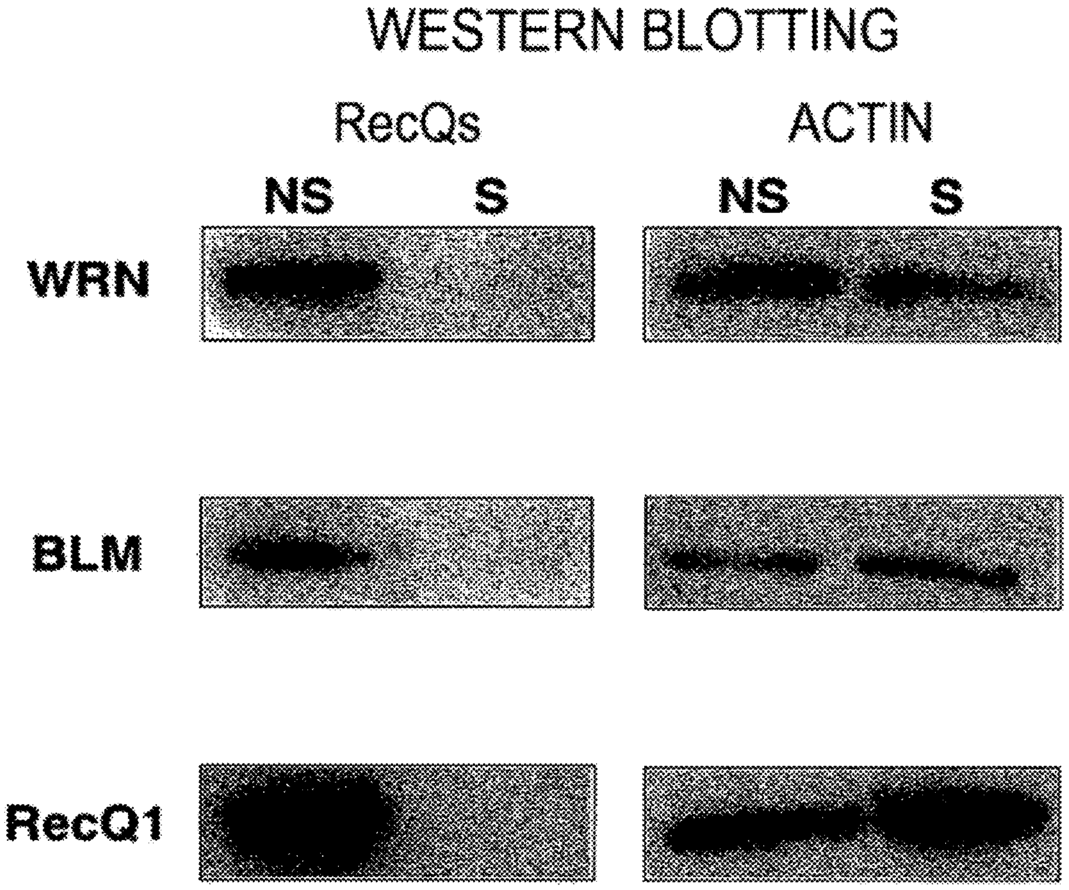
FIG. 11: Photographs showing the results obtained by Western blot analysis for the expression of WRN, BLM, and RecQ1 proteins in A549 cells in which mRNA expression was revealed to be suppressed.

Western blot analysis was used to determine the expression levels of WRN, BLM, and RecQ1 proteins in the A549 cells in which each mRNA expression had been suppressed. As a result, it was confirmed that even at the protein level the expression of these gene products was suppressed when compared to expression in cells into which control RNA (NS) had been introduced (FIG. 11).

EXAMPLE 5

Viability of A549 Cells

Figure 12:
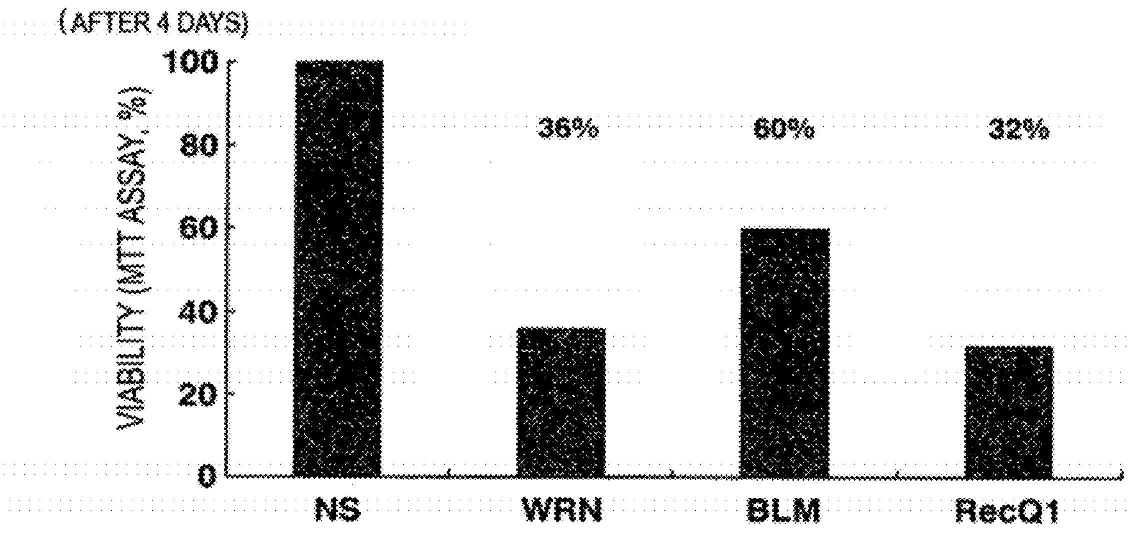
FIG. 12: A graph showing the results of MTT assays of cell viability four days after the individual introduction of WRN, BLM, and RecQ1 siRNAs into A549 cells. NS is the control RNA.

Each of the siRNAs was introduced into A549 cells, respectively. The viability of the cells after four days was assessed using an MTT assay. When the viability of the cells in which control RNA (NS) had been introduced was taken as 100%, the viabilities of cells into which WRN, BLM, and RecQ1 siRNAs had been introduced were 36%, 60%, and 32% respectively. As a result, the viability of A549 cells was found to be markedly reduced (FIG. 12).

EXAMPLE 6

Apoptosis-Inducing Activity of siRNA in HeLa Cells

Next it was investigated as to whether or not apoptosis caused the above-described reduction in viability of the cells into which the siRNAs had been introduced. WRN, BLM, and RecQ1 siRNAs were introduced into HeLa cells, respectively. After 48 hours, the presence of apoptosis induction was examined by the TUNEL method using in situ cell death detection kit (Roche Diagnostics) following the supplier's protocols.

Figure 13:
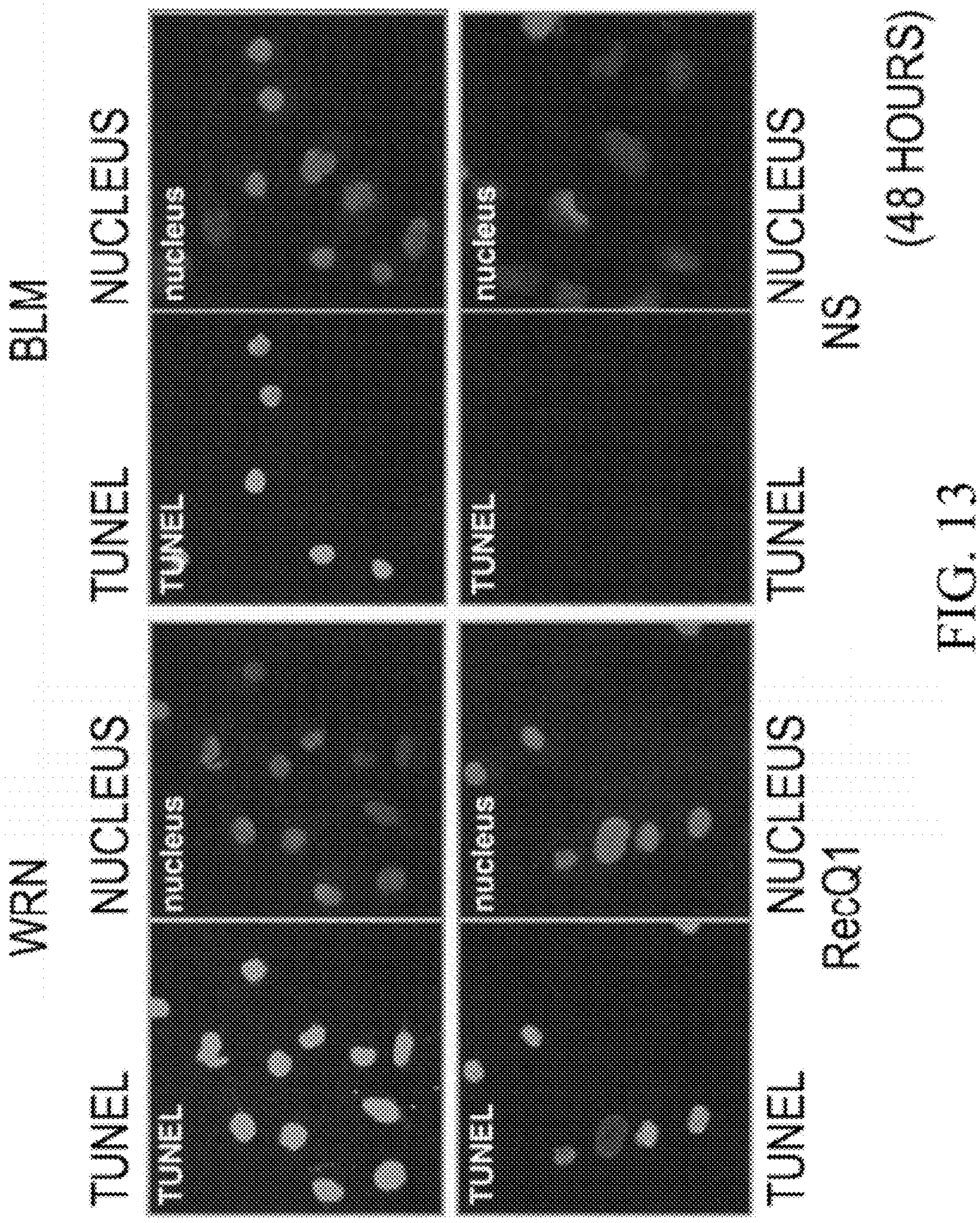
FIG. 13: Photographs showing the results of examination by TUNEL method of the presence of apoptosis induction 48 hours after the individual introduction of WRN, BLM, and RecQ1 siRNAs into HeLa cells, respectively. Each left panel shows the nuclei (green) of cells in which apoptosis was induced. Each right panel shows the nuclei of cells in the same visual field.

Apoptosis induction was clearly recognized in HeLa cells where WRN, BLM, or RecQ1 siRNA had been introduced. However, apoptosis induction was not detectable in HeLa cells in which control RNA (NS) had been introduced (FIG. 13). Furthermore, under the same conditions, apoptosis induction was also not detected in TIG3 cells.

EXAMPLE 7

Apoptosis-Inducing Activity in Various Cells

To determine whether the apoptosis-inducing activities of WRN-siRNA, BLM-siRNA, and RecQ1-siRNA in HeLa cells are specific to the tumor cell or may occur in other tumor cell lines as well, the present inventors evaluated the apoptosis-inducing effects of siRNAs by the same procedure as described in Example 6 using eleven types of tumor cell lines derived from various tumor types: HeLa, A549 (lung cancer), MCF7 (breast cancer), HepG2 (hepatic cancer), U2OS (osteosarcoma), U251 (glioblastoma), UACC62 (melanoma), Caki-1 (renal cancer), KP4 (pancreatic cancer), MKN45 (stomach cancer), and LNCaP (prostatic cancer). The results showed that the siRNAs induced apoptosis in several cancer cells but did not induce apoptosis in normal cells.

The results of investigations into the apoptosis-inducing effects of the siRNAs tested in Examples 6 and 7 are summarized in Table 1.

WRN-siRNA and RecQ1-siRNA were tested for their tumor-suppression effect on the A549 tumor which had been grown in the backs of nude mice (FIGS. 14 and 15). 25 μg of 5'-phosphorylated siRNA was combined with 5 μg of polyethylene imine (molecule weight: 10,000; Wako) in 50 μl of physiological saline. The resulting mixture was injected every three days (day 8, 11, 14, 17, 20, 23, 27, and 32) into the top of the solid tumors (tumor volume: approximately 40 $mm^3$) grown in the eight days after A549 cell inoculation. The tumor volumes were determined using a vernier caliper. The formula for estimating the volumes of the ellipsoidal tumors was: $L \times W^2/2$ (wherein, L represents the major axis of tumors and W represents the minor axis). The tumor volumes were analyzed for statistical significance by a multiple comparison test (Holm-Sidak test).

Figure 14:
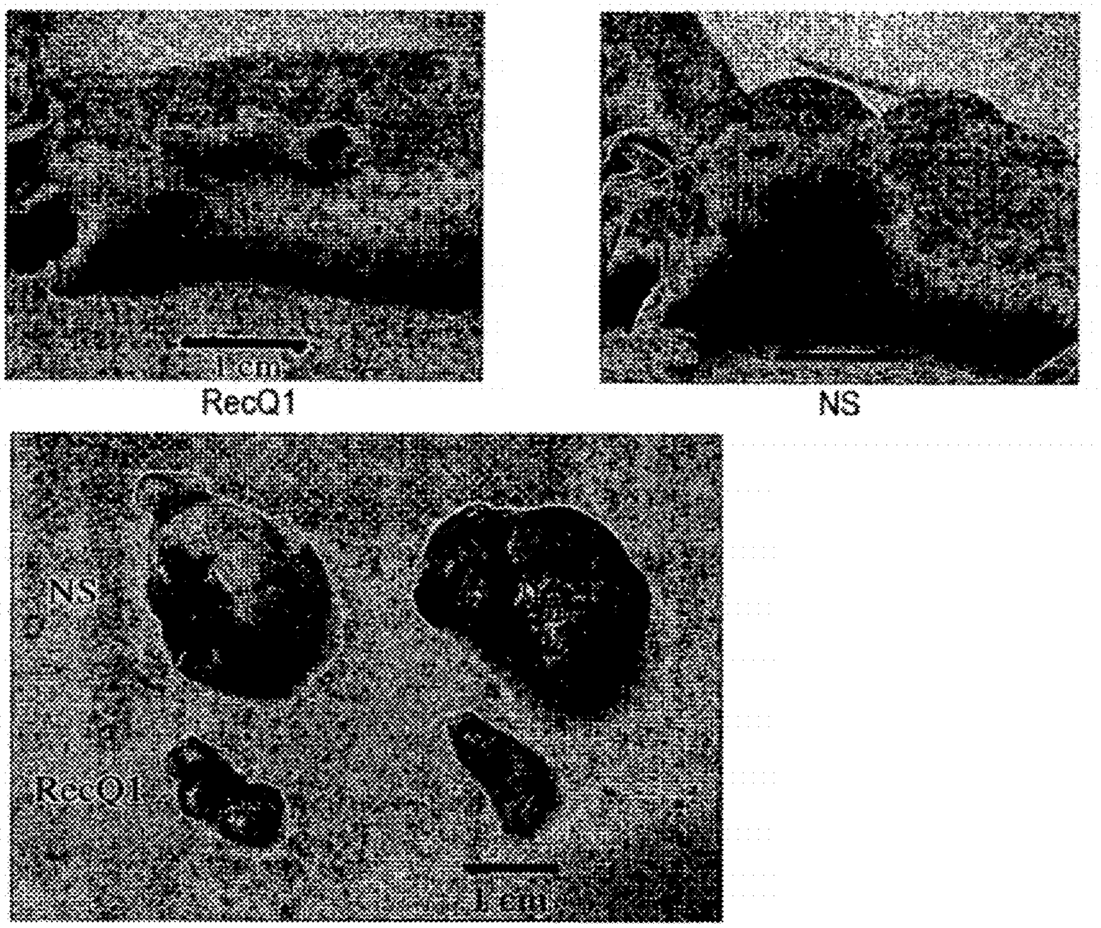
FIG. 14: Photographs showing tumor growth inhibition in nude mice as a result of the introduction of silencing RecQ1-siRNA. The photographs show the whole sizes of the tumor injected with RecQ1-siRNA (top left) and the tumor injected with NS-siRNA (top right), 32 days after inoculation. The bottom panel shows A549 tumors excised from the mice: a tumor injected with NS-siRNA (NS) (top); and a tumor injected with RecQ1-siRNA (RecQ1) (bottom).

The result showed that the development of the A549 tumor was markedly suppressed over 32 days after inoculation of RecQ1-siRNA. However, NS-siRNA mixed with polyethylene imine by the same procedure as described above did not have any effect and caused the A549 tumor to increase in volume (FIG. 14). No weight loss was observed in the mice to which the mixture of RecQ1-siRNA and polyethylene imine was injected as compared to the untreated, cancer-bearing mice. This indicates that this treatment has no serious adverse effect.

In view of these results, the in vivo efficacy of another siRNA, specifically WRN-siRNA, was evaluated in addition to RecQ1-siRNA using more mice (N=6 for testing each siRNA) by periodically measuring tumor volume for 50 days

TABLE 1

| GENE | HeLa | A549 | MCF7 | HepG2 | U2OS | U251 | UACC62 | Caki-1 | KP4 | MKN45 | LNCaP |
|---|---|---|---|---|---|---|---|---|---|---|---|
| WRN | +++ | ++ | ++ | ++ | +++ | +++ | ++ | ++ | ++ | ++ | ++ |
| BLM | +++ | ++ | ++ | + | ++ | +++ | + | ++ | ++ | + | ++ |
| RecQ1 | +++ | ++ | ++ | ++ | +++ | ++ | + | ++ | ++ | + | ++ |

In the Table above, "+++", "++", and "+" indicate that apoptosis was induced in 70% or more, 70% to 40%, and 40% to 20% of cells, respectively.

All eleven types of tumor cell lines listed above were sensitive to the siRNAs against the three types of RecQ helicases, although the level of sensitivity varied depending on the siRNA combination and tumor cell line. When considering transfection efficiency, the effect of each siRNA on tumor cells should be more strictly evaluated. However, what deserves emphasis is that WRN-siRNA, BLM-siRNA, and RecQ1-siRNA are effective for a broad range of tumor types and thus can be candidates for excellent anti-tumor agents. In addition, WRN, BLM, and RecQ1 helicases are promising as tools in screenings for anti-tumor agents.

EXAMPLE 8

Inhibition of Tumor Cell Growth in Tumor-Bearing Animal Models by siRNAs

The present inventors tested whether the RecQ helicase siRNA-mediated selective inhibition of tumor cell growth found in vitro was also achieved in vivo in cancer-bearing animal models.

Male BALB/cA nude mice were purchased from CLEA Japan, Inc. A549 cells ($5 \times 10^6$ cells/0.1 ml) were subcutaneously injected into the back of the nude mice (six- to seven-week-old). siRNA administration was commenced eight days after subcutaneous injection of the tumor cells.

and plotting the mean tumor volume. WRN-siRNA and RecQ1-siRNA were introduced together with a polyethylene imine carrier into each subject by the same procedure as described in the figure legend for FIG. 14. A suspension of polyethylene imine and NS-siRNA prepared by the same procedure as described above was used as a control to evaluate the adverse effects of the pharmaceutical carrier and siRNA themselves.

Figure 15:
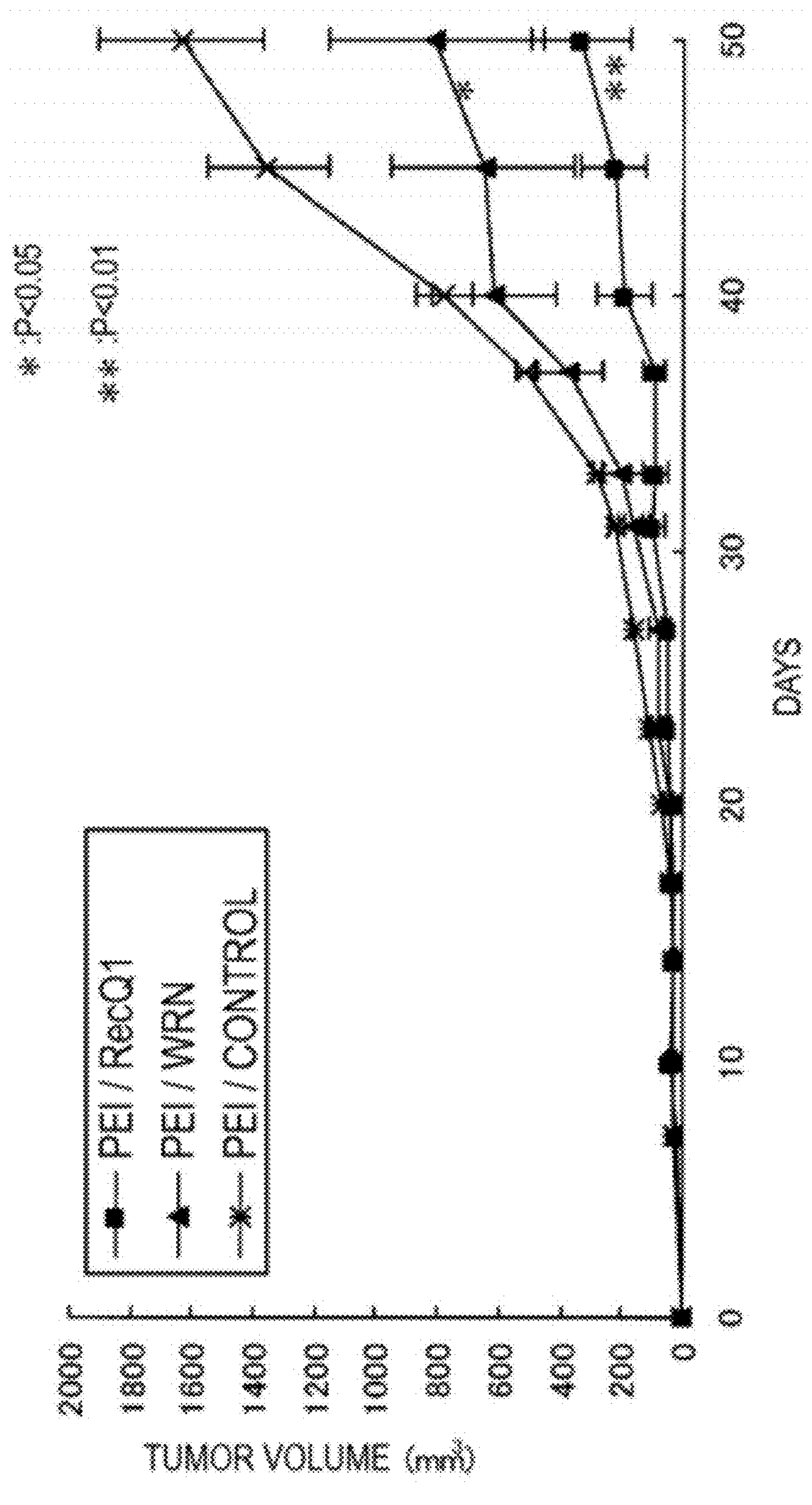
FIG. 15: Time-dependent changes in the inhibitory effects of WRN-siRNA and RecQ1-siRNA on the growth of A549 tumors in nude mice.

FIG. 15 shows that, by day 50, RecQ1-siRNA had efficiently inhibited the increase in tumor volume by about 80% ($P<0.01$) while WRN-siRNA inhibited it by about 50% ($P<0.05$) as compared to NS-siRNA (PEI/control).

Figure 16:
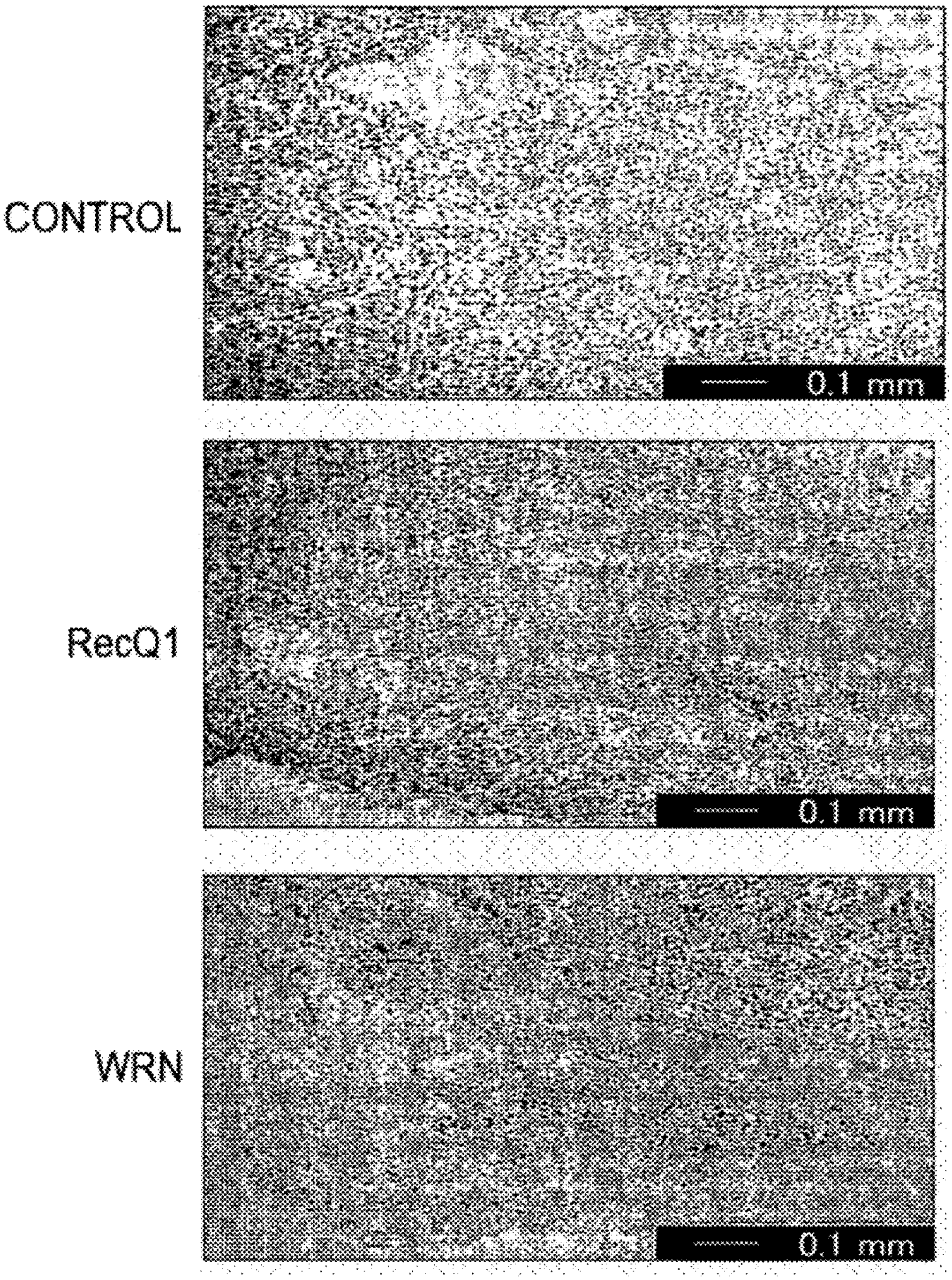
FIG. 16: Photographs showing the presence or absence of apoptosis induction detected by TUNEL method using tumor sections prepared from tumor (A549)-transplanted nude mice introduced with siRNA. Control, RecQ1, and WRN images were obtained by the introduction of NS siRNA, RecQ1 siRNA, and WRN siRNA, respectively. Red-brown indicates apoptotic nuclei, and blue-purple indicates non-apoptotic nuclei.

Furthermore, it was assessed whether or not apoptosis was induced in RecQ1-siRNA- or WRN-siRNA-introduced solid tumor tissues. Tumor tissues were excised 23 days after introduction of RecQ1-siRNA or WRN-siRNA, and fixed with a 4% paraformaldehyde fixative. Then, the tissues were refixed with a neutralized 10% formalin buffer fixative. After a five-day fixation, the tissues were sufficiently washed with water and embedded in paraffin using an automated embedding system. Then, paraffin sections of about 2 μm were prepared, and apoptosis was detected using the ApopTag Peroxidase in situ Apotosis Detection Kit (Serologicals Co.). The result showed that apoptosis-positive cells were found at a significant level in solid tumor tissues to which RecQ1-siRNA or WRN-siRNA had been introduced, as compared to NS-siRNA (FIG. 16).

INDUSTRIAL APPLICABILITY

Compounds that inhibit the expression of a RecQ DNA helicase family gene of the present invention or the function of a protein encoded by the gene, have the activity of selectively inducing apoptosis in cancer cells. Pharmaceutical agents comprising such a compound can be used with very few side effects as anticancer agents whose mechanism is based on this apoptosis-inducing activity. The present invention, for the first time, provides anticancer agents which target RecQ helicase using a mechanism based on apoptosis-inducing activity.

Even if certain compounds are found to have apoptosis-inducing activity, it is difficult to use the compounds as pharmaceuticals when their apoptosis-inducing activities in normal cells are unknown. This is because there may be a risk of adverse effects when the compounds have apoptosis-inducing activities in normal cells. In other words, if the compounds have the apoptosis-inducing activities not specific to cancer cells, in general, it is practically difficult to use the compounds as pharmaceuticals. Accordingly, the pharmaceutical agents (the compounds) of the present invention are very practical and effective because their apoptosis-inducing activities are specific to cancer cells.

The invention claimed is:

1. A method for inducing apoptosis of cancer cells comprising the steps of:

(a) administering a double-stranded RNA that has RNAi activity toward a RecQ1 gene and suppresses the expression of the RecQ1 gene into a subject; and (b) assessing the viability of the subject;

wherein the double stranded RNA induces apoptosis in cancer cells but does not induce apoptosis in normal cells, and comprises a sense RNA comprising a sequence homologous to an arbitrary 20 to 30 consecutive nucleotides from the mRNA of the RecQ1 gene, and an antisense RNA, comprising the sequence complementary to the sense RNA; and wherein either strand of the double-stranded RNA with RNAi activity comprises the nucleotide sequence of any one of SEQ ID NOs: 1, 31 to 34, and 43 to 52.

2. The method according to claim 1, wherein either strand of the double-stranded RNA with RNAi activity consists of the nucleotide sequence of any one of SEQ ID NOs: 1, 31, 43 to 46, 48, 49, and 51.

3. The method according to claim 1, wherein either strand of the double-stranded RNA with RNAi activity consists of the nucleotide sequence of SEQ ID NO: 1.

* * * * *